United States Patent
Strobel et al.

(10) Patent No.: US 8,642,620 B2
(45) Date of Patent: Feb. 4, 2014

(54) HETEROARYL-SUBSTITUTED AMIDES COMPRISING AN UNSATURATED OR CYCLIC LINKER GROUP, AND THEIR USE AS PHARMACEUTICALS

(75) Inventors: Harmut Strobel, Frankfurt am Main (DE); Paulus Wohlfart, Frankfurt am Main (DE); Gerhard Zoller, Frankfurt am Main (DE); David William Will, Frankfurt am Main (DE)

(73) Assignee: Sanofi, Paris (FR)

( * ) Notice: Subject to any disclaimer, the term of this patent is extended or adjusted under 35 U.S.C. 154(b) by 1389 days.

(21) Appl. No.: 11/958,503

(22) Filed: Dec. 18, 2007

(65) Prior Publication Data

US 2008/0167342 A1 Jul. 10, 2008

Related U.S. Application Data

(63) Continuation of application No. PCT/EP2006/005716, filed on Jun. 14, 2006.

(30) Foreign Application Priority Data

Jun. 28, 2005 (EP) ..................................... 05013869

(51) Int. Cl.
*A61K 31/4545* (2006.01)
*C07D 401/06* (2006.01)

(52) U.S. Cl.
USPC ........... 514/326; 514/318; 544/315; 546/194; 546/274.4

(58) Field of Classification Search
USPC ......... 514/326, 318; 546/274.4, 194; 544/315
See application file for complete search history.

(56) References Cited

U.S. PATENT DOCUMENTS

| | | | |
|---|---|---|---|
| 3,192,229 A | 6/1965 | Biel | |
| 5,187,192 A | 2/1993 | Brooks et al. | 514/445 |
| 7,186,735 B2 | 3/2007 | Strobel | |
| 7,572,797 B2 * | 8/2009 | Denton et al. | 514/255.06 |
| 7,576,099 B2 * | 8/2009 | Kelly et al. | 514/311 |
| 2003/0073849 A1 | 4/2003 | Mattson et al. | 348/305.4 |

FOREIGN PATENT DOCUMENTS

| | | |
|---|---|---|
| CA | 2235621 | 5/1997 |
| JP | 7-504412 | 5/1995 |
| JP | 8-12579 A | 1/1996 |
| JP | 2004-507526 A | 3/2004 |
| WO | WO 95/09159 | 4/1995 |
| WO | WO 97/15555 | 5/1997 |
| WO | WO 99/47153 | 9/1999 |
| WO | WO 00/03746 | 1/2000 |
| WO | WO 02/18346 A1 | 3/2002 |
| WO | WO 02/064146 A1 | 8/2002 |
| WO | WO 02/064545 A1 | 8/2002 |
| WO | WO 02/064546 A2 | 8/2002 |
| WO | WO 02/064565 A1 | 8/2002 |
| WO | WO 2004/009579 A1 | 1/2004 |
| WO | WO 2004/014369 A1 | 2/2004 |
| WO | WO 2004/014372 A1 | 2/2004 |
| WO | WO 2004/014842 | 2/2004 |
| WO | WO 2004/094425 | 11/2004 |

OTHER PUBLICATIONS

Exhibit I (2011).*
Brunea et al. "Preparation of 1,2- . . . " CA110:192811 (1989)Weing et al.*
Bagli et al. "phenyl substiutted . . . " CA118:234052 (1993).*
Ewing et al. "Substituted piperazine . . . " CA131:130007 (1999).*
Yao et al. "Palladiium catalyzed . . . " CA138:205002 (2002).*
Dorwald Side Reactions in Organic Synthesis: A Guide to Successful Synthesis Design, Weinheim: Wiley-VCH Verlag GmbH & Co. KGaA, 2005, cover-p. ix (2003).*
Fedorov et al. "Structures of nitric . . . " PNAS v.101(16) p. 5892-5897 (2004).*
Moore et al. "2-iminopiperidine . . . " J. Med. Chem. v.39, p. 669-672 (1996).*
Rojas et al. "Synthesis . . . " Eur. J. Med. chem. v.37, p. 699-705 (2002).*

(Continued)

*Primary Examiner* — Celia Chang
(74) *Attorney, Agent, or Firm* — Scully, Scott, Murphy & Presser, P.C.

(57) ABSTRACT

The present invention relates to N-alkylamides of the formula I,

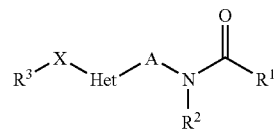

in which A, Het, X, $R^1$, $R^2$ and $R^3$ have the meanings indicated in the claims, which modulate the transcription of endothelial nitric oxide (NO) synthase and are valuable pharmacologically active compounds. Specifically, the compounds of the formula I upregulate the expression of the enzyme endothelial NO synthase and can be applied in conditions in which an increased expression of said enzyme or an increased NO level or the normalization of a decreased NO level is desired. The invention further relates to processes for the preparation of compounds of the formula I, to pharmaceutical compositions comprising them, and to the use of compounds of the formula I for the manufacture of a medicament for the stimulation of the expression of endothelial NO synthase or for the treatment of various diseases including cardiovascular disorders such as atherosclerosis, thrombosis, coronary artery disease, hypertension and cardiac insufficiency, for example.

12 Claims, No Drawings

(56) References Cited

OTHER PUBLICATIONS

Yao et al. "two step stereoselective . . . " Angew Chem. Int. ed. v.41918) p. 3375-3378 (2002).*

Brooks, et al., (R)-(+)-N-[3-{5-[(4-Fluorophenyl)methyl]-2-thienyl]-1-methyl-2-propynyl]-N-hydroxyurea (ABT-761), a Second-Generation 5-Lipoxgenase Inhibitor, J. Med. Chem. (1995), 38, 4766-4775.

Corey, E.J. et al., "Dimethyloxosulfonium Methylide ((CH3)2SOCH2) and Dimethylsulfonium Methylide ((CH3)2SCH2). Formation and Application to Organic Synthesis," Journal of the American Chemical Society (1965), vol. 87, pp. 1353-1364.

Meijere, Armin de et al., "Fine Feathers Make Fine Birds: The Heck Reaction in Modern Garb," Angewandte Chemie International Edition (1994), vol. 33, pp. 2379-2411.

Endres, Matthias et al., "Stroke protection by 3-hydroxy-3-methylglutaryl (HMG)-CoA reductase inhibitors mediated by endothelial nitric oxide synthase," Proceedings of the National Academy of Sciences (1998), vol. 95, pp. 8880-8885.

Kotha, Sambasivarao et al., "Recent applications of the Suzuki-Miyaura cross-coupling reaction in organic synthesis," Tetrahedron(2002),vol. 58, pp. 9633-9695.

Li, Huige et al., "Activation of Protein Kinase Ca and/or Enhances Transcription of the Human Endothelial Nitric Oxide Synthase Gene," Molecular Pharmacology (1998), vol. 53, pp. 630-637.

Miyaura, Norio, "Organoboron Compounds," Topics in Current Chemistry (2002), vol. 219, pp. 11-59.

Moroi, Masao et al., "Interaction of Genetic Deficiency of Endothelial Nitric Oxide, Gender, and Pregnancy in Vascular Response to Injury in Mice," The Journal of Clinical Investigation (1998), vol. 101, No. 6, pp. 1225-12323.

Nakayama, Masafumi et al., "T-786—>C Mutation in the 5"-Flanking Region of the Endothelial Nitric Oxide Synthase Gene is Associated with Coronary Spasm," Circulation (1999), vol. 99, pp. 2864-2870.

Sessa, William C. et al., "Chronic Exercise in Dogs Increases Coronary Vascular Nitric Oxide Production and Endothelial Cell Nitric Oxide Synthase Gene Expression," Circulation Research (1994), vol. 74, pp. 349-353.

Tilley, Jefferson W. et al., "A Convenient Palladium-Catalyzed Coupling Approach to 2,5-Disubstituted Pyridines," The Journal of Organic Chemistry (1988), vol. 53, pp. 386-390.

Varenne, Olivier et al., "Percutaneous Gene Therapy Using Recombinant Adenoviruses Encoding Human Herpes Simplex Virus Thymidine Kinase, Human PAI-1, and Human NOS3 in Balloon-Injured Porcine Coronary Arteries," Human Gene Therapy (2000), vol. 11, pp. 1329-1339.

Walker, Shawn D. et al., "Rationally Designed Universal Catalyst for Suzuki-Miyaura Coupling Processes," Angewandte Chemie International Edition (2004), vol. 43, pp. 1871-1876.

* cited by examiner

HETEROARYL-SUBSTITUTED AMIDES COMPRISING AN UNSATURATED OR CYCLIC LINKER GROUP, AND THEIR USE AS PHARMACEUTICALS

This application is a Continuation of International Application No. PCT/EP2006/005716, filed Jun. 14, 2006.

FIELD OF THE INVENTION

The present invention relates to N-alkylamides of the formula I,

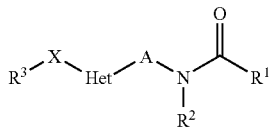

in which A, Het, X, $R^1$, $R^2$ and $R^3$ have the meanings indicated below, which modulate the transcription of endothelial nitric oxide (NO) synthase and are valuable pharmacologically active compounds. Specifically, the compounds of the formula I upregulate the expression of the enzyme endothelial NO synthase and can be applied in conditions in which an increased expression of said enzyme or an increased NO level or the normalization of a decreased NO level is desired. The invention further relates to processes for the preparation of compounds of the formula I, to pharmaceutical compositions comprising them, and to the use of compounds of the formula I for the manufacture of a medicament for the stimulation of the expression of endothelial NO synthase or for the treatment of various diseases including cardiovascular disorders such as atherosclerosis, thrombosis, coronary artery disease, hypertension and cardiac insufficiency, for example.

BACKGROUND OF THE INVENTION

Endothelial NO synthase (eNOS, NOS-III) belongs to a group of three isoenzymes which produce nitric oxide (nitrogen monoxide, NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349) were able to obtain a marked increase in eNOS by means of exercise training and the increase in shear stress associated therewith.

Whether regulation at the post-transcriptional level is relevant in vivo, has not been unambiguously proven. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides to the lipid lowering, also in part to an increase in eNOS expression in vivo (Endres et al., Proc. Natl. Acad. Sci. USA 95 (1998) 8880). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329).

Some low molecular weight compounds which, in cell cultures, may lead to a direct effect on eNOS transcription and expression are disclosed in the literature. For the statins, as has already been mentioned, it has been possible to show such an increase in eNOS in vivo as a side effect. In view of the known range of side effects of this class of substances, however, it is unclear how far use of this effect can be made in a toxicologically unproblematic dose. Liao et al. claim in WO 99/47153 and WO 00/03746 the use of rhoGTPase inhibitors and agents which influence the organization of the actin cytoskeleton for increasing eNOS in endothelial cells and for the therapy of various disorders such as, for example, strokes or pulmonary hypertension without, however, indicating a specific way of achieving this. Certain amide derivatives which upregulate the expression of endothelial NO synthase, in particular N-cycloalkyl amides in which the cycloalkyl ring is fused to a benzene ring or a heteroaromatic ring, have been described in WO 02/064146, WO 02/064545, WO 02/064546, WO 02/064565, WO 2004/014369, WO 2004/014372 and WO 2004/014842. Certain triaza- and tetraaza-anthracenedione derivatives which upregulate the expression of endothelial NO synthase have been described in WO 2004/094425. There still exists a need for further compounds which upregulate the expression of endothelial NO synthase and have a favorable property profile and are useful as pharmaceuticals for the treatment of various diseases such as atherosclerosis, coronary artery disease or cardiac insufficiency, for example. Surprisingly it has now been found that the compounds of the formula I are modulators of the transcription of endothelial NO synthase and in particular stimulate, or upregulate, the expression of eNOS, and are useful for the treatment of various diseases such as the mentioned cardiovascular disorders.

SUMMARY OF THE INVENTION

A subject of the present invention is a compound of the formula I,

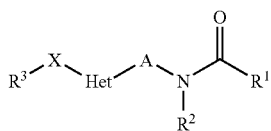

I in which
A is chosen from $-CH=CH-CH_2-$, $-C\equiv C-CH_2-$, which groups are bonded to the group Het via the terminal atom of the double or triple bond, the group of the formula II, which is bonded to the group Het via a ring atom, and the group of the formula III,

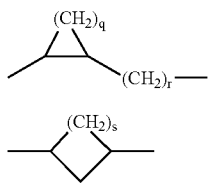

wherein in the formulae II and III the bonds via which the groups are connected to the adjacent groups, are depicted by the lines starting at ring atoms and at the group $(CH_2)_r$, and wherein all groups A can be substituted by one or more identical or different substituents $R^4$;
Het is a 5-membered or 6-membered, monocyclic aromatic group which contains one or two identical or different hetero ring members chosen from N, $NR^{13}$, O and S and which can be substituted by one or more identical or different substituents $R^5$;
X is chosen from a direct bond, $CH_2$, O and NH;
$R^1$ and $R^2$ are independently of each other chosen from $(C_1-C_6)$-alkyl, $(C_3-C_6)$-alkenyl, $(C_3-C_6)$-alkynyl, $(C_3-C_7)$-cycloalkyl-$C_nH_{2n}$—, phenyl-$C_nH_{2n}$— and heteroaryl-$C_nH_{2n}$—, and $R^2$ can in addition be hydrogen, wherein the groups $(C_1-C_6)$-alkyl, $(C_3-C_7)$-cycloalkyl, $(C_3-C_6)$-alkenyl and $(C_3-C_6)$-alkynyl can all be substituted by one or more identical or different substituents $R^6$, and the groups $C_nH_{2n}$ can all be substituted by one or more identical or different substituents chosen from fluorine and $(C_1-C_4)$-alkyl, and all phenyl groups and heteroaryl groups can independently of each other be substituted by one or more identical or different substituents $R^7$, or $R^1$ and $R^2$, together with the N—CO group which carries them, form a 4-membered to 10-membered, monocyclic or bicyclic, saturated or unsaturated ring which, in addition to the ring nitrogen atom being part of the N—CO group, can contain one or two further hetero ring members chosen from N, $NR^{12}$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the N—CO group which carries them can be substituted by one or more identical or different substituents $R^8$;
$R^3$ is chosen from phenyl, naphthalenyl and heteroaryl which can all be substituted by one or more identical or different substituents chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—;
$R^4$ is chosen from $(C_1-C_4)$-alkyl and fluorine;
$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$ and $(C_1-C_4)$-alkyl-$SO_2$—;
$R^6$ is chosen from fluorine, OH, oxo, $(C_1-C_4)$-alkyloxy, $(C_1-C_4)$-alkylmercapto, di$((C_1-C_4)$-alkyl)amino, $((C_1-C_4)$-alkyl)-CONH—, di$((C_1-C_4)$-alkyl)aminocarbonyl-, $((C_1-C_4)$-alkyloxy)carbonyl-, COOH, $CONH_2$, CN and $CF_3$;
$R^7$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—;
$R^8$ is chosen from halogen, $(C_1-C_4)$-alkyl, $(C_3-C_7)$-cycloalkyl-$C_nH_{2n}$—, phenyl-$C_nH_{2n}$—, heteroaryl-$C_nH_{2n}$—, $(C_1-C_4)$-alkyloxy-$(C_1-C_2)$-alkyl-, OH, oxo, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy;
$R^{12}$ is chosen from hydrogen, $(C_1-C_4)$-alkyl, $(C_3-C_7)$-cycloalkyl-$C_nH_{2n}$—, phenyl-$C_nH_{2n}$—, heteroaryl-$C_nH_{2n}$—, $((C_1-C_4)$-alkyl)-CO—, $(C_3-C_7)$-cycloalkyl-$C_nH_{2n}$—CO—, phenyl-$C_nH_{2n}$—CO—, heteroaryl-$C_nH_{2n}$—CO—, $((C_1-C_4)$-alkyl)-O—CO— and phenyl-$C_nH_{2n}$—O—CO—, wherein all phenyl groups and heteroaryl groups can be substituted by one or more identical or different substituents chosen from halogen, $(C_1-C_4)$-alkyl, $CF_3$ and $(C_1-C_4)$-alkyloxy;
$R^{13}$ is chosen from hydrogen, $(C_1-C_4)$-alkyl and phenyl-$C_nH_{2n}$—, wherein the phenyl group can be substituted by one or more identical or different substituents chosen from halogen, $(C_1-C_4)$-alkyl, $CF_3$ and $(C_1-C_4)$-alkyloxy, where all groups $R^{13}$ are independent of each other and can be identical or different;

heteroaryl is a 5-membered or 6-membered, monocyclic aromatic group which contains one, two or three identical or different hetero ring members chosen from N, $NR^{13}$, O and S;
n is 0, 1 or 2, where all numbers n are independent of each other and can be identical or different;
q is 1, 2, 3, 4 or 5;
r is 0 or 1;
s is 1, 2, 3 or 4;
in any of its stereoisomeric forms or a mixture of stereoisomeric forms in any ratio, or a physiologically acceptable salt thereof.

Another subject of the present invention is the use of a compound of the formula Ia

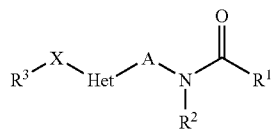

in which
A is chosen from —CH=CH—CH$_2$—, —C≡C—CH$_2$—, which groups are bonded to the group Het via the terminal atom of the double or triple bond, the group of the formula II, which is bonded to the group Het via a ring atom, and the group of the formula III,

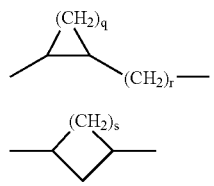

wherein in the formulae II and III the bonds via which the groups are connected to the adjacent groups, are depicted by the lines starting at ring atoms and at the group $(CH_2)_r$, and wherein all groups A can be substituted by one or more identical or different substituents $R^4$;
Het is 5-membered to 10-membered, monocyclic or bicyclic, aromatic group which contains one or more identical or different hetero ring members chosen from N, $NR^{13}$, O and S and which can be substituted by one or more identical or different substituents $R^5$;
X is chosen from a direct bond, $CH_2$, O, S, NH and $N((C_1$-$C_4)$-alkyl), or X is absent and in this case the phenyl, naphthalenyl or heteroaryl group representing the group $R^3$ is fused to the group Het;
$R^1$ and $R^2$ are independently of each other chosen from $(C_1$-$C_{10})$-alkyl, $(C_3$-$C_{10})$-alkenyl, $(C_3$-$C_{10})$-alkynyl, $(C_3$-$C_{10})$-cycloalkyl-$C_nH_{2n}$—, phenyl-$C_nH_{2n}$—, naphthalenyl-$C_nH_{2n}$— and heteroaryl-$C_nH_{2n}$—, and $R^2$ can in addition be hydrogen, wherein the groups $(C_1$-$C_{10})$-alkyl, $(C_3$-$C_{10})$-cycloalkyl, $(C_3$-$C_{10})$-alkenyl and $(C_3$-$C_{10})$-alkynyl can all be substituted by one or more identical or different substituents $R^6$, and the groups $C_nH_{2n}$ can all be substituted by one or more identical or different substituents chosen from fluorine and $(C_1$-$C_4)$-alkyl, and all phenyl, naphthalenyl and heteroaryl groups can independently of each other be substituted by one or more identical or different substituents $R^7$,
or $R^1$ and $R^2$, together with the N—CO group which carries them, form a 4-membered to 10-membered, monocyclic or bicyclic, saturated or unsaturated ring which, in addition to the ring nitrogen atom being part of the N—CO group, can contain one or two further hetero ring members chosen from N, $NR^{12}$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the N—CO group which carries them can be substituted by one or more identical or different substituents $R^8$;
$R^3$ is chosen from phenyl, naphthalenyl and heteroaryl which can all be substituted by one or more identical or different substituents chosen from halogen, $(C_1$-$C_6)$-alkyl, $(C_1$-$C_6)$-alkyloxy-$(C_1$-$C_6)$-alkyl-, OH, $(C_1$-$C_6)$-alkyloxy which can be substituted by one or more fluorine atoms, $(C_1$-$C_3)$-alkylenedioxy which can be substituted by one or more fluorine atoms, $(C_1$-$C_6)$-alkylmercapto, $NH_2$, $(C_1$-$C_6)$-alkylamino, di($(C_1$-$C_6)$-alkyl)amino, $((C_1$-$C_6)$-alkyl)-CONH—, di($(C_1$-$C_6)$-alkyl)aminocarbonyl-, $((C_1$-$C_6)$-alkyl)aminocarbonyl-, $((C_1$-$C_6)$-alkyloxy)carbonyl-, COOH, $CONH_2$, CN, $CF_3$, $((C_1$-$C_6)$-alkyl)$NHSO_2$—, di($(C_1$-$C_6)$-alkyl)$NSO_2$—, $H_2NSO_2$— and $(C_1$-$C_6)$-alkyl-$SO_2$—;
$R^4$ is chosen from $(C_1$-$C_6)$-alkyl, halogen and oxo;
$R^5$ is chosen from halogen, $(C_1$-$C_6)$-alkyl, phenyl-$C_nH_{2n}$—, $(C_1$-$C_6)$-alkyloxy-$(C_1$-$C_3)$-alkyl-, OH, $(C_1$-$C_6)$-alkyloxy which can be substituted by one or more fluorine atoms, $(C_1$-$C_6)$-alkylmercapto, $NH_2$, $(C_1$-$C_6)$-alkylamino, di($(C_1$-$C_6)$-alkyl)amino, $((C_1$-$C_6)$-alkyl)-CONH—, di($(C_1$-$C_6)$-alkyl)aminocarbonyl-, $((C_1$-$C_6)$-alkyl)aminocarbonyl-, $((C_1$-$C_6)$-alkyloxy)carbonyl-, COOH, $CONH_2$, CN, $CF_3$, $H_2NSO_2$—, $((C_1$-$C_6)$-alkyl)$NHSO_2$—, di($(C_1$-$C_6)$-alkyl)$NSO_2$— and $(C_1$-$C_6)$-alkyl-$SO_2$—, wherein the phenyl group can be substituted by one or more identical or different substituents chosen from halogen, $(C_1$-$C_4)$-alkyl, $CF_3$ and $(C_1$-$C_4)$-alkyloxy;
$R^6$ is chosen from fluorine, OH, oxo, $(C_1$-$C_6)$-alkyloxy, $(C_1$-$C_6)$-alkylmercapto, di($(C_1$-$C_6)$-alkyl)amino, $((C_1$-$C_6)$-alkyl)-CONH—, di($(C_1$-$C_6)$-alkyl)aminocarbonyl-, $((C_1$-$C_6)$-alkyloxy)carbonyl-, COOH, $CONH_2$, CN and $CF_3$;
$R^7$ is chosen from halogen, $(C_1$-$C_6)$-alkyl, $(C_1$-$C_6)$-alkyloxy-$(C_1$-$C_3)$-alkyl-, OH, $(C_1$-$C_6)$-alkyloxy which can be substituted by one or more fluorine atoms, $(C_1$-$C_3)$-alkylenedioxy which can be substituted by one or more fluorine atoms, $(C_1$-$C_6)$-alkylmercapto, $NH_2$, $(C_1$-$C_6)$-alkylamino, di($(C_1$-$C_6)$-alkyl)amino, $((C_1$-$C_6)$-alkyl)-CONH—, di($(C_1$-$C_6)$-alkyl)aminocarbonyl-, $((C_1$-$C_6)$-alkyl)aminocarbonyl-, $((C_1$-$C_6)$-alkyloxy)carbonyl-, COOH, $CONH_2$, CN, $CF_3$, $SF_5$, $H_2NSO_2$—, $((C_1$-$C_6)$-alkyl)$NHSO_2$—, di($(C_1$-$C_6)$-alkyl)$NSO_2$— and $(C_1$-$C_6)$-alkyl-$SO_2$—;
$R^8$ is chosen from halogen, $(C_1$-$C_6)$-alkyl, $(C_3$-$C_7)$-cycloalkyl-$C_nH_{2n}$—, phenyl-$C_nH_{2n}$—, heteroaryl-$C_nH_{2n}$—, $(C_1$-$C_6)$-alkyloxy-$(C_1$-$C_3)$-alkyl-, OH, oxo, $(C_1$-$C_6)$-alkyloxy which can be substituted by one or more fluorine atoms, $(C_1$-$C_3)$-alkylenedioxy which can be substituted by one or more fluorine atoms, $(C_1$-$C_6)$-alkylmercapto, $NH_2$, $(C_1$-$C_6)$-alkylamino, di($(C_1$-$C_6)$-alkyl)amino, $((C_1$-$C_6)$-alkyl)-CONH—, di($(C_1$-$C_6)$-alkyl)aminocarbonyl-, $((C_1$-$C_6)$-alkyl)aminocarbonyl-, $((C_1$-$C_6)$-alkyloxy)carbonyl-, COOH, $CONH_2$, CN, $CF_3$, $SF_5$, $H_2NSO_2$— and $(C_1$-$C_6)$-alkyl-$SO_2$—, wherein all phenyl groups and heteroaryl groups can independently of each other be substituted by one or more identical or different substituents chosen from halogen, $(C_1$-$C_4)$-alkyl, $CF_3$ and $(C_1$-$C_4)$-alkyloxy;
$R^{12}$ is chosen from hydrogen, $(C_1$-$C_6)$-alkyl, $(C_3$-$C_7)$-cycloalkyl-$C_nH_{2n}$—, phenyl-$C_nH_{2n}$—, heteroaryl-$C_nH_{2n}$—, $((C_1$-$C_6)$-alkyl)-CO—, $(C_3$-$C_7)$-cycloalkyl-$C_nH_{2n}$—CO—, phenyl-$C_nH_{2n}$—CO—, heteroaryl-$C_nH_{2n}$—CO—, $((C_1$-$C_6)$-alkyl)-O—CO— and phenyl-$C_nH_{2n}$—O—CO—, wherein all phenyl groups and heteroaryl groups can be substituted by one or more identical or different substituents chosen from halogen, $(C_1-C_4)$-alkyl, $CF_3$ and $(C_1-C_4)$-alkyloxy;

$R^{13}$ is chosen from hydrogen, $(C_1-C_4)$-alkyl and phenyl-$C_nH_{2n}$—, wherein the phenyl group can be substituted by one or more identical or different substituents chosen from halogen, $(C_1-C_4)$-alkyl, $CF_3$ and $(C_1-C_4)$-alkyloxy, where all groups $R^{13}$ are independent of each other and can be identical or different;

heteroaryl is a 5-membered to 10-membered, monocyclic or bicyclic aromatic group which contains one or more identical or different hetero ring members chosen from N, $NR^{13}$, O and S;

n is 0, 1, 2 or 3, where all numbers n are independent of each other and can be identical or different;

q is 1, 2, 3, 4 or 5;

r is 0 or 1;

s is 1, 2, 3 or 4;

in any of its stereoisomeric forms or a mixture of stereoisomeric forms in any ratio, or a physiologically acceptable salt thereof, for the manufacture of a medicament for the stimulation of the expression of endothelial NO synthase and for the treatment of a disease in which such a stimulation, or an increase in NO level, is desired, for example a cardiovascular disorder such as atherosclerosis, coronary artery disease or cardiac insufficiency or any other disease mentioned above or below herein.

DETAILED DESCRIPTION OF THE INVENTION

If in the compounds of the formulae I and Ia any groups, substituents, hetero ring members, numbers or other features such as, for example, $R^4$, $R^5$, $R^6$, $R^7$, $R^8$, $R^{12}$, $R^{13}$, alkyl groups, the number n, etc. can occur several times, they can all independently of one another have any of the indicated meanings and can in each case be identical or different from one another. In a dialkylamino group, for example, the alkyl groups can be identical or different.

Alkyl, alkenyl and alkynyl groups can be linear, i.e. straight-chain, or branched. This also applies when they are part of other groups, for example alkyloxy groups (=alkoxy groups, i.e. alkyl-O— groups), alkyloxycarbonyl groups or alkyl-substituted amino groups, or when they are substituted. Substituted alkyl, alkenyl and alkynyl groups can be substituted by one or more, for example one, two, three, four or five, identical or different substituents which can be located in any desired positions. Examples of alkyl groups are methyl, ethyl, propyl, butyl, pentyl, hexyl, heptyl, octyl, nonyl, decyl, the n-isomers of these groups, isopropyl, isobutyl, isopentyl, sec-butyl, tert-butyl, neopentyl or 3,3-dimethylbutyl. Alkenyl groups and alkynyl groups preferably contain one double bond or triple bond, respectively, which can be present in any desired position of the group. Examples of alkenyl and alkynyl are prop-1-enyl, prop-2-enyl (=allyl), but-2-enyl, 2-methylprop-2-enyl, 3-methylbut-2-enyl, hex-3-enyl, hex-4-enyl, 4-methylhex-4-enyl, dec-3-enyl, dec-9-enyl, prop-2-ynyl (=propargyl), but-2-ynyl, but-3-ynyl, hex-4-ynyl or hex-5-ynyl.

As far as applicable, the preceding explanations regarding alkyl, alkenyl and alkynyl groups apply correspondingly to divalent alkyl, alkenyl and alkynyl groups, i.e. alkanediyl groups and alkylene groups, alkenediyl groups and alkenylene groups, and alkynediyl groups and alkynylene groups, such as the methylene group —$CH_2$— and the groups —$CH_2$—$CH_2$— and —$CH_2$—$CH_2$—$CH_2$—, the propenylene group —CH═CH—$CH_2$— and the propynylene group —C≡C—$CH_2$— which can occur in the group A and in divalent alkylenedioxy groups such as —O—$CH_2$—O—, —O—$CH_2$—$CH_2$—O— or —O—$CH_2$—$CH_2$—$CH_2$—O—, and the groups $C_nH_{2n}$. As far as applicable, these groups can also be linear or branched and/or can be substituted by one or more, for example one, two, three, four or five, identical or different substituents which can be located in any desired positions, including the carbon atoms which are part of a double or triple bond. Of course, the number of substituents can in general not exceed the number of hydrogen atoms in the unsubstituted parent system which can be replaced with a substituent, and can, for example, be only one or two in the case of a $CH_2$ group. Examples of the group $C_nH_{2n}$, in which the number n is 1, 2, or 3, are —$CH_2$—, —$CH_2$—$CH_2$—, —$CH_2$—$CH_2$—$CH_2$—, —$CH(CH_3)$—, —$C(CH_3)_2$—, —$CH(CH_3)$—$CH_2$—, —$CH_2$—$CH(CH_3)$—. If the number n in the group $C_nH_{2n}$ or the number r in the group $(CH_2)_r$ is 0 (=zero), the two groups which are attached to the group $C_nH_{2n}$ or $(CH_2)_r$ are directly connected to one another via a single bond. Similarly, if the group X is a direct bond, the groups $R^3$ and Het are directly connected to one another via a single bond.

Examples of cycloalkyl groups are cyclopropyl, cyclobutyl, cyclopentyl, cyclohexyl, cycloheptyl, cyclooctyl, cyclononyl and cyclodecyl. Substituted cycloalkyl groups can be substituted by one or more, for example one, two, three, four or five, identical or different substituents which can be located in any desired positions. In general, besides any other specified substituents, all cycloalkyl groups can also carry one or more, for example one, two, three, four or five, identical or different $(C_1-C_4)$-alkyl substituents, for example methyl substituents, which can be located in any desired positions. Examples of alkyl-substituted cycloalkyl groups are 4-methylcyclohexyl, 4-tert-butylcyclohexyl or 2,3-dimethylcyclopentyl.

The preceding explanations regarding cycloalkyl groups apply correspondingly to divalent cycloalkyl groups, i.e. cycloalkanediyl groups and cycloalkylene groups, such as the group of the formula III and the cyclic subgroup which is present in the group of the formula II or represents the group of the formula II in case the number r is 0. These groups can also be substituted by one or more, for example one, two, three, four or five, identical or different substituents which can be located in any desired positions. Of course, the number of substituents can in general not exceed the number of hydrogen atoms in the unsubstituted parent system which can be replaced with a substituent. Examples of the divalent cyclic subgroup present in, or representing, the group of the formula II, which is bonded to the adjacent groups via two ring atoms in positions 1 and 2, are cyclopropan-1,2-diyl, cyclobutan-1,2-diyl, cyclopentan-1,2-diyl, cyclohexan-1,2-diyl, cycloheptan-1,2-diyl. Examples of the divalent group of the formula III, which is bonded to the adjacent groups via two ring atoms in positions 1 and 3, are cyclobutan-1,3-diyl, cyclopentan-1,3-diyl, cyclohexan-1,3-diyl, cycloheptan-1,3-diyl.

If a group like phenyl, naphthalenyl and heteroaryl, which can be unsubstituted or substituted, is substituted by one or more substituents, in general it can carry one, two, three, four or five identical or different substituents, for example. The substituents can be located in any desired positions. Substituted heteroaryl groups can be substituted on ring carbon atoms and/or on suitable ring nitrogen atoms, i.e. ring nitrogen atoms which in the parent ring system carry a hydrogen atom, where preferred substituents on such substituted ring nitrogen atoms are alkyl groups, for example $(C_1-C_4)$-alkyl groups, unless stated otherwise. Suitable ring nitrogen atoms, such as the ring nitrogen atoms in a pyridine ring or a quinoline ring, can also be present as N-oxides or as quaternary salts, the latter preferably having a counter-anion which is derived from a physiologically acceptable acid. In monosubstituted phenyl groups the substituent can be located in the 2-position, the 3-position or the 4-position. In a disubstituted phenyl group the substituents can be located in 2,3-position, 2,4-position, 2,5-position, 2,6-position, 3,4-position or 3,5-position. In trisubstituted phenyl groups the substituents can be located in 2,3,4-position, 2,3,5-position, 2,3,6-position, 2,4,5-position, 2,4,6-position or 3,4,5-position. Naphthalenyl (=naphthyl) can be naphthalen-1-yl or naphthalen-2-yl. In monosubstituted naphthalen-1-yl groups the substituent can be located in the 2-, 3-, 4-, 5-, 6-, 7-, or 8-position, in monosubstituted naphthalen-2-yl groups the substituent can be located in the 1-, 3-, 4-, 5-, 6-, 7-, or 8-position. In disubstituted naphthalenyl groups the substituents can likewise occur in any desired positions in the ring via which the naphthalenyl group is bonded, and/or in the other ring.

Heteroaryl groups are preferably 5-membered or 6-membered monocyclic aromatic heterocyclic groups or 9-membered or 10-membered bicyclic aromatic heterocyclic groups, where the bicyclic groups contain a 6-membered ring fused to a 5-membered or two fused 6-membered rings. In bicyclic heteroaryl groups one or both rings can be aromatic and one or both rings can contain hetero ring members. Preferably heteroaryl groups and other heterocyclic groups contain one, two or three, for example one or two, identical or different ring hetero ring members. The hetero ring members or ring heteroatoms in heteroaryl groups and other heterocyclic groups are generally chosen from N, O and S wherein N includes ring nitrogen atoms which carry a hydrogen atom or any substituent as is the case in 5-membered aromatic heterocycles such as pyrrole, pyrazole or imidazole, for example. The hetero ring members in heteroaryl groups and other heterocyclic groups can be located in any desired positions provided that the resulting heterocyclic system is known in the art and is stable and suitable as a subgroup in a drug substance. For example, in general two atoms from the series O and S cannot be present in adjacent ring positions. Examples of parent heterocycles of heteroaryl groups and other heterocyclic groups are pyrrole, furan, thiophene, imidazole, pyrazole, 1,2,3-triazole, 1,2,4-triazole, oxazole (=1,3-oxazole), isoxazole (=1,2-oxazole), thiazole (=1,3-thiazole), isothiazole (=1,2-thiazole), tetrazole, pyridine, pyridazine, pyrimidine, pyrazine, 1,2,3-triazine, 1,2,4-triazine, 1,3,5-triazine, 1,2,4,5-tetrazine, indole, benzothiophene, benzofuran, 1,3-benzodioxole (=1,2-methylenedioxybenzene), 1,3-benzoxazole, 1,3-benzothiazole, benzoimidazole, chroman, isochroman, 1,4-benzodioxane (=1,2-ethylenedioxybenzene), quinoline, isoquinoline, cinnoline, quinazoline, quinoxaline, phthalazine, thienothiophenes, 1,8-naphthyridine and other naphthyridines, acridine or pteridine. Heteroaryl and other heterocyclic groups can be bonded via any desired suitable ring carbon atom and, in the case of nitrogen heterocycles, ring nitrogen atom. Preferably they are bonded via a ring carbon atom. For example, thiophenyl (=thienyl) can be thiophen-2-yl or thiophen-3-yl, pyridinyl (=pyridyl) can be pyridin-2-yl, pyridin-3-yl or pyridin-4-yl, imidazolyl can be, for example, 1H-imidazol-1-yl, 1H-imidazol-2-yl, 1H-imidazol-4-yl or 1H-imidazol-5-yl, quinolinyl (=quinolyl) can be quinolin-2-yl, quinolin-3-yl, quinolin-4-yl, quinolin-5-yl, quinolin-6-yl, quinolin-7-yl or quinolin-8-yl. In monosubstituted pyridin-2-yl the substituent can be located in the 3-position, 4-position, 5-position or 6-position, in monosubstituted pyridin-3-yl the substituent can be located in the 2-position, 4-position, 5-position or 6-position, in monosubstituted pyridin-4-yl the substituent can be located in the 2-position or 3-position.

As far as applicable, the preceding explanations regarding heteroaryl groups apply correspondingly to divalent heteroaryl groups, i.e. heteroarylene groups, such as the group Het in formulae I and Ia. In general, a divalent heteroaryl group can be bonded to the adjacent groups via any two desired suitable ring atoms including ring carbon atoms and/or, in the case of nitrogen heterocycles, ring nitrogen atoms. Preferably they are bonded via any two ring carbon atoms, in particular in the case of the group Het. In the case of a divalent bicyclic heteroaryl group the positions via which it is bonded to the adjacent groups can be located in the same ring or in different rings. In the case of a divalent group derived from furan or thiophene, for example, the adjacent groups can be bonded in 2,3-position, 2,4-position, 2,5-position or 3,4-position. A divalent group derived from 1,3-thiazole can be 1,3-thiazole-2,4-diyl, 1,3-thiazole-2,5-diyl or 1,3-thiazole-4,5-diyl. A divalent group derived from pyridine can be pyridine-2,3-diyl, pyridine-2,4-diyl, pyridine-2,5-diyl, pyridine-2,6-diyl, pyridine-3,4-diyl or pyridine-3,5-diyl. In the case of an unsymmetrical divalent group the present invention includes all positional isomers, i.e., in the case of a pyridine-2,5-diyl group, for example, it includes the compound in which the one adjacent group is present in the 2-position and the other adjacent group is present in the 5-position as well as the compound in which the one adjacent group is present in the 5-position and the other adjacent group is present in the 2-position. Depending on the ranking order of the adjacent groups in the nomenclature of the compound, in the name of a compound the numbers of the locations of the adjacent groups may differ from the indicated ones and, for example, a pyridine-2,5-diyl group may be designated as a pyridine-3,6-diyl group.

As far as applicable, the above explanations also apply correspondingly to the aromatic heterocycle which is formed by fusion of the group $R^3$ to the group Het in case the group X is absent. In the respective compounds of the formula Ia the resulting polycyclic heteroaromatic group, which represents the $R^3$—X-Het- moiety in formula Ia which may also be designated as $R^3$—X'-Het- moiety to distinguish it from the $R^3$—X-Het- moiety in the compounds of the formula I, is a bicyclic or tricyclic or tetracyclic ring system, preferably a bicyclic or tricyclic ring system, more preferably a bicyclic ring system, and contains one or more, for example one, two, three or four, identical or different hetero ring members chosen from N, $NR^{13}$, O and S. A phenyl or naphthalenyl or heteroaryl group representing $R^3$ can be fused to, or condensed to, the group Het via any suitable bond in $R^3$ and any suitable bond in the group Het, provided that the resulting polycyclic heteroaromatic group is known in the art to be stable and suitable as a subgroup in a drug substance and that in the resulting group at least the ring bonded to the group A can be an aromatic ring, i.e. contain six conjugated pi electrons in case of a 5-membered or 6-membered monocyclic ring. For example, if the group Het in a compound of the formula Ia is a pyridine ring, X is absent and $R^3$ is phenyl, the latter carbocyclic ring can be fused to the bond between positions 2 and 3 or the bond between positions 3 and 4 in the pyridine ring, and the resulting polycyclic heteroaromatic group representing the $R^3$—X-Het- moiety is a quinolinyl or isoquinolinyl group. If a naphthalenyl group representing $R^3$ is fused to a pyridine ring representing Het, the resulting polycyclic heteroaromatic group representing the $R^3$—X-Het- moiety is an aza-anthracenyl or aza-phenanthrenyl group. The polycyclic heteroaromatic which is present in case X is absent, can be bonded to the group A via any suitable ring atom, preferably a ring carbon atom, in an aromatic ring originating from the group Het, and can be substituted by substituents as outlined above for the individual groups $R^3$ and Het.

The heterocyclic ring which can be formed by $R^1$ and $R^2$ together with the N—CO group depicted in formulae I and Ia which carries $R^1$ and $R^2$, which ring is a lactam ring, can be 4-membered, 5-membered, 6-membered, 7-membered, 8-membered, 9-membered or 10-membered, and can be saturated, i.e. contain no double bond within the ring, or unsaturated, including partially unsaturated and aromatic, in particular partially unsaturated, and contain, for example, one, two, three or four double bonds within the ring, provided the respective ring system is known in the art to be stable and suitable as a subgroup in a drug substance. Examples of residues of heterocyclic rings formed by $R^1$ and $R^2$ together with the N—CO group, which residues are bonded to the group A via the nitrogen atom in the said N—CO group depicted in formulae I and Ia, are 2-oxo-azetidin-1-yl, 2-oxo-pyrrolidin-1-yl, 2-oxo-2,5-dihydro-1H-pyrrol-1-yl, 2-oxo-piperidin-1-yl, 2-oxo-1,2,3,4-tetrahydropyridin-1-yl, 2-oxo-1,2,5,6-tetrahydropyridin-1-yl, 2-oxo-1,2-dihydropyridin-1-yl, 2-oxo-azepan-1-yl, 2-oxo-azocan-1-yl, 2-oxo-azecan-1-yl, 2-oxo-octahydrocyclopenta[b]pyrrol-1-yl, 2-oxo-2,3-dihydro-1H-indol-1-yl, 2-oxo-octahydro-1H-indol-1-yl, 1-oxo-2,3-dihydro-1H-isoindol-2-yl, 1-oxo-octahydro-1H-isoindol-2-yl, 2-oxo-1,2-dihydroquinolin-1-yl, 2-oxo-1,2,3,4-tetrahydroquinolin-1-yl, 2-oxo-decahydroquinolin-1-yl, 1-oxo-1,2-dihydroisoquinolin-2-yl, 3-oxo-1,2,3,4-tetrahydroisoquinolin-2-yl, 1-oxo-1,2,3,4-tetrahydroisoquinolin-2-yl, 1-oxo-decahydroisoquinolin-2-yl, 3-oxo-decahydroisoquinolin-2-yl, 4-oxo-4,5,6,7-tetrahydrothieno[3,2-c]pyridin-5-yl, 6-oxo-4,5,6,7-tetrahydrothieno[3,2-c]pyridin-5-yl, 3-oxo-pyrazolidin-2-yl, 2-oxo-imidazolidin-1-yl, 5-oxo-imidazolidin-1-yl, 2-oxo-hexahydropyrimidin-1-yl, 6-oxo-hexahydropyrimidin-1-yl, 2-oxo-1,2-dihydropyrimidin-1-yl, 2-oxo-piperazin-1-yl, 2-oxo-[1,3]diazepan-1-yl, 7-oxo-[1,3]diazepan-1-yl, 2-oxo-[1,4]diazepan-1-yl, 7-oxo-[1,4]diazepan-1-yl, 2-oxo-oxazolidin-3-yl, 2-oxo-[1,3]oxazinan-3-yl, 2-oxo-[1,3]oxazepan-3-yl, 3-oxo-morpholin-4-yl, 3-oxo-[1,4]oxazepan-4-yl, 5-oxo-[1,4]oxazepan-4-yl, 2-oxo-thiazolidin-3-yl, 2-oxo-[1,3]thiazinan-3-yl, 3-oxo-thiomorpholin-4-yl, 3-oxo-3,4-dihydro-2H-[1,4]thiazin-4-yl, 2-oxo-[1,3]thiazepan-3-yl, 3-oxo-[1,4]thiazepan-4-yl, 5-oxo-[1,4]thiazepan-4-yl. As applies to the ring which can be formed by $R^1$ and $R^2$ together with the N—CO group in general, all listed examples of heterocyclic groups can be unsubstituted or substituted as indicated above, for example by $R^8$. For example, they can be substituted on one or more, for example one, two or three, preferably one or two, more preferably one, ring carbon atoms by further oxo groups in addition to the oxo group mentioned in the listed names, and/or by one or more, for example one, two, three or four, preferably one or two, identical or different alkyl groups such as methyl groups, and/or on one or more ring nitrogen atom by a $(C_1-C_4)$-alkyl group or a $(C_1-C_4)$-alkyl-CO— group such as methyl or acetyl which group represents $R^{12}$. Examples of groups listed above which are substituted by a further oxo group include 2,5-dioxo-pyrrolidin-1-yl, 2,6-dioxo-piperidin-1-yl, 2,5-dioxo-imidazolidin-1-yl, 2,6-dioxo-hexahydropyrimidin-1-yl, 1,3-dioxo-2,3-dihydro-1H-isoindol-2-yl (=1,3-dioxo-isoindol-2-yl) and 2,4-dioxo-thiazolidin-3-yl. Furthermore, as applies to the ring which can be formed by $R^1$ and $R^2$ together with the N—CO group in general, ring sulfur atoms in the listed heterocyclic groups can carry one or two oxo groups, i.e. doubly bonded oxygen atoms, and thus become SO or $SO_2$ groups, i.e. sulfoxide or sulfone groups or S-oxides or S,S-dioxides. For example, the sulfur atom in a 3-oxo-thiomorpholin-4-yl group can carry one or two oxo groups, and besides the 3-oxo-thiomorpholin-4-yl group also the groups 1,3-dioxo-thiomorpholin-4-yl and 1,1,3-trioxo-thiomorpholin-4-yl can be present in a compound of the invention.

Halogen is fluorine, chlorine, bromine or iodine, preferably fluorine, chlorine or bromine, more preferably fluorine or chlorine.

An oxo group, when bonded to a carbon atom, replaces two hydrogen atoms on a carbon atom of the parent system. Thus, if a $CH_2$ group is substituted by oxo, i.e. by a doubly bonded oxygen atom, it becomes a CO group. Evidently, an oxo group cannot occur as a substituent on a carbon atom in an aromatic ring.

The present invention includes all stereoisomeric forms of the compounds of the formulae I and Ia and their salts. With respect to each chiral center, independently of any other chiral center, the compounds of formulae I and Ia can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings, including the double bond in the group —CH=CH—$CH_2$— and the cycloalkane rings in the groups of the formulae II and III representing the group A or present therein, the invention includes both the E form and Z form, or the cis form and the trans form, as well as mixtures of these forms in all ratios. In a preferred embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally a derivatization can be carried out before a separation of stereoisomers. The separation of a mixture of stereoisomers can be carried out at the stage of the compound of the formula I or Ia or at the stage of a starting material or an intermediate during the synthesis. The present invention also includes all tautomeric forms of the compounds of formulae I and Ia and their salts.

In case the compounds of the formulae I and Ia contain one or more acidic and/or basic groups, i.e. salt-forming groups, the invention also comprises their corresponding physiologically or toxicologically acceptable salts, i.e. non-toxic salts, in particular their pharmaceutically acceptable salts. Thus, the compounds of the formulae I and Ia which contain an acidic group can be present on such groups, and can be used according to the invention, for example, as alkali metal salts, alkaline earth metal salts or as ammonium salts. More specific examples of such salts include sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formulae I and Ia which contain a basic group, i.e. a group which can be protonated, can be present on such groups, and can be used according to the invention, for example, in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, nicotinic acid, isonicotinic acid, citric acid, adipic acid, and other acids known to the person skilled in the art. If the compounds of the formulae I and Ia simultaneously contain acidic and basic groups in the molecule, the invention also includes, in addition to the salt forms mentioned, inner salts or betaines or zwitterions. The salts of the compounds of the formulae I and Ia can be obtained by customary methods which are known to the person skilled in the art like, for example, by contacting the compound of the formula I or Ia with an organic or inorganic acid or base in a solvent or diluent, or by anion exchange or cation exchange from another salt. The present invention also includes all salts of the compounds of the formula I which, owing to low physiological compatibility, are not directly suitable for use in pharmaceuticals but which can be used, for example, as intermediates for chemical reactions or for the preparation of physiologically acceptable salts.

The present invention furthermore includes all solvates of compounds of the formulae I and Ia, for example hydrates or adducts with alcohols, active metabolites of the compounds of the formulae I and Ia, and also prodrugs and derivatives of the compounds of the formulae I and Ia which in vitro may not necessarily exhibit pharmacological activity but which in vivo are converted into pharmacologically active compounds, for example esters or amides of carboxylic acid groups.

The group A in the compounds of the formulae I and Ia is preferably chosen from —CH=CH—CH$_2$—, —C≡C—CH$_2$—, which groups are bonded to the group Het via the terminal atom of the double or triple bond, and the group of the formula II, which is bonded to the group Het via a ring atom,

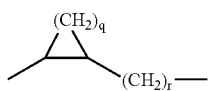

II wherein in the formula II the bonds via which the group is connected to the adjacent groups, are depicted by the lines starting at a ring atom and at the group (CH$_2$)$_r$, and wherein all groups A can be substituted by one or more identical or different substituents R$^4$. More preferably the group A in the compounds of the formulae I and Ia is chosen from —C≡C—CH$_2$—, which group is bonded to the group Het via the terminal atom of the triple bond, and the group of the formula II, which is bonded to the group Het via a ring atom, wherein in the formula II the bonds via which the group is connected to the adjacent groups, are depicted by the lines starting at a ring atom and at the group (CH$_2$)$_r$, and wherein all groups A can be substituted by one or more identical or different substituents R$^4$. Particularly preferably the group A in the compounds of the formulae I and Ia is the group of the formula II, which is bonded to the group Het via a ring atom, wherein in the formula II the bonds via which the group is connected to the adjacent groups, are depicted by the lines starting at a ring atom and at the group (CH$_2$)$_r$, and wherein the group of the formula II can be substituted by one or more identical or different substituents R$^4$. In one embodiment of the invention the group A is chosen from —CH=CH—CH$_2$— and —C≡C—CH$_2$—, which groups are bonded to the group Het via the terminal atom of the double or triple bond and which can be substituted by one or more identical or different substituents R$^4$. In another embodiment of the invention the group A is chosen from the group of the formula II, which is bonded to the group Het via a ring atom, and the group of the formula III, wherein in the formulae II and III the bonds via which the groups are connected to the adjacent groups, are depicted by the lines starting at ring atoms and at the group (CH$_2$)$_r$, and wherein the groups of the formulae II and III can be substituted by one or more identical or different substituents R$^4$.

The number q in the group of the formula II preferably is 1, 2 or 3, more preferably 1 or 2. In one embodiment of the invention the number q is 1, 3 or 4. In another embodiment of the invention the number q is 1 and the resulting group of the formula II representing the group A in formulae I and Ia thus is a group of the formula IIa comprising a cyclopropane ring,

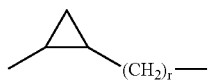

IIa

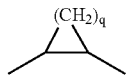

IIb

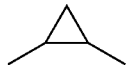

IIc which is bonded to the group Het via a ring atom, and wherein the bonds via which the group is connected to the adjacent groups, are depicted by the lines starting at a ring atom and at the group (CH$_2$)$_r$, and wherein the group of the formula IIa can be substituted by one or more identical or different substituents R$^4$. The number r occurring in the formulae II and IIa preferably is zero, and the resulting groups of the formulae II or IIa, i.e. the groups of the formulae IIb and IIc which represent the group A, are directly bonded to the group NR$^2$ via a single bond. In the formulae IIb and IIc the bonds via which the groups are connected to the adjacent groups, are depicted by the lines starting at ring atoms. The groups of the formulae IIb and IIc can be substituted by one or more identical or different substituents R$^4$. In one embodiment of the invention the group A in the compounds of the formulae I and Ia is the group IIc wherein the bonds via which the group is connected to the adjacent groups are depicted by the lines starting at ring atoms and which can be substituted by one or more identical or different substituents R$^4$. In another embodiment of the invention the group A is the group of the formula IIb. The number s occurring in the formula III preferably is 1 or 2, more preferably 1. In one embodiment of the invention the number s is 2 or 3. In one embodiment of the invention the group A is unsubstituted, i.e. is not substituted by substituents R$^4$. In another embodiment of the invention the groups R$^3$—X-Het- and —CH$_2$—N(R$^2$)—CO—R$^1$ bonded to the —CH=CH— moiety in the group —CH=CH—CH$_2$— representing the group A are present in E-position (=trans-position) with respect to each other. In a further embodiment of the invention the groups R$^3$—X-Het- and —CH$_2$—N(R$^2$)—CO—R$^1$, or the groups R$^3$—X-Het- and —N(R$^2$)—CO—R$^1$ in case the number r is zero, which are bonded to the cycloalkane ring in the groups of the formulae II, IIa, IIb, IIc representing the group A, are present in E-position (=trans-position) with respect to each other. In a further embodiment of the invention the groups $R^3$—X-Het- and —N($R^2$)—CO—$R^1$ bonded to the cycloalkane ring in the group of the formula III representing the group A are present in E-position (=trans-position) with respect to each other.

In the compounds of the formula Ia the divalent group Het is preferably defined as in compounds of the formula I. I.e., one embodiment of the present invention relates to the use of a compound of the formula I, which is defined as indicated above, in any of its stereoisomeric forms or a mixture of stereoisomeric forms in any ratio, or a physiologically acceptable salt thereof, for the manufacture of a medicament for the stimulation of the expression of endothelial NO synthase and for the treatment of a disease in which such a stimulation, or an increase in NO level, is desired, for example a cardiovascular disorder such as atherosclerosis, coronary artery disease or cardiac insufficiency or any other diseases mentioned above or below herein.

More preferably, the divalent group Het in the compounds of the formulae I and Ia is a divalent aromatic group of the formula IV

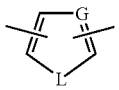

IV in which G is chosen from N and CH and L is chosen from S, O, $NR^{13}$, CH=CH, CH=N and N=CH, and which can be substituted by one or more identical or different substituents $R^5$, i.e. in which one or more ring carbon atoms can carry a substituent $R^5$ instead of the hydrogen atoms which are present on the carbon atoms depicted in formula IV or which are specified in the definition of the groups G and L, with the proviso that the ring system depicted in formula IV comprises at least one hetero ring member, i.e. a group $NR^{13}$ or an N, S or O atom, as a ring member. $R^5$ and $R^{13}$ in the ring system of the formula IV are defined as indicated above with respect to the compounds of the formulae I and Ia. Particularly preferably the group Het in the compounds of the formulae I and Ia and the group of the formula IV is chosen from the heteroarylene groups pyridinediyl, thiazolediyl, oxazolediyl, imidazolediyl and thiophenediyl, i.e. the divalent residues of pyridine, thiazole, oxazole, imidazole and thiophene, which can all be substituted by one or more identical or different substituents $R^5$ and wherein one of the ring nitrogen atoms of the imidazolediyl group, which represents the nitrogen atom in the group $NR^{13}$ in the definition of the group L, carries a group chosen from hydrogen and ($C_1$-$C_4$)-alkyl. More particularly preferably the group Het in the compounds of the formulae I and Ia and the group of the formula IV is chosen from the heteroarylene groups pyridinediyl, thiazolediyl, imidazolediyl and thiophenediyl, especially preferably from pyridinediyl and thiazolediyl, which can all be substituted by one or more identical or different substituents $R^5$ and wherein one of the ring nitrogen atoms of the imidazolediyl group, which represents the nitrogen atom in the group $NR^{13}$ in the definition of the group L, carries a group chosen from hydrogen and ($C_1$-$C_4$)-alkyl. In one embodiment of the invention the group Het in the compounds of the formulae I and Ia and the group of the formula IV is a pyridinediyl group which can be substituted by one or more identical or different substituents $R^5$.

The preferred groups representing the group Het in the compounds of the formulae I and Ia, including the group of the formula IV in which the bonds via which it is connected to the two adjacent groups $R^3$—X and A are represented by the lines intersecting the ring sides, can be bonded to the adjacent groups $R^3$—X and A via any two ring carbon atoms. Preferably a pyridinediyl group representing Het or the group of the formula IV is bonded to the adjacent groups via positions 3 and 6 of the pyridine ring, which positions may also be numbered as positions 5 and 2, respectively, depending on the ranking order of the groups bonded to the pyridine ring, where each of the groups $R^3$—X and A can be present in each of the positions. I.e., in the said pyridinediyl group, which is bonded via positions 3 and 6, the group $R^3$—X can be present in position 3 and the group A in position 6, as well as the group $R^3$—X can be present in position 6 and the group A in position 3, and preferably the group $R^3$—X is present in position 6 and the group A in position 3.

Preferably a group of the formula IVa,

IVa which represents Het or the group of the formula IV and in which L is O, S or $NR^{13}$, i.e. which is a oxazolediyl, thiazolediyl or imidazolediyl group, is bonded to the adjacent groups via positions 2 and 5 or via positions 2 and 4, particularly preferably via positions 2 and 4, where each of the groups $R^3$—X and A can be present in each of the positions and preferably the group $R^3$—X is present in position 4 and the group A in position 2.

Preferably a thiophenediyl group which represents Het or the group of the formula IV is bonded to the adjacent groups via positions 2 and 5 or via positions 2 and 4, which latter positions may also be numbered as positions 5 and 3, particularly preferably via positions 2 and 4, where each of the groups $R^3$—X and A can be present in each of the positions and preferably the group $R^3$—X is present in position 4 and the group A in position 2.

Preferred groups Het or groups of the formula IV thus include the divalent heteroaromatic groups depicted in the following formulae Va to Vg which represent preferred embodiments of the structural moiety $R^3$—X-Het-A- in the compounds of the formulae I and Ia, and in which the heteroaromatic group can be unsubstituted or substituted by one or more identical or different substituents $R^5$.

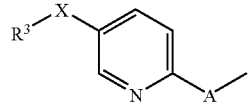

Va

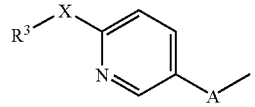

Vb

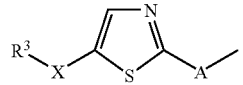

Vc

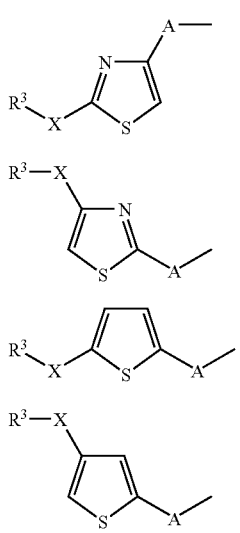

Particularly preferred groups Het or groups of the formula IV include the divalent heteroaromatic groups depicted in the formulae Vb, Ve and Vg, especially the group depicted in formula Vb, which represent particularly and especially preferred embodiments of the structural moiety $R^3$—X-Het-A- in the compounds of the formulae I and Ia.

In the compounds of the formula Ia the group X is preferably chosen from a direct bond, $CH_2$, O and NH, or X is absent and in this case the phenyl or heteroaryl group representing the group $R^3$ is fused to the group Het. Particularly preferably the group X in the compounds of the formulae I and/or Ia is chosen from a direct bond and O, or in the compounds of the formula Ia the group X is absent, and more particularly preferably the group X in the compounds of the formulae I and/or Ia is chosen from a direct bond and O. In one embodiment of the present invention the group X in the compounds of the formulae I and/or Ia is a direct bond. In another embodiment of the present invention the group X in the compounds of the formula Ia is absent and in this embodiment the phenyl, naphthalenyl or heteroaryl group representing the group $R^3$ is fused to the group Het. In a further embodiment of the present invention the group X in the compounds of the formula Ia cannot be absent, i.e. in this embodiment the group X in the compounds of the formula Ia is chosen from a direct bond, $CH_2$, O, S, NH and $N((C_1-C_4)$-alkyl). In all cases in which X is absent the phenyl, naphthalenyl or heteroaryl group representing the group $R^3$ is fused to the group Het or the ring system depicted in formula IV which contains the groups G and L. In case X can be absent, in a particularly preferred embodiment of the present invention the structural moiety $R^3$—X-Het- in the compounds of the formulae I and Ia is a bicyclic heteroaryl groups which comprises a monocyclic 5-membered or 6-membered heteroaromatic ring which represents the group Het and to which the group A is bonded, and a benzene ring which is fused to said heteroaromatic ring system and which represents the group $R^3$, where the heteroaromatic ring can be substituted by one or more identical or different substituents $R^5$ and the benzene ring can be substituted as indicated above with respect to $R^3$. In case X is absent, the said structural moiety $R^3$—X-Het- is more particularly preferably chosen from quinolinyl, isoquinolinyl, benzoimidazolyl, benzothiazolyl and benzothienyl, especially preferably from quinolinyl, benzoimidazolyl and benzothiazolyl, which are all bonded to the group A via the heterocyclic ring and which can be substituted as indicated.

If the ring which can be formed by the groups $R^1$ and $R^2$ together with the N—CO group which carries them is a monocyclic ring system, it is preferably saturated or partially unsaturated, and more preferably it is saturated or contains one or two double bonds within the ring, and particularly preferably it is saturated or contains one double bond within the ring, and especially preferably it is saturated. If the said ring is a bicyclic ring system, the specific ring of the ring system to which the group A is bonded is preferably saturated or is partially unsaturated, and more preferably it contains one or two double bonds within the ring one of which can be common to both rings, and the second ring of the ring system preferably is a saturated or an aromatic ring, more preferably an aromatic ring such as a benzene ring. Preferably, a monocyclic ring formed by the groups $R^1$ and $R^2$ together with the N—CO which carries them contains 4, 5, 6 or 7 ring members and a bicyclic ring system contains 9 or 10 ring members. The ring which can be formed by the groups $R^1$ and $R^2$ together with the N—CO group is preferably a monocyclic ring system. In addition to the ring nitrogen atom being part of the N—CO group, the ring which can be formed by the groups $R^1$ and $R^2$ together with the N—CO group which carries them can preferably contain one further hetero ring member, i.e. a ring heteroatom or a heteroatom group, which is chosen from N, $NR^{12}$, O, S, SO and $SO_2$ and preferably is chosen from $NR^{12}$, S, SO and $SO_2$ and more preferably is chosen from $NR^{12}$ and S. If the heterocycle formed by $R^1$ and $R^2$ and the N—CO group which carries them is substituted by one or more identical or different substituents $R^8$, it preferably is substituted by one, two, three, four or five, more preferably by one, two, three or four, particularly preferably by one, two or three, more particularly preferably by one or two identical or different substituents $R^8$ on ring carbon atoms, in addition to the oxo group depicted in formulae I and Ia and/or to oxo groups on ring sulfur atoms and/or groups $R^{12}$ on ring nitrogen atoms which may be present.

If $R^1$ and $R^2$, together with the N—CO group depicted in formulae I and Ia which carries them, form a ring, they preferably form a saturated or unsaturated, monocyclic 4-membered to 7-membered ring, for example a 5-membered or 6-membered ring, which, in addition to the ring nitrogen atom being part of the N—CO group, can contain one further hetero ring member group chosen from N, $NR^{12}$, O, S, SO and $SO_2$, wherein the ring formed by $R^1$ and $R^2$ and the N—CO group which carries them can be substituted by one or more identical or different substituents $R^8$. Further hetero ring members which are present in a ring formed by $R^1$ and $R^2$ together with the N—CO group which carries them are preferably chosen from $NR^{12}$, O and S, more preferably from $NR^{12}$ and S. Particularly preferably, a further hetero ring member is the group $NR^{12}$. The group —$N(R^2)$—CO—$R^1$ in the formulae I and Ia which results if $R^1$ and $R^2$ together with the N—CO group which carries them form a ring, is more preferably chosen from 2-oxo-azetidin-1-yl, 2-oxo-pyrrolidin-1-yl, 2-oxo-piperidin-1-yl, 2-oxo-1,2-dihydropyridin-1-yl, 2-oxo-azepan-1-yl, 2-oxo-imidazolidin-1-yl, 2-oxo-hexahydropyrimidin-1-yl, 2-oxo-1,2-dihydropyrimidin-1-yl, 2-oxo-piperazin-1-yl, 2-oxo-[1,3]diazepan-1-yl, 2-oxo-[1,4]diazepan-1-yl, 7-oxo-[1,4]diazepan-1-yl, 2-oxo-oxazolidin-3-yl, 2-oxo-[1,3]oxazinan-3-yl, 2-oxo-[1,3]oxazepan-3-yl, 3-oxo-morpholin-4-yl, 3-oxo-[1,4]oxazepan-4-yl, 5-oxo-[1,4]oxazepan-4-yl, 2-oxo-thiazolidin-3-yl, 2-oxo-[1,3]thiazinan-3-yl, 3-oxo-thiomorpholin-4-yl, 3-oxo-3,4-dihydro-2H-[1,4]thiazin-4-yl, 2-oxo-[1,3]thiazepan-3-yl, 3-oxo-[1,4]

thiazepan-4-yl and 5-oxo-[1,4]thiazepan-4-yl, i.e. from the groups depicted in the following formulae

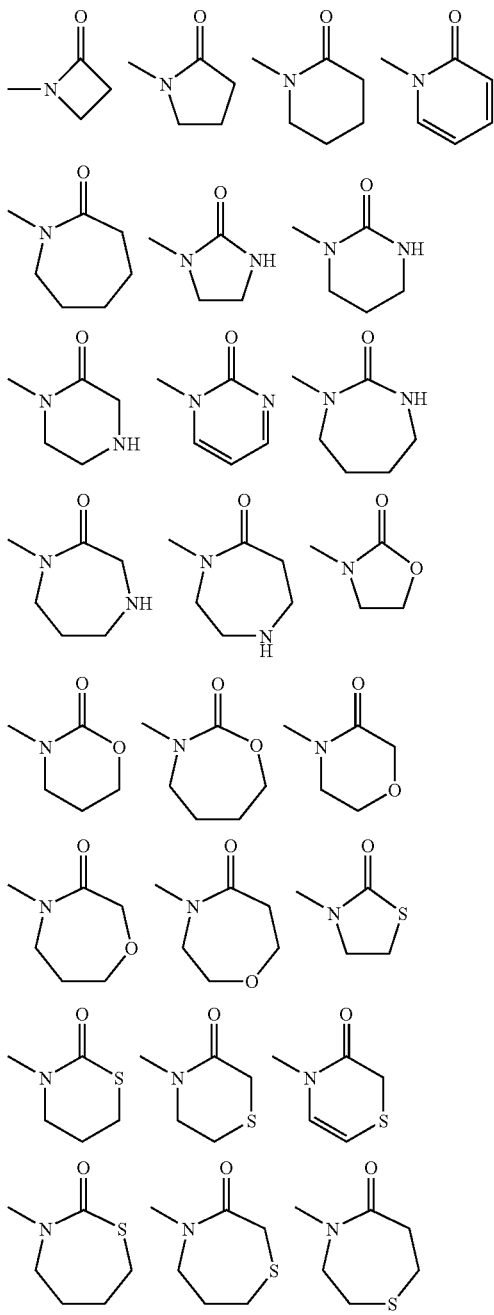

in which the bond via which the group is connected to the group A is depicted by a line starting at a ring nitrogen atom. Particularly preferably the group which results if $R^1$ and $R^2$ together with the N—CO group which carries them form a ring, is chosen from 2-oxo-azetidin-1-yl, 2-oxo-pyrrolidin-1-yl, 2-oxo-piperidin-1-yl, 2-oxo-1,2-dihydropyridin-1-yl, 2-oxo-azepan-1-yl, 2-oxo-imidazolidin-1-yl, 2-oxo-hexahydropyrimidin-1-yl, 2-oxo-[1,3]diazepan-1-yl, 2-oxo-thiazolidin-3-yl, 3-oxo-thiomorpholin-4-yl, 3-oxo-3,4-dihydro-2H-[1,4]thiazin-4-yl, i.e. from the groups depicted in the following formulae.

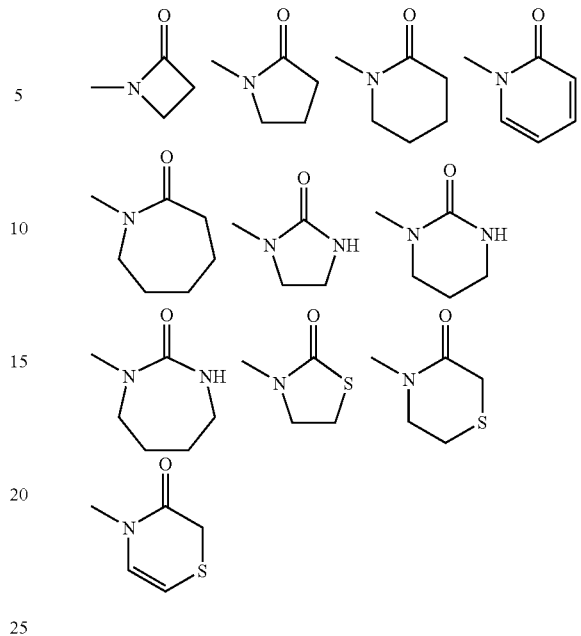

All the specified rings formed by $R^1$ and $R^2$ together with the N—CO group which carries them can be substituted on carbon atoms by one or more identical or different substituents $R^8$, and/or can carry on a ring nitrogen atom which is not bonded to the group A a group $R^{12}$, and/or can carry on a ring sulfur atom one or two oxo groups, to give a substituted group as indicated above. As examples of such groups which are substituted by an oxo group on a carbon atom or by one or two oxo groups on a sulfur atom, and which represent the group —N($R^2$)—CO—$R^1$ in the formulae I and Ia and in which the bond via which the group is connected to the group A is depicted by a line starting at a ring nitrogen atom, the groups 2,5-dioxo-pyrrolidin-1-yl, 2,6-dioxo-piperidin-1-yl, 2,5-dioxo-imidazolidin-1-yl, 2,6-dioxo-hexahydropyrimidin-1-yl, 2,4-dioxo-thiazolidin-3-yl, 1,3-dioxo-thiomorpholin-4-yl and 1,1,3-trioxo-thiomorpholin-4-yl may be mentioned, i.e. groups of the following formulae,

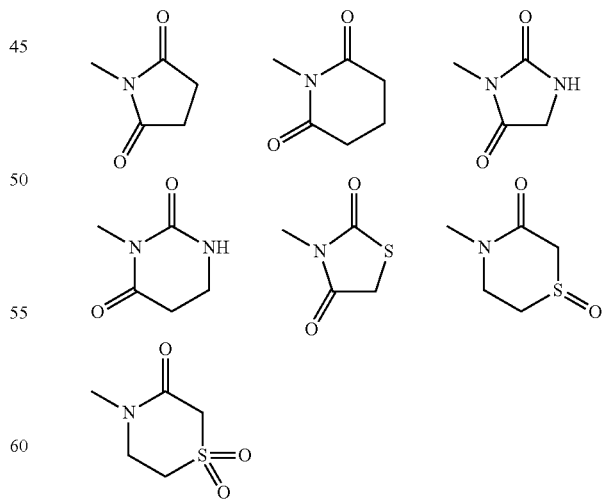

which can all be substituted additionally on carbon atoms by one or more identical or different substituents $R^8$ and/or can carry on a ring nitrogen atoms which is not bonded to the group A a group $R^{12}$.

If $R^1$ and $R^2$ do not form a ring together with the N—CO group which carries them, they preferably are independently of each other chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, more preferably from $(C_1-C_4)$-alkyl, $(C_3-C_7)$-cycloalkyl-, phenyl, phenyl-$CH_2$—, heteroaryl and heteroaryl-$CH_2$—, particularly preferably from $(C_1-C_4)$-alkyl, $(C_3-C_7)$-cycloalkyl-, phenyl- and heteroaryl-, and in each case $R^2$ can in addition be hydrogen, wherein the groups $(C_1-C_4)$-alkyl and $(C_3-C_7)$-cycloalkyl can both be substituted by one or more identical or different substituents $R^6$, and the groups phenyl and heteroaryl can both be substituted by one or more identical or different substituents $R^7$. If $R^1$ and $R^2$ do not form a ring together with the N—CO group which carries them, in one embodiment of the present invention $R^2$ is hydrogen and $R^1$ is defined as indicated. If $R^2$ is an alkenyl group or an alkynyl group, preferably the nitrogen atom carrying $R^2$ is not in conjugation with a double bond or triple bond, i.e., preferably the nitrogen atom carrying $R^2$ is not directly bonded to a carbon atom in an alkenyl group or alkynyl group which is part of a double bond or triple bond.

In the compounds of the formula Ia the groups $R^1$ and $R^2$ preferably are independently of each other chosen from $(C_1-C_6)$-alkyl, $(C_3-C_6)$-alkenyl, $(C_3-C_6)$-alkynyl, $(C_3-C_7)$-cycloalkyl-$C_nH_{2n}$—, phenyl-$C_nH_{2n}$— and heteroaryl-$C_nH_{2n}$—, and $R^2$ can in addition be hydrogen, wherein the groups $(C_1-C_6)$-alkyl, $(C_3-C_7)$-cycloalkyl, $(C_3-C_6)$-alkenyl and $(C_3-C_6)$-alkynyl can all be substituted by one or more identical or different substituents $R^6$, and the groups $C_nH_{2n}$ can all be substituted by one or more identical or different substituents chosen from fluorine and $(C_1-C_4)$-alkyl, and all phenyl groups and heteroaryl groups can be substituted by one or more identical or different substituents $R^7$,
or $R^1$ and $R^2$, together with the N—CO group which carries them, form a 4-membered to 10-membered, monocyclic or bicyclic, saturated or unsaturated ring which, in addition to the ring nitrogen atom being part of the N—CO group, can contain one or two further hetero ring members or heteroatom groups chosen from N, $NR^{12}$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the N—CO group which carries them can be substituted by one or more identical or different substituents $R^8$.

Particularly preferably, in the compounds of the formulae I and Ia the groups $R^1$ and $R^2$ are chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and $R^2$ can in addition be hydrogen, wherein the groups $(C_1-C_4)$-alkyl and $(C_3-C_7)$-cycloalkyl can both be substituted by one or more identical or different substituents $R^6$, and all phenyl groups and heteroaryl groups can be substituted by one or more identical or different substituents $R^7$,
or $R^1$ and $R^2$, together with the N—CO group which carries them, form a 4-membered 5 to 7-membered, monocyclic, saturated or unsaturated ring which, in addition to the ring nitrogen atom being part of the N—CO group, can contain one further hetero ring member chosen from N, $NR^{12}$, O, S, SO and $SO_2$, wherein the ring formed by $R^1$ and $R^2$ and the N—CO group which carries them can be substituted by one or more identical or different substituents $R^8$.

In one embodiment of the present invention $R^1$ and $R^2$, together with the N—CO group which carries them, form a 4-membered to 10-membered, monocyclic or bicyclic, saturated or unsaturated ring which, in addition to the ring nitrogen atom being part of the N—CO group, can contain one or two further hetero ring members chosen from N, $NR^{12}$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the N—CO group which carries them can be substituted by one or more identical or different substituents $R^8$, and wherein preferred features of this embodiment are those outlined above. For example, in a preferred feature of this embodiment the ring formed by $R^1$ and $R^2$ together with the N—CO group which carries them is a saturated or unsaturated, monocyclic 4-membered to 7-membered ring, for example a 5-membered or 6-membered ring, which, in addition to the ring nitrogen atom being part of the N—CO group, can contain one further hetero ring member group which is preferably chosen from $NR^{12}$, O and S, more preferably from $NR^{12}$ and S, and particularly preferably is a group $NR^{12}$, and which can be substituted by an oxo group on a carbon atom.

In the compounds of the formula Ia the group $R^3$ is preferably chosen from phenyl, naphthalenyl and heteroaryl which can all be substituted by one or more identical or different substituents chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—. Particularly preferably the group $R^3$ in the compounds of the formulae I and Ia is chosen from phenyl, naphthalenyl and heteroaryl, and preferably is a phenyl group or heteroaryl group and more preferably is a phenyl group, which groups can all be substituted by one or more identical or different substituents which are chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—. Preferably the optional substituents on the group $R^3$ are chosen from halogen, $(C_1-C_4)$-alkyl, $(C_1-C_4)$-alkyloxy which can be substituted by one or more fluorine atoms, and $CF_3$, more preferably from halogen and $(C_1-C_4)$-alkyl. Particularly preferably $R^3$ is a phenyl group which can be substituted by one or more identical or different substituents which are chosen from halogen, $(C_1-C_4)$-alkyl and $CF_3$. Especially preferably $R^3$ is a phenyl group which is substituted by one or more identical or different substituents chosen from halogen atoms and $(C_1-C_4)$-alkyl groups, in particular from fluorine atoms, chlorine atoms, methyl groups and ethyl groups. A phenyl group representing $R^3$ is preferably a substituted phenyl group. In a substituted group $R^3$ the number of substituents preferably is one, two, three, four or five, more preferably one, two, three or four, particularly preferably one, two or three, more particularly preferably one or two. In one embodiment of the present invention the group $R^3$ is a carbocyclic group, i.e. a phenyl group or a naphthalenyl group, and in another embodiment of the invention the group $R^3$ is a monocyclic group, i.e. a phenyl group or a monocyclic heteroaryl group, for example a thienyl group, and in another embodiment of the invention $R^3$ is a phenyl group, a naphthalenyl group or a monocyclic heteroaryl group, for example a thienyl group, where all these groups can be substituted as indicated.

In the compounds of the formula Ia the group $R^4$ is preferably chosen from $(C_1-C_4)$-alkyl, fluorine and oxo, more preferably from $(C_1-C_4)$-alkyl and fluorine. Halogen atoms representing $R^4$ in the compounds of the formula Ia are preferably chosen from fluorine and chlorine. When two halogen atoms representing $R^4$ are present in a compound of the formula Ia, among others they can be present in vicinal position with respect to each other. Particularly preferably the group $R^4$ in the compounds of the formulae I and Ia is chosen from methyl and fluorine, and especially preferably $R^4$ is fluorine. The total number of substituents $R^4$ in a substituted group A, which can be one, two, three, four, five or six, for example, is preferably one, two, three or four, more preferably one or two.

In the compounds of the formula Ia the group $R^5$ is preferably chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$ and $(C_1-C_4)$-alkyl-$SO_2$—. Particularly preferably the group $R^5$ in the compounds of the formulae I and Ia is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—, more particularly preferably from halogen, $(C_1-C_4)$-alkyl and $CF_3$. Especially preferably the group Het in the compounds of the formulae I and Ia is unsubstituted or substituted by one or more identical or different substituents chosen from fluorine, chlorine, methyl and $CF_3$, in particular fluorine, chlorine and methyl, for example fluorine substituents, and more especially preferably the group Het is unsubstituted. The number of substituents $R^5$, which are present on a substituted group Het, preferably is one, two, three or four, more preferably one, two or three, particularly preferably one or two, more particularly preferably one.

In the compounds of the formula Ia the group $R^6$ is preferably chosen from fluorine, OH, oxo, $(C_1-C_4)$-alkyloxy, $(C_1-C_4)$-alkylmercapto, di$((C_1-C_4)$-alkyl)amino, $((C_1-C_4)$-alkyl)-CONH—, di$((C_1-C_4)$-alkyl)aminocarbonyl-, $((C_1-C_4)$-alkyloxy)carbonyl-, COOH, $CONH_2$, CN and $CF_3$. Particularly preferably the group $R^6$ in the compounds of the formulae I and Ia is chosen from fluorine, $(C_1-C_4)$-alkyloxy, di$((C_1-C_4)$-alkyl)amino, $((C_1-C_4)$-alkyl)-CONH—, di$((C_1-C_4)$-alkyl)aminocarbonyl-, $((C_1-C_4)$-alkyloxy)carbonyl-, COOH and $CF_3$, more particularly preferably from fluorine, $((C_1-C_4)$-alkyloxy)carbonyl- and COOH, especially preferably from $((C_1-C_4)$-alkyloxy)carbonyl- and COOH. The number of substituents $R^6$ preferably is one, two or three, more preferably one or two, particularly preferably one.

In the compounds of the formula Ia the group $R^7$ is preferably chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—. Particularly preferably the group $R^7$ in the compounds of the formulae I and Ia is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—, more particularly preferably from halogen, $(C_1-C_4)$-alkyl, $NH_2$, $(C_1-C_4)$-alkylamino, di$((C_1-C_4)$-alkyl)amino, $((C_1-C_4)$-alkyl)-CONH— and $CF_3$, especially preferably from fluorine, chlorine, methyl, $NH_2$ and $CF_3$. The number of substituents $R^7$ preferably is one, two, three or four, more preferably one, two or three, particularly preferably one or two, more particularly preferably one.

In the compounds of the formula Ia the group $R^8$ is preferably chosen from halogen, $(C_1-C_4)$-alkyl, $(C_3-C_7)$-cycloalkyl-$C_nH_{2n}$—, phenyl-$C_nH_{2n}$—, heteroaryl-$C_nH_{2n}$—, $(C_1-C_4)$-alkyloxy-$(C_1-C_2)$-alkyl-, OH, oxo, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy. Particularly preferably the group $R^3$ in the compounds of the formulae I and Ia is chosen from halogen, $(C_1-C_4)$-alkyl, phenyl-$C_nH_{2n}$—, heteroaryl-$C_nH_{2n}$—, $(C_1-C_4)$-alkyloxy-$(C_1-C_2)$-alkyl-, OH, oxo, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyloxy)carbonyl-, $CONH_2$, CN and $CF_3$, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy. More particularly preferably the group $R^8$ in the compounds of the formulae I and Ia is chosen from halogen, $(C_1-C_4)$-alkyl, $(C_1-C_4)$-alkyloxy-$(C_1-C_2)$-alkyl-, oxo, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $((C_1-C_4)$-alkyl)-CONH—, di$((C_1-C_4)$-alkyl)aminocarbonyl- and $CF_3$, especially preferably from halogen, $(C_1-C_4)$-alkyl, oxo, $(C_1-C_4)$-alkyloxy which can be substituted by one or more fluorine atoms, and $CF_3$, more especially preferably from halogen, $(C_1-C_4)$-alkyl, oxo and $CF_3$. Substituents $R^8$ which are present in a non-aromatic ring in the heterocycle formed by $R^1$ and $R^2$ together with the N—CO group which carries them, in particular in the ring which contains the said N—CO group, for example in a non-aromatic monocyclic heterocycle formed by $R^1$ and $R^2$ together with the N—CO group, are preferably chosen from $(C_1-C_4)$-alkyl, $(C_3-C_7)$-cycloalkyl-$C_nH_{2n}$—, phenyl-$C_nH_{2n}$—, heteroaryl-$C_nH_{2n}$—, $(C_1-C_4)$-alkyloxy-$(C_1-C_2)$-alkyl-, OH, oxo, $NH_2$, $(C_1-C_4)$-alkylamino, di$((C_1-C_4)$-alkyl)amino and $((C_1-C_4)$-alkyl)-CONH—, more preferably from $(C_1-C_4)$-alkyl, $(C_3-C_7)$-cycloalkyl-$C_nH_{2n}$—, phenyl-$C_nH_{2n}$—, heteroaryl-$C_nH_{2n}$— and oxo, particularly preferably from $(C_1-C_4)$-alkyl and oxo, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy. The number of substituents $R^8$ preferably is one, two, three, four or five, more preferably one, two, three or four, particularly preferably one, two or three, more particularly preferably one or two.

In the compounds of the formula Ia the group $R^{12}$ is preferably chosen from hydrogen, $(C_1-C_4)$-alkyl, $(C_3-C_7)$-cycloalkyl-$C_nH_{2n}$—, phenyl-$C_nH_{2n}$—, heteroaryl-$C_nH_{2n}$—, $((C_1-C_4)$-alkyl)-CO—, $(C_3-C_7)$-cycloalkyl-$C_nH_{2n}$—CO—, phenyl-$C_nH_{2n}$—CO—, heteroaryl-$C_nH_{2n}$—CO—, $((C_1-C_4)$-alkyl)-O—CO— and phenyl-$C_nH_{2n}$—O—CO—, wherein all phenyl groups and heteroaryl groups can be substituted by one or more identical or different substituents chosen from halogen, $(C_1-C_4)$-alkyl, $CF_3$ and $(C_1-C_4)$-alkyloxy. Particularly preferably the group $R^{12}$ in the compounds of the formulae I and Ia is chosen from hydrogen, $(C_1-C_4)$-alkyl, $(C_3-C_7)$-cycloalkyl-$C_nH_{2n}$—, $((C_1-C_4)$-alkyl)-CO—, $(C_3-C_7)$-cycloalkyl-$C_nH_{2n}$—CO—, $((C_1-C_4)$-alkyl)-O—CO— and phenyl-$C_nH_{2n}$—O—CO—, more particularly preferably from hydrogen, $(C_1-C_4)$-alkyl, $(C_3-C_7)$-cycloalkyl-$C_nH_{2n}$—, $((C_1-C_4)$-alkyl)-CO—, $(C_3-C_7)$-cycloalkyl-$C_nH_{2n}$—CO— and $((C_1-C_4)$-alkyl)-O—CO—, especially preferably from hydrogen, $(C_1-C_4)$-alkyl and $(C_3-C_7)$-cycloalkyl-$C_nH_{2n}$—, more especially preferably from hydrogen and $(C_1-C_4)$-alkyl. In one embodiment of the present invention the group $R^{12}$ is hydrogen.

In the compounds of the formulae I and Ia the group $R^{13}$ is preferably chosen from hydrogen and $(C_1-C_4)$-alkyl and more preferably from hydrogen and methyl. Particularly preferably $R^{13}$ is hydrogen.

In the compounds of the formula Ia a heteroaryl group is preferably a 5-membered or 6-membered, monocyclic aromatic group which contains one, two or three identical or different hetero ring members chosen from N, $NR^{13}$, O and S. Particularly preferably a heteroaryl group in the compounds of the formulae I and Ia is a 5-membered or 6-membered, monocyclic aromatic group which contains one or two identical or different hetero ring members chosen from N, $NR^{13}$, O and S.

In the compounds of the formula Ia the number n is preferably 0, 1 or 2, wherein all numbers n are independent of each other and can be identical or different. Particularly preferably the number n in the compounds of the formulae I and Ia is 0 or 1, wherein all numbers n are independent of each other and can be identical or different.

In preferred embodiments of the present invention one or more or all of the groups contained in the compounds of formulae I and Ia can independently of each other have any of the preferred definitions of the groups specified above or any one or some of the specific denotations which are comprised by the definitions of the groups and specified above, all combinations of preferred definitions and/or specific denotations being a subject of the present invention. Also with respect to all preferred embodiments the invention includes the compounds of the formulae I and Ia in all stereoisomeric forms and mixtures of stereoisomeric forms in all ratios, and their physiologically acceptable salts, as well as their tautomeric forms.

For example, one such embodiment of the present invention relates to compounds of the formulae I and Ia in which simultaneously A is chosen from —CH=CH—$CH_2$—, —C≡C—$CH_2$—, which groups are bonded to the group Het via the terminal atom of the double or triple bond, and the group of the formula IIa, which is bonded to the group Het via a ring atom,

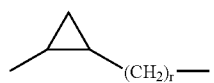

IIa wherein in the formula IIa the bonds via which the group is connected to the adjacent groups, are depicted by the lines starting at a ring atom and at the group $(CH_2)_r$, and wherein all groups A can be substituted by one or more identical or different substituents $R^4$;

Het is chosen from pyridinediyl, thiazolediyl, oxazolediyl, imidazolediyl and thiophenediyl which can all be substituted by one or more identical or different substituents $R^5$ and wherein one of the ring nitrogen atoms of the imidazolediyl group carries a group chosen from hydrogen and $(C_1-C_4)$-alkyl;

X is chosen from a direct bond and O;

$R^1$ and $R^2$ are independently of each other chosen from $(C_1-C_4)$-alkyl, $(C_3-C_7)$-cycloalkyl-$C_nH_{2n}$—, phenyl-$C_nH_{2n}$—, and heteroaryl-$C_nH_{2n}$—, and $R^2$ can in addition be hydrogen, wherein the groups $(C_1-C_4)$-alkyl and $(C_3-C_7)$-cycloalkyl can both be substituted by one or more identical or different substituents $R^6$, and all phenyl groups and heteroaryl groups can be substituted by one or more identical or different substituents $R^7$, or $R^1$ and $R^2$, together with the N—CO group which carries them, form a 4-membered to 7-membered, monocyclic, saturated or unsaturated heterocycle which, in addition to the ring nitrogen atom being part of the N—CO group, can contain one further hetero ring member chosen from N, $NR^{12}$, O, S, SO and $SO_2$, wherein the ring formed by $R^1$ and $R^2$ and the N—CO group which carries them can be substituted by one or more identical or different substituents $R^8$;

$R^3$ is phenyl which can be substituted by one or more identical or different substituents which are chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di($(C_1-C_4)$-alkyl)amino, $CONH_2$, CN, $CF_3$ and $(C_1-C_4)$-alkyl-$SO_2$—;

$R^4$ is chosen from methyl and fluorine;

$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, $CONH_2$, CN, $CF_3$ and $(C_1-C_4)$-alkyl-$SO_2$—;

$R^6$ is chosen from fluorine, $(C_1-C_4)$-alkyloxy, di($(C_1-C_4)$-alkyl)amino, $((C_1-C_4)$-alkyl)-CONH—, di($(C_1-C_4)$-alkyl)aminocarbonyl-, $((C_1-C_4)$-alkyloxy)carbonyl-, COOH and $CF_3$;

$R^7$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di($(C_1-C_4)$-alkyl)amino, $((C_1-C_4)$-alkyl)-CONH—, $CONH_2$, CN, $CF_3$ and $(C_1-C_4)$-alkyl-$SO_2$—;

$R^8$ is chosen from halogen, $(C_1-C_4)$-alkyl, phenyl-$C_nH_{2n}$—, heteroaryl-$C_nH_{2n}$—, $(C_1-C_4)$-alkyloxy-$(C_1-C_2)$-alkyl-, OH, oxo, $(C_1-C_4)$-alkyloxy which can be substituted by one or more fluorine atoms, $(C_1-C_2)$-alkylenedioxy which can be substituted by one or more fluorine atoms, $(C_1-C_4)$-alkylmercapto, $(C_1-C_4)$-alkylamino, di($(C_1-C_4)$-alkyl)amino, $((C_1-C_4)$-alkyl)-CONH—, di($(C_1-C_4)$-alkyl)aminocarbonyl-, $((C_1-C_4)$-alkyloxy)carbonyl-, $CONH_2$, CN and $CF_3$, wherein all phenyl groups and heteroaryl groups can independently of each other be substituted by one or more identical or different substituents chosen from halogen, $(C_1-C_4)$-alkyl, $CF_3$ and $(C_1-C_4)$-alkyloxy;

$R^{12}$ is chosen from H, $(C_1-C_4)$-alkyl, $(C_3-C_7)$-cycloalkyl-$C_nH_{2n}$—, $((C_1-C_4)$-alkyl)-CO—, $(C_3-C_7)$-cycloalkyl-$C_nH_{2n}$—CO— and $((C_1-C_4)$-alkyl)-O—CO—;

$R^{13}$ is chosen from hydrogen and $(C_1-C_4)$-alkyl;

heteroaryl is a 5-membered or 6-membered, monocyclic aromatic group containing one or two identical or different hetero ring members chosen from N, NR$^{13}$, O and S;

n is 0 or 1, wherein all numbers n are independent of each other and can be identical or different;

r is 0 or 1;

in any of its stereoisomeric forms or a mixture of stereoisomeric forms in any ratio, or a physiologically acceptable salt thereof.

Another such embodiment of the present invention relates to compounds of the formulae I and Ia in which simultaneously A is the group of the formula IIa, which is bonded to the group Het via a ring atom,

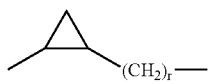

wherein in the formula IIa the bonds via which the group is connected to the adjacent groups, are depicted by the lines starting at a ring atom and at the group (CH$_2$)$_r$, and wherein the group of the formula IIa can be substituted by one or more identical or different substituents R$^4$;

Het is chosen from pyridinediyl, thiazolediyl, oxazolediyl, imidazolediyl and thiophenediyl which can all be substituted by one or more identical or different substituents R$^5$ and wherein one of the ring nitrogen atoms of the imidazolediyl group carries a group chosen from hydrogen and (C$_1$-C$_4$)-alkyl;

X is chosen from a direct bond and O;

R$^1$ and R$^2$, together with the N—CO group which carries them, form a 4-membered to 7-membered ring, monocyclic, saturated or unsaturated heterocycle which, in addition to the ring nitrogen atom being part of the N—CO group, can contain one further hetero ring member chosen from NR$^{12}$, O and S, wherein the ring formed by R$^1$ and R$^2$ and the N—CO group which carries them can be substituted by one or more identical or different substituents R$^8$;

R$^3$ is phenyl which can be substituted by one or more identical or different substituents which are chosen from halogen, (C$_1$-C$_4$)-alkyl, (C$_1$-C$_4$)-alkyloxy-(C$_1$-C$_2$)-alkyl-, (C$_1$-C$_4$)-alkyloxy which can be substituted by one or more fluorine atoms, (C$_1$-C$_4$)-alkylmercapto, (C$_1$-C$_4$)-alkylamino, di((C$_1$-C$_4$)-alkyl)amino, CONH$_2$, CN, CF$_3$ and (C$_1$-C$_4$)-alkyl-SO$_2$—;

R$^5$ is chosen from halogen, (C$_1$-C$_4$)-alkyl, (C$_1$-C$_4$)-alkyloxy-(C$_1$-C$_2$)-alkyl-, OH, (C$_1$-C$_4$)-alkyloxy which can be substituted by one or more fluorine atoms, (C$_1$-C$_4$)-alkylmercapto, NH$_2$, (C$_1$-C$_4$)-alkylamino, di((C$_1$-C$_4$)-alkyl)amino, ((C$_1$-C$_4$)-alkyl)-CONH—, CONH$_2$, CN, CF$_3$ and (C$_1$-C$_4$)-alkyl-SO$_2$—;

R$^8$ is chosen from (C$_1$-C$_4$)-alkyl and oxo;

R$^{12}$ is chosen from H and (C$_1$-C$_4$)-alkyl-;

r is 0 or 1;

in any of its stereoisomeric forms or a mixture of stereoisomeric forms in any ratio, or a physiologically acceptable salt thereof.

Another such embodiment of the present invention relates to compounds of the formula Ia in which simultaneously A is the group of the formula IIa, which is bonded to the group Het via a ring atom,

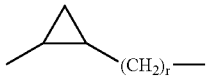

wherein in the formula IIa the bonds via which the group is connected to the adjacent groups, are depicted by the lines starting at a ring atom and at the group (CH$_2$)$_r$, and wherein the group of the formula IIa can be substituted by one or more identical or different substituents R$^4$;

Het is chosen from the pyridinediyl, thiazolediyl, oxazolediyl, imidazolediyl and thiophenediyl which can all be substituted by one or more identical or different substituents R$^5$ and wherein one of the ring nitrogen atoms of the imidazolediyl group carries a group chosen from hydrogen and (C$_1$-C$_4$)-alkyl;

X is absent and the phenyl group representing the group R$^3$ is fused to the group Het;

R$^1$ and R$^2$, together with the N—CO group which carries them, form a 4-membered to 7-membered, monocyclic, saturated or unsaturated heterocycle which, in addition to the ring nitrogen atom being part of the N—CO group, can contain one further hetero ring member chosen from NR$^{12}$, O and S, wherein the ring formed by R$^1$ and R$^2$ and the N—CO group which carries them can be substituted by one or more identical or different substituents R$^8$;

R$^3$ is phenyl which can be substituted by one or more identical or different substituents which are chosen from halogen, (C$_1$-C$_4$)-alkyl, (C$_1$-C$_4$)-alkyloxy-(C$_1$-C$_2$)-alkyl-, (C$_1$-C$_4$)-alkyloxy which can be substituted by one or more fluorine atoms, (C$_1$-C$_4$)-alkylmercapto, (C$_1$-C$_4$)-alkylamino, di((C$_1$-C$_4$)-alkyl)amino, CONH$_2$, CN, CF$_3$ and (C$_1$-C$_4$)-alkyl-SO$_2$—;

R$^5$ is chosen from halogen, (C$_1$-C$_4$)-alkyl, (C$_1$-C$_4$)-alkyloxy-(C$_1$-C$_2$)-alkyl-, OH, (C$_1$-C$_4$)-alkyloxy which can be substituted by one or more fluorine atoms, (C$_1$-C$_4$)-alkylmercapto, NH$_2$, (C$_1$-C$_4$)-alkylamino, di((C$_1$-C$_4$)-alkyl)amino, ((C$_1$-C$_4$)-alkyl)-CONH—, CONH$_2$, CN, CF$_3$ and (C$_1$-C$_4$)-alkyl-SO$_2$—;

R$^8$ is chosen from (C$_1$-C$_4$)-alkyl and oxo;

R$^{12}$ is chosen from H and (C$_1$-C$_4$)-alkyl-;

r is 0 or 1;

in any of its stereoisomeric forms or a mixture of stereoisomeric forms in any ratio, or a physiologically acceptable salt thereof.

Besides the use of the compounds of the formula Ia defined afore in which the group X is absent, for the manufacture of a medicament for the stimulation of the expression of endothelial NO synthase and for the treatment of a disease in which such a stimulation, or an increase in NO level, is desired, for example a cardiovascular disorders such as atherosclerosis, coronary artery disease or cardiac insufficiency or any other diseases mentioned above or below herein, also the compounds of the formula Ia defined afore in which the group X is absent, themselves, i.e. the novel compounds per se, are a subject of the present invention.

As in any embodiment of the invention, in the preceding embodiments which contain exemplary definitions of compounds according to the invention, one or more or all of the groups can have any of its preferred definitions specified above or any one or some of the specific denotations which are comprised by its definitions and are specified above.

A further embodiment of the present invention relates to any of the individual compounds of the formulae I and Ia which are specifically disclosed herein, including the compounds of all examples described below, in the form of the respective free compound as well as in the form of a physiologically acceptable salts thereof in general and, if a specific salt is disclosed, in the form of this specific salt, as well as to all tautomeric forms of the free compounds and their salts if tautomeric forms exist. I.e., this embodiment encompasses the physiologically acceptable salts in general of any individual compound specifically disclosed herein, irrespective thereof whether the compound is specifically disclosed as the free compound or as a specific salt. For example, as regards the compound 1-(3-(4-(4-fluorophenyl)thiazol-2-yl)allyl)pyrrolidine-2,5-dione which is specifically disclosed as the free compound, subjects of the present invention are "1-(3-(4-(4-fluorophenyl)thiazol-2-yl)allyl)pyrrolidine-2,5-dione" and "1-(3-(4-(4-fluorophenyl)thiazol-2-yl)allyl)pyrrolidine-2,5-dione or a physiologically acceptable salt thereof". As regards the compound 1-(3-(6-(4-fluorophenyl)pyridin-3-yl)allyl)piperidine-2,6-dione which is specifically disclosed as its trifluoroacetic acid salt, subjects of the present invention are "1-(3-(6-(4-fluorophenyl)pyridin-3-yl)allyl)piperidine-2,6-dione", "1-(3-(6-(4-fluorophenyl)pyridin-3-yl)allyl)piperidine-2,6-dione or a physiologically acceptable salt thereof" and "1-(3-(6-(4-fluorophenyl)pyridin-3-yl)allyl)piperidine-2,6-dione trifluoroacetic acid salt".

A further subject of the present invention are processes of preparation by which the compounds of the formulae I and Ia or salts thereof are obtainable. There are several ways of preparing the compounds by piecing suitable building blocks together.

According to one of the processes, compounds of the formulae I and Ia in which the group A is the group —CH═CH—$CH_2$— or the group —C≡C—$CH_2$—, i.e. compounds of the formulae Ib and Ic in which the groups Het, X, $R^1$, $R^2$ and $R^3$ are defined as in the compounds of the formulae I and Ia, are synthesized in a coupling reaction from compounds of the formula VI and amides of the formula VII and VIII, respectively, which comprise a terminal double bond or triple bond in the depicted substituent on the nitrogen atom.

able substituents, for example alkyl substituents. The group $L^1$ in the compounds of the formula VI is a leaving group which is substitutable by an alkene or alkyne moiety, such as halogen, for example chlorine, bromine or iodine, or a sulfonyloxy group, for example trifluoromethanesulfonyloxy. The reaction of a compound of the formula VI with a compound of the formula VII or VIII is carried under the conditions of the well-known Heck reaction and Sonogashira reaction, respectively (cf. de Meijere et al., Angew. Chem. Int. Ed. 33 (1994) 2379). Generally the reaction is performed in the presence of a transition metal catalyst, such as a palladium catalyst, for example palladium acetate in the presence of a phosphane like triphenylphosphane or tri(ortho-tolyl)phosphane or bis (triphenylphosphane)palladium chloride or tetrakis-(triphenylphosphane)palladium and, in the case of the Sonogashira reaction, a copper co-catalyst such as copper iodide, and a base, such as an amine, for example a tertiary amine like triethylamine, in an inert solvent, such as a hydrocarbon or chlorinated hydrocarbon, for example toluene, chlorobenzene, dichloromethane, an ether, for example 1,2-dimethoxyethane (=DME), tetrahydrofuran (=THF), dioxane, an amide, for example N,N-dimethylformamide (=DMF), N-methylpyrrolidin-2-one (=NMP), a nitrile, for example acetonitrile, an amine, for example triethylamine, or a mixture of two or more solvents, at temperatures from about 20° C. to about 110° C., preferably at about 40° C. to about 100° C. As is usual, the detailed conditions of a specific preparation, including the solvent, the base, the temperature, the molar ratios and other parameters, are routinely chosen by the person skilled in the art in view of the characteristics of the starting compounds and the target compound.

Instead of introducing the group A into the compound of the formulae I and Ia by means of the same building block which introduces the —$N(R^2)$—CO—$R^1$ moiety, the group A can also be introduced by the building block which introduces the $R^3$—X-Het-moiety. For example, compounds of the for-

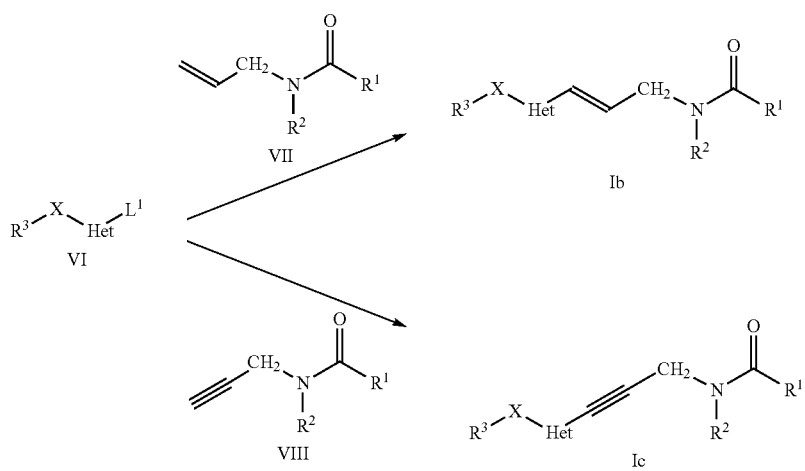

In the compounds of the formulae VI, VII and VII the groups Het, X, $R^1$, $R^2$ and $R^3$ are defined as in the compounds of the formulae I and Ia and, in addition, any functional groups can be present in protected form or in the form of precursor groups which are later converted into the desired groups. Like the group A in the compounds of the formulae I and Ia, the alkene and alkyne moiety in the compounds of the formulae VII and VIII can optionally be substituted by suitable mulae Ib and Ic can also be synthesized in an alkylation reaction from compounds of the formulae XI and XV, respectively, and compounds of the formula XII. In the compounds of the formulae XI, XII and XV the groups Het, X, $R^1$, $R^2$ and $R^3$ are defined as in the compounds of the formulae I and Ia and, in addition, any functional groups can be present in protected form or in the form of precursor groups. The groups in the compounds of the formula VI are defined as above.

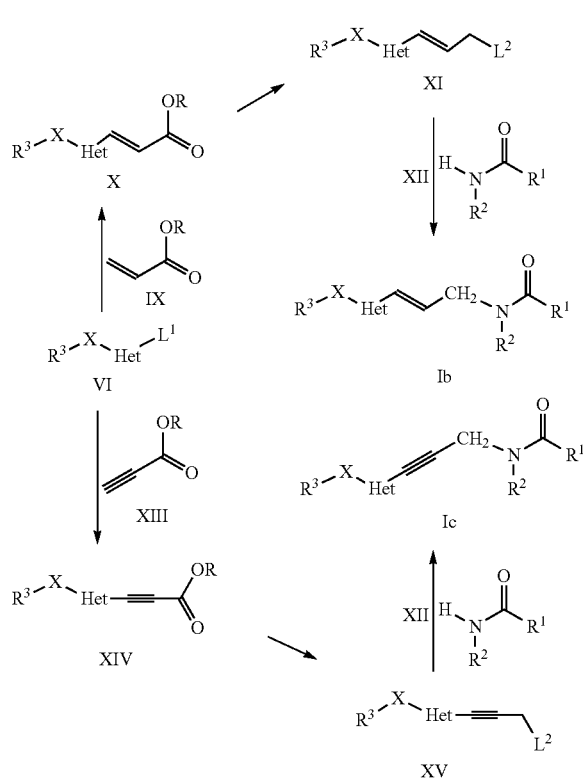

The group $L^2$ in the compounds of the formulae XI and XV is a leaving group which is nucleophilically substitutable by the compounds of the formula XII. Examples of suitable leaving groups $L^2$ are halogen, in particular chlorine and bromine, and arylsulfonyloxy groups and alkylsulfonyloxy groups such as benzenesulfonyloxy, toluenesulfonyloxy, nitrobenzenesulfonyloxy, methanesulfonyloxy and trifluoromethanesulfonyloxy.

The compounds of the formulae XI and XV can be prepared from a compound of the formula VI by first reacting it in a transition metal-catalyzed Heck coupling reaction with an unsaturated ester of the formula IX or the formula XIII to give the intermediates of the formulae X and XIV, respectively, in which the groups Het, X and $R^3$ are defined as in the compounds of the formulae I and Ia and, in addition, any functional groups can be present in protected form or in the form of precursor groups. The group R in the esters of the formulae IX, X, XIII and XIV can be an alkyl group such as $(C_1$-$C_4)$-alkyl, for example. Like the group A in the compounds of the formulae I and Ia, the alkene and alkyne moiety in the compounds of the formulae IX, X, XI, XIII, XIV and XV can optionally be substituted by suitable substituents, for example alkyl substituents. The above explanations on the Heck reaction and Sonogashira reaction apply correspondingly to preparation of the compounds of the X and XIV. Subsequently the ester group in the intermediates of the formulae X and XIV can be reduced under standard conditions to give the alcohols of the formulae $R^3$—X-Het-CH=CH—$CH_2$—OH and $R^3$—X-Het-C≡C—$CH_2$—OH, respectively, for example by means of a complex borohydride or aluminum hydride such as lithium borohydride, sodium borohydride or diisobutylaluminum hydride in a solvent such as an alcohol, like methanol or ethanol, or an ether, like tetrahydrofuran or dioxane or 1,2-dimethoxyethane, or a hydrocarbon or chlorinated hydrocarbon, like toluene, hexane or dichloromethane, or a mixture of two or more solvents. The hydroxyl group in the said alcohols can then be converted into the leaving group $L^2$, for example a halogen atom or a sulfonyloxy group by treatment with a suitable halogenating agent or sulfonylating agent under standard conditions, to give the compounds of the formulae XI and XV, for example by treatment with phosphorus tribromide or by treatment with methanesulfonyl chloride in the presence of a tertiary amine such as triethylamine in an inert solvent.

The alkylation reaction of the compounds of the formulae XI and XV and the compound of the formula XII can likewise be performed under standard conditions well known to the person skilled in the art. For binding the liberated acid of the formula $L^2$-H and/or enhancing the nucleophilicity of the compound of the formula XII in the alkylation reaction, it is often advantageous to employ a suitable base such as an amine, for example a tertiary amine like triethylamine, ethyldiisopropylamine, pyridine, an amide salt, for example sodium amide or lithium diisopropylamide, an organometallic compound, for example an organolithium compound like n-butyllithium, an alkali metal or alkaline earth metal hydride, for example lithium hydride, sodium hydride or calcium hydride, an alkali metal or alkaline earth metal hydroxide or quaternary ammonium hydroxide, for example lithium hydroxide, sodium hydroxide, potassium hydroxide, calcium hydroxide, benzyltrimethylammonium hydroxide, an alkali metal or alkaline earth metal alkoxide, for example sodium methoxide, sodium ethoxide, potassium methoxide, potassium ethoxide, potassium tert-butoxide, or another basic alkaline metal or earth alkaline metal compound, for example a carbonate like sodium carbonate, potassium carbonate, cesium carbonate, a hydrogencarbonate like sodium hydrogencarbonate, potassium hydrogencarbonate, or another basic salt, or a mixture of two or more bases. The base can be employed before the actual alkylation reaction is performed in order to convert the compound of the formula XIII into its corresponding salt. The reaction of the compounds of the formulae XI and XV and the compound of the formula XII is usually carried out in an inert solvent, which can be protic or aprotic and aqueous or non-aqueous, such as a hydrocarbon or chlorinated hydrocarbon, for example n-heptane, toluene, xylene, chlorobenzene, dichloromethane, an ether, for example diethyl ether, diisopropyl ether, 1,2-dimethoxyethane, tetrahydrofuran, dioxane, an ester, for example ethyl acetate, butyl acetate, an amide, for example N,N-dimethylformamide, N-methylpyrrolidin-2-one, a nitrile, for example acetonitrile, an alcohol, for example methanol, ethanol, isopropanol, n-butanol, or another solvent, for example water, pyridine, dimethyl sulfoxide (=DMSO), or a mixture of two or more solvents, including a mixture of water and an organic solvent which is miscible or immiscible with water. The reaction of the compounds of the formulae XI and XV and the compound of the formula XII can be carried out in a wide temperature range. Usually it is advantageous to perform the reaction at temperatures from about −20° C. to about the boiling point of the solvent used, preferably at from about 0° C. to about 100° C.

The intermediates of the formula X can also be obtained from heteroaromatic aldehydes of the formula XVI, in which the groups Het, X and $R^3$ are defined as in the compounds of the formulae I and Ia and, in addition, any functional groups can be present in protected form or in the form of precursor groups, and compounds of the formula XVII in a Knoevenagel reaction or a Wittig reaction or Wittig-Horner reaction under standard conditions.

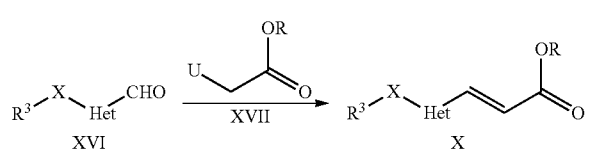

Like the group A in the compounds of the formulae I and Ia, the CHO moiety and the $CH_2$ moiety in the compounds of the formulae XVI and XVII can optionally be substituted by suitable substituents, for example alkyl substituents. In case the carbon atom adjacent to the group Het in the target compound carries an alkyl substituent, the starting compound of the formula XVI can thus also be a ketone instead of an aldehyde. The group R in the compounds of the formula XVII can be an alkyl group such as $(C_1-C_4)$-alkyl, for example. In case a Knoevenagel reaction is performed, the compound of the formula XVII can be a malonic acid derivative and the group U can be a carboxylic acid group COOH, for example. In such case the group R can also be hydrogen and thus the compound of the formula XVII be malonic acid, and the resulting compound of the formula X in which the group R is hydrogen can be esterified to give a compound of the formula X in which R is $(C_1-C_4)$-alkyl, if desired for the subsequent reaction. In case a Wittig reaction or a Wittig-Horner reaction is performed, the compound of the formula XVII can be a phosphonium salt, for example a $((C_1-C_4)$-alkyloxy)carbonylmethyltriphenyl-phosphonium halide, or a phosphonate, for example a $di((C_1-C_4)$-alkyl)$((C_1-C_4)$-alkyloxy)carbonylmethylphosphonate, and the group U be a triphenylphosphonio group having a halide anion as counterion or a $di((C_1-C_4)$-alkyl)phosphonyl group, for example. Instead of employing a $((C_1-C_4)$-alkyloxy)carbonylmethyltriphenylphosphonium halide and deprotonating it, the stable phosphorus ylide, i.e. the $((C_1-C_4)$-alkyloxy)carbonylmethylenetriphenylphosphane, can directly be employed into the reaction with the aldehydes of the formula XVI.

In a further strategy for synthesizing compounds of the formula Ib, intermediates of the formula XI can be prepared from compounds of the formula VI and allylic compounds of the formula XVIII under the conditions of the Heck coupling reaction via intermediates of the formula XIX.

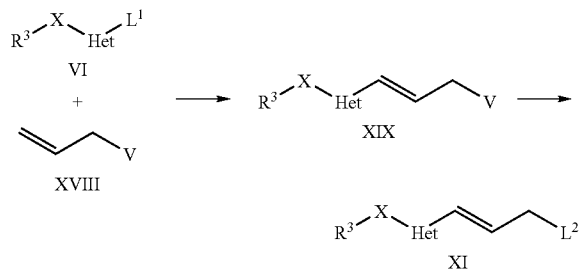

The groups Het, X and $R^3$ in the compounds of the formula XIX are defined as in the compounds of the formulae I and Ia and, in addition, any functional groups can be present in protected form or in the form of precursor groups. The groups in the compounds of the formula VI are defined as above. The group V in the compounds of the formulae XVII and XIX can be a hydroxyl group OH or a protected hydroxyl group such as an esterified, an etherified or a silylated hydroxyl group, for example, and the starting compounds of the formula XVIII can thus be allylic alcohols or protected allylic alcohols. Like the group A in the compounds of the formulae I and Ia and the alkene moiety in the compounds of the formula XI, the alkene moieties in the compounds of the formulae XVIII and XIX can optionally be substituted by suitable substituents, for example alkyl substituents. The above explanations on the Heck reaction of compounds of the formulae VI and VII apply correspondingly to the reaction of the compounds of the formulae VI and XVIII. The compounds of the formula XIX in which the group V is a hydroxyl group can then be converted into compounds of the formula XI, in which the group $L^2$ is a leaving group as defined above, under standard conditions as explained above. In case the group V in the compounds of the formula XIX is a protected hydroxyl group, first a deprotection is carried out under standard conditions.

Further synthetic strategies for the preparation of compounds of the formulae I and Ia include the assembly of the group Het in a ring-forming reaction from starting compounds which can contain the groups $R^3$—X— and -A-N$(R^2)$—CO—$R^1$ or part of these groups or protected forms or precursors thereof which are then modified in subsequent reaction steps. For example, compounds of the formulae I and Ia in which the group Het is a thiazole ring, the group X is a direct bond and the group A is the group —CH=CH—$CH_2$—, i.e. compounds of the formula Id in which the groups $R^1$, $R^2$ and $R^3$ are defined as indicated above with respect to the compounds of the formulae I and Ia, can be prepared by reacting a 2-bromo-1-$R^3$-ethanone of the formula XX in which the $CH_2$ group can optionally be substituted by a suitable substituent, for example an alkyl substituent, with a 2,2-di($(C_1-C_4)$-alkyloxy)thioacetamide of the formula XXI, for example 2,2-diethoxythioacetamide, to give a compound of the formula XXII, i.e. an acetal of a thiazole-2-carbaldehyde. The reaction can be performed by stirring the starting compounds in a solvent, for example an alcohol such as methanol or ethanol, at temperatures from about 20° C. to about 60° C., for example at room temperature. The acetal of the formula XXII can then be converted into an aldehyde of the formula XVIa by treatment with a dilute acid, for example hydrochloric acid.

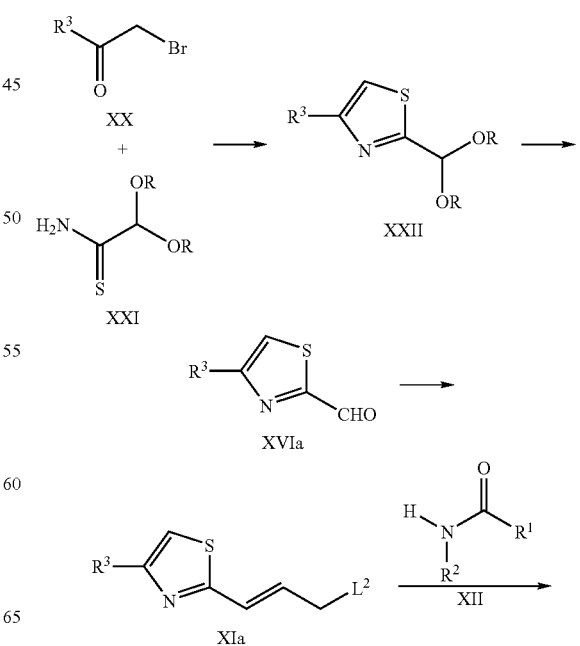

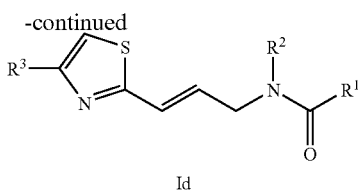
Id

The group $R^3$ in the compounds of the formulae XX, XXII, XVIa and XIa is defined as in the compounds of the formulae I and Ia and, in addition, any functional groups can be present in protected form or in the form of precursor groups. The group R in the compounds of the formulae XXI and XXII can be a $(C_1-C_4)$-alkyl group, for example, such as an ethyl group, as already indicated above. The aldehyde of the formula XVIa can be employed into a Knoevenagel reaction or a Wittig reaction or Wittig-Horner reaction as outlined above with respect to the aldehydes of the formula XVI in general to a give a compound of the formula X in which the group $R^3$—X—Het- is a 4-$R^3$-substituted thiazol-2-yl group, in which latter compound the ester group COOR can be reduced to an alcohol group $CH_2$—OH and the said alcohol group can be converted into the group $CH_2$-$L^2$ to give a compound of the formula XIa as outlined above with respect to the compounds of the formula X in general. Finally, the compound of the formula XIa, in which the leaving group $L^2$ is defined as above in the compounds of the formula XI, can be reacted in an alkylation reaction with a compound of the formula XII, which is defined as above, to give a compound of the formula Id. The above explanations on the alkylation reaction of the compounds of the formulae XI and XII apply correspondingly to the reaction of the compounds of the formulae XIa and XII. Like the group A in the compounds of the formulae I and Ia and the starting compounds and intermediates mentioned above, the acetal moiety and the aldehyde moiety in the compounds of the formulae XXI, XXII and XVIa and the alkene moiety in the compounds of the formula XIa, as well as in the compounds of the formula Id, can optionally be substituted by suitable substituents, for example alkyl substituents.

The starting compounds of the formulae VI, VII, VIII, IX, XII, XIII, XVI, XVII, XVIII, XX and XXI, as well as other starting compounds for the preparation of the compounds of the invention discussed herein, are commercially available or can be prepared according to, or analogously to, procedures which are described in the literature and are familiar to the person skilled in the art. Useful reaction types for the preparation of starting materials include in particular transition metal-catalyzed coupling reactions and catalyzed and uncatalyzed nucleophilic substitution reactions. Compounds of the formulae VI and XVI, for example, in which the group X is O, S, NH or $N((C_1-C_4)$-alkyl), can be obtained in a nucleophilic aromatic substitution reaction from a respective compound of the formula $R^3$—X—H and a suitable heteroaromatic compound containing a leaving group such as a halogen atom. Compounds of the formulae VI and XVI in which the group X is $CH_2$ can be obtained by reaction of a metalated heteroaromatic compound comprising the group Het and an alkylating agent which introduces the $R^3$—$CH_2$— moiety, or by reduction of a compound which contains a $R^3$—CO-Het- or $R^3$—CH(OH)-Het- moiety which can in turn be obtained by an acylation reaction or by reaction of an aldehyde with a metalated heteroaromatic compound. Compounds of the formula VI and XVI in which the group X is a direct bond, can be obtained in a transition metal-catalyzed Suzuki coupling reaction, or Suzuki-Miyaura coupling reaction, from a halogen-substituted heteroaromatic compound comprising the group Het and a boronic acid derivative. Such coupling reactions are favorably carried out in the presence of a palladium catalyst, for example palladium acetate or tetrakis(triphenylphosphane)palladium, in an aqueous or non-aqueous solvent. Details on such coupling reactions of boronic acid derivatives, which can advantageously be used also in other processes for the preparation of the compounds of the invention, and intermediates therefor are explained in Kotha et al., Tetrahedron 58 (2002) 9633; Miyaura, Topics in Current Chemistry 219 (2002) 11; or Walker et al., Angew. Chem. Ind. Ed. 43 (2004) 1871, for example.

Instead of employing starting compounds of the formulae VI and XVI which already comprise all the groups $R^3$, X and Het and thus introduce the group $R^3$—X-Het- as a whole into the target compound, it is also possible to start from a compound which only comprises the group Het or the groups Het and X, for example, and to introduce the group $R^3$ or the moiety $R^3$—X— at a later stage in the synthetic sequence. Thus, for example, when preparing a compound of the formula Ib or Ic, a compound of the formula XXIII instead of a compound of the formula VI can be employed as starting material into the reaction with a compound of the formulae VII, VIII, IX, XIII or XVIII. In the following, the reaction of a compound of the formula XXIII with a compound of the formula IX is taken as an example.

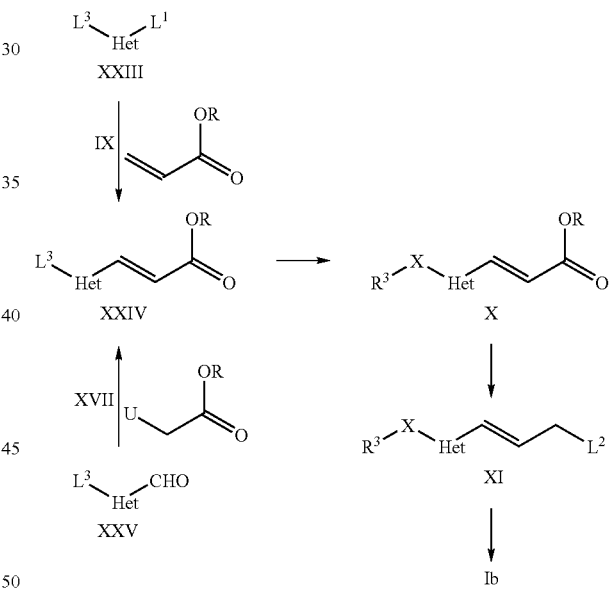

The group Het in the compounds of the formulae XXIII and XXIV is defined as in the compounds of the formulae I and Ia and, in addition, any functional groups can be present in protected form or in the form of precursor groups. The groups $L^1$ and R in the compounds of the formulae IX, X, XXIII and XXIV are defined as above. The group $L^3$ in the compounds of the formulae XXIII and XXIV is a leaving group which can be replaced with the group $R^3$—X—. Examples of suitable leaving groups $L^3$ are halogen, for example chlorine, bromine or iodine, and sulfonyloxy groups such as trifluoromethanesulfonyloxy. The group $L^3$ can be identical to or different from the group $L^1$ in the compound of the formula XXIII. Instead of being a leaving group, the group $L^3$ can also be a protected form of a leaving group or a precursor of a leaving group which is converted into a leaving group in a subsequent step, for example a hydroxyl group, or a protected hydroxyl group, which is later converted into a trifluoromethanesulfonyloxy leaving group by treatment with trifluoromethanesulfonyl anhydride. If $L^1$ and $L^3$ in the compounds of the formula XXIII are both a leaving group, the formation of the desired product can be achieved by employing suitable reaction conditions, or by employing a compound of the formula XXIII which contains two leaving groups $L^1$ and $L^3$ of different reactivity, or by taking advantage of different reactivities of leaving groups which are present in different positions of the group Het in case $L^1$ and $L^3$ are identical. The latter situation applies to a compound such as 2,5-dibromopyridine, for example, in which the bromine atom in the 2-position is more reactive than the bromine atom in the 5-position and will react first to give an intermediate in which then the bromine atom in the 5-position can be reacted (cf. Tilley et al., J. Org. Chem. 53 (1988) 386).

From a compound of the formula XXIII and a compound of the formula IX a compound of the formula XXIV can be obtained in a Heck reaction. The above explanations on the Heck reaction of the compounds of the formulae VI and VII apply correspondingly to the reaction of the compounds of the formulae XXIII and IX. In a subsequent step the group $L^3$ in the compounds of the formula XXIV can then be replaced with the group $R^3$—X— to give a compound of the formula X. The above explanations on the preparation of starting compounds comprising the moiety $R^3$—X-Het- apply correspondingly to this replacement. For example, if the group X is a direct bond, the conversion of a compound of the formula XXIV into a compound of the formula X can be achieved by reaction with a boronic acid derivative, such as a boronic acid of the formula $R^3$—B(OH)$_2$, wherein $R^3$ is defined as in the compounds of the formulae I and Ia and, in addition, any functional groups can be present in protected form or in the form of precursor groups, under the conditions of the Suzuki coupling reaction in the presence of a palladium catalyst. The compound of the formula X can then be converted into a compound of the formula XI, and the latter compound into a compound of the formula Ib, as outlined above.

Compounds of the formula XXIV can also be obtained from aldehydes of the formula XXV and compounds of the formula XVII in a Knoevenagel reaction or a Wittig reaction or Wittig-Horner reaction as outlined above. The groups Het and $L^3$ in the compounds of the formula XXV are defined as in the compounds of the formula XXIII.

Like the group A in the compounds of the formulae I and Ia and the starting compounds and intermediates mentioned above, the aldehyde moiety in the compounds of the formula XXV, the CH$_2$ moiety in the compounds of the formula XVII and the alkene moiety in the compounds of the formulae IX and XXIV, as well as in the compounds of the formulae X and XI, can optionally be substituted by suitable substituents, for example alkyl substituents.

Besides at the stage of the compounds of the formula XXIV, the replacement of the leaving group $L^3$ with the group $R^3$—X— by the above-mentioned processes can also take place at another stage of the synthesis. For example, a compound of the formula XXIV can be reduced to give an alcohol of the formula $L^3$-Het-CH═CH—CH$_2$—OH as outlined above with respect to the compounds of the formula X, in which alcohol the group $L^3$ can be replaced with the group $R^3$—X—, or which can be converted into a compound of the formula $L^3$-Het-CH═CH—CH$_2$-$L^2$ in which $L^2$ is a leaving group as defined above. In the latter compound the group $L^3$ can be replaced with the group $R^3$—X— to give a compound of the formula X, or the latter compound can be reacted with a compound of the formula XIII to give a compound of the formula $L^3$-Het-CH═CH—CH$_2$—N($R^2$)—CO—$R^1$ in which the group $L^3$ can be replaced with the group $R^3$—X— in the final step of the synthesis of a compound of the formula Ib. This synthetic variability in the assembly of the target compounds applies correspondingly to other types of compounds of the invention, and allows the person skilled in the art to adapt the synthetic strategy for the preparation of a compound to the particulars of the specific case.

The starting compounds of the formulae VII, VIII and XII can be obtained by acylation of amines of the formulae H$_2$C═CH—CH$_2$—NHR$^2$, HC≡C—CH$_2$—NHR$^2$ and $R^2$—NH$_2$, respectively, with carboxylic acids of the formula $R^1$—COOH or reactive derivatives thereof, such as acid chlorides or anhydrides, where in these compounds the groups $R^1$ and $R^2$ are defined as in the compounds of the formulae I and Ia and, in addition, any functional groups can be present in protected form or in the form of precursor groups. Compounds of the formulae VII and VIII can also be obtained by alkylation of compounds of the formula XII with an allyl halide or propargyl halide. In case $R^1$ and $R^2$ together with the N—CO group which carries them form a ring, compounds of the formulae VII, VIII and XII can also be obtained from suitable bifunctional starting compounds such as from amino-substituted carboxylic acids by cyclization or from dicarboxylic acids by conversion into the imides, for example.

Compounds of the formulae I and Ia in which the group A is a group of the formula II and the numbers q and r are 1, i.e. compounds of the formula Ie in which the groups Het, X, $R^1$, $R^2$ and $R^3$ are defined as in the compounds of the formulae I and Ia, can be prepared from compounds of the formula Ib by cyclopropanation of the double bond with a cyclopropanation reagent.

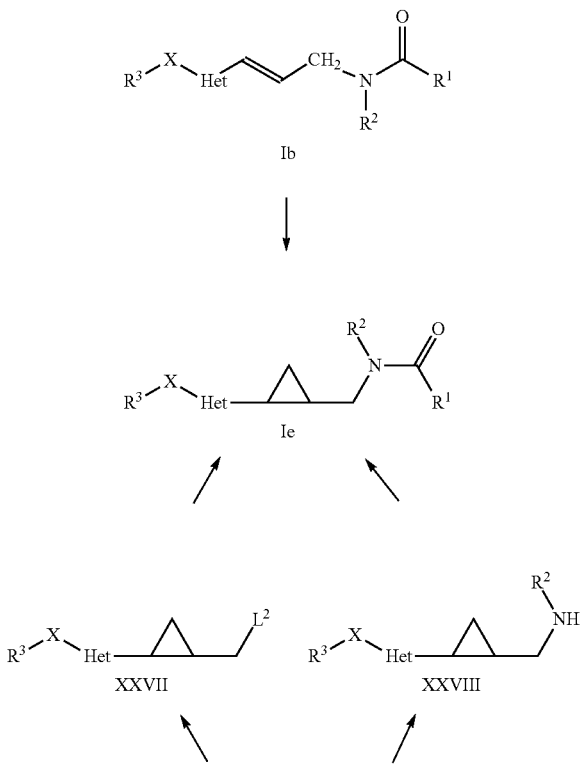

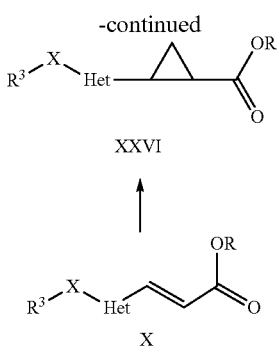

Instead of employing compounds of the formula Ib into the cyclopropanation reaction, also intermediates occurring in the synthesis of the compounds of the formula Ib can be employed, for example the compounds of the formula X which, upon cyclopropanation of the double bond, yield compounds of the formula XXVI. The compounds of the formula XXVI can be converted into compounds of the formula Ie analogously as outlined above with respect to the conversion of compounds of the formula X into compounds of the formula Ib. I.e., the ester group in the compounds of the formula XXVI can be reduced to give alcohols containing the group $CH_2$—OH instead of the group COOR, in which the hydroxy group can be converted into the leaving group $L^2$ to give the compounds of the formula XXVII, which can then be reacted in an alkylation reaction with compounds of the formula XII to give compounds of the formula Ie. The above explanations on these reactions apply correspondingly to the conversion of the compounds of the formula XXVI into the compounds of the formula Ie. In another synthetic approach, the esters of the formula XXVI or the respective carboxylic acids, i.e. the compounds which contain the carboxylic acid group COOH instead of the group COOR and which can easily be obtained from the esters, or reactive derivatives thereof such as the carboxylic acid chlorides, are first converted under standard conditions into amides which contain the group $CONHR^2$, or specifically the group $CONH_2$, instead of the group COOR. The amides can then be reduced to the amines of the formula XXVIII, for example by means of a complex borohydride or aluminum hydride, and the latter converted into the compounds of the formula Ie under standard conditions as explained below in more detail. The groups Het, X, $R^2$ and $R^3$ in the compounds of the formulae XXVI, XXVII and XXVIII are defined as in the compounds of the formulae I and Ia and, in addition, any functional groups can be present in protected form or in the form of precursor groups. I.e., the group $R^2$ in the compounds of the formula XXVIII can among others be hydrogen. The group R, which can be an alkyl group such as $(C_1-C_4)$-alkyl, and the leaving group $L^2$ in the compounds of the formulae XXVI and XXVII are defined as in the compounds of the formulae XI and IX. Like the group A in the compounds of the formulae I and Ia, the cyclopropane moiety and the $CH_2$ moiety in the compounds of the formulae XXVI, XXVII and XXVIII, as well as in the compounds of the formula Ie, can optionally be substituted by suitable substituents, for example alkyl substituents.

The amines of the formula XXVIII, in which the group $R^2$ can have the meanings indicated above with respect to the compounds of the formulae I and Ia including hydrogen, can be converted into compounds of the formula Ie according to standard procedures for the preparation of amides and lactams. For example, for the introduction of an acyl group of the formula $R^1$—CO— the amine can be reacted with a carboxylic acid chloride of the formula $R^1$—CO—Cl or an anhydride of the formula $(R^1$—$CO)_2O$, or with a carboxylic acid of the formula $R^1$—COOH, wherein these compounds the group $R^1$ is defined as in the compounds of the formulae I and Ia and, in addition, any functional groups can be present in protected form or in the form of precursor groups. The acylation with an acid of the formula $R^1$—COOH is generally carried out by means of a activating reagent or coupling reagent as are commonly used in the preparation of amides. Suitable such reagents include carbodiimides such as N,N'-dicyclohexylcarbodiimide (=DCC) or diisopropylcarbodiimide (=DIC), O-((cyano(ethoxycarbonyl)methylene)amino)-1,1,3,3-tetramethyluronium tetrafluoroborate (=TOTU), N N,N',N'-tetramethyl-O-(7-azabenzotriazol-1-yl)uronium hexafluorophosphate (=HATU), propanephosphonic acid anhydride (PPA), N,N'-carbonyldiimidazole (CDI), and chloroformic acid alkyl esters such as ethyl chloroformate or isobutyl chloroformate. The acylation is generally carried in a solvent such as, for example, toluene, dichloromethane, THF, dioxane, DMF, NMP, in the presence of a base such as, for example, triethylamine, ethyldiisopropylamine, sodium carbonate, at a temperature from about 0° C. to about 80° C., for example at room temperature. In case the group $R^2$ is hydrogen, the $NH_2$ group in the compounds of the formula XXVIII can also be incorporated into a ring, as can be formed in the compounds of the formulae I and Ia by $R^1$ and $R^2$ together with the N—CO group which carries them, for example by reaction with an ω-halogen-substituted alkanecarboxylic acid derivative such as a 4-chlorobutyric acid derivative to give a 2-oxopyrrolidin-1-yl ring system or a 5-chloropentanoic acid derivative to give a 2-oxopiperidin-1-yl ring system, or an α,ω-dicarboxylic acid derivative such as succinic anhydride or phthalic anhydride to give a 2,5-dioxopyrrolidin-1-yl ring system or a 1,3-dioxoisoindol-2-yl ring system, respectively. As another example, the incorporation of the $NH_2$ group in a compound of the formula XXVIIIa, in which $R^2$ in the formula XXVIII is hydrogen, into an imidazolidinedione ring system may be mentioned. For the preparation of respective imidazolidinedione derivatives, a compound of the formula XXVIIIa can be reacted with an isocyanatoalkanoic acid alkyl ester, which can also be named as alkyloxycarbonylalkylisocyanate, such as an isocyanatoacetic acid $(C_1-C_4)$-alkyl ester, i.e. a compound of the formula XXIX in which the group R can be an alkyl group such as $(C_1-C_4)$-alkyl, for example isocyanatoacetic acid ethyl ester, in an inert solvent, for example an ether such as THF, dioxane or DME or a hydrocarbon or chlorinated hydrocarbon, to give a compound of the formula XXX in which the group R can be an alkyl group such as $(C_1-C_4)$-alkyl.

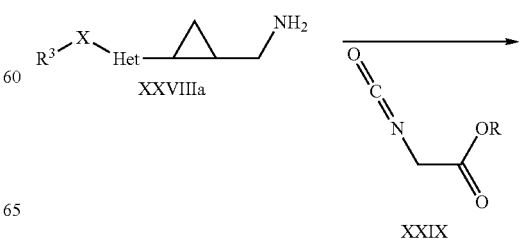

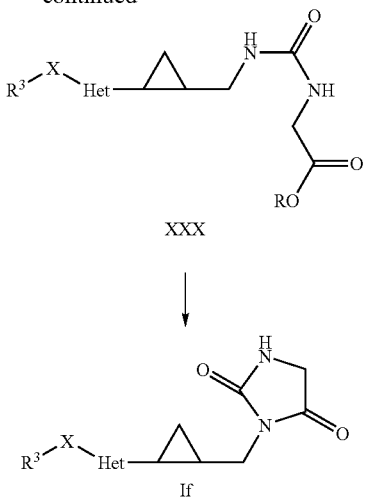

XXX

↓

If

The compound of the formula XXX can be cyclized by treatment with an acid or a base, for with example hydrochloric acid in aqueous solution, to give the imidazolidinedione derivative of the formula If, in which the groups Het, X and $R^3$ are defined as in the compounds of the formulae I and Ia. The groups Het, X and $R^3$ in the compounds of the formulae XXVIIIa and XXX are defined as in the compounds of the formulae I and Ia and, in addition, any functional groups can be present in protected form or in the form of precursor groups. Like the group A in the compounds of the formulae I and Ia, the cyclopropane moiety and the $CH_2$ moiety in the compounds of the formulae XXVIIIa and XXX, as well as in the compounds of the formula If, can optionally be substituted by suitable substituents, for example alkyl substituents.

Cyclopropanation reagents, which can be used for converting the compounds of the formulae Ib and X into the compounds of the formulae Ie and XXVI, respectively, generate a carbene or carbenoid that adds to the double bond. Such reagents include diazo compounds and diiodomethane $CH_2I_2$ in the presence of a zinc-copper couple or a zinc compound such as diethyl zinc, i.e. the well know Simmons-Smith reagent. The Simmons-Smith cyclopropanation, which is regarded as not involving a free carbene but a zinc carbenoid, can be performed in an inert solvent such as an ether, for example diethyl ether, or a chlorinated hydrocarbon, for example dichloromethane. A preferred cyclopropanation reagent is trimethylsulfoxonium iodide $(CH_3)_2S(OCH_3)^+I^-$, which can also be named as trimethyloxosulfonium iodide, and the respective trimethylsulfoxonium chloride, which upon treatment with a strong base, for example an alkaline metal hydride such as sodium hydride or dimsyl sodium, i.e. the sodium salt of dimethyl sulfoxide which can in turn be obtained from dimethyl sulfoxide and sodium hydride, provides dimethylsulfoxonium methylide, which can also be named as dimethyloxosulfonium methylide (cf. Corey et al., J. Am. Chem. Soc. 87 (1965) 1353). This sulfur ylide readily transfers a methylene group $CH_2$ onto suitable double bonds to yield the respective cyclopropane derivatives. The reaction can favorably be performed in an inert solvent, for example an ether such as tetrahydrofuran or dioxane or in dimethyl sulfoxide, at temperatures from about 0° C. to about 30° C., for example at room temperature.

Compounds of the formulae I and Ia in which the group A is a group of the formula II, the number q is greater than 1 and the number r is 1, can be prepared analogously to the above-described processes for the preparation of compounds of the formula Ib, for example from compounds of the formulae VI and VII, or from compounds of the formulae VI, IX and XII, or from compounds of the formulae XXIII, IX and XII, by employing cyclic analogs of the starting compounds of the formulae VII and IX. As pointed out above, the group A in the compounds of the formulae I and Ia can be substituted by alkyl groups representing the group $R^4$ and, like the group A in the compounds of the formulae I and Ia, the respective structural moieties in the starting compounds for their synthesis and in the synthetic intermediates can be substituted by alkyl substituents. If two such alkyl substituents, which are present in vicinal positions of the double in the starting compounds or intermediates, are formally linked together by a single bond and together thus represent a divalent alkanediyl or alkylene substituent, the resulting cyclic compounds are starting compounds or intermediates for the synthesis of the contemplated compounds of the formulae I and Ia, and provide such compounds by the processes described above, an additional hydrogenation step being needed for the conversion of the double bond to a single bond, for example a catalytic hydrogenation in the presence of palladium catalyst such as palladium on charcoal. Taking the above-described synthesis of compounds of the formula Ib from compounds of the formulae VI, IX and XII as an example, the synthesis of the contemplated compounds of the formulae I and Ia in which A is a group of the formulae II can start from a compound of the formula VI and an analog of a compound of the formula IX in which each of the two carbon atoms of the double bond is substituted by a terminal carbon atom of a divalent alkanediyl substituent and thus the double bond is part of a cycloalkene ring. The analogs of compounds of the formula IX for the synthesis of the contemplated compounds thus are cycloalkene-1-carboxylic acid esters such as cyclohexene-1-carboxylic esters, for example. In the analogs of the compounds of the formula X, the analogs of the respective compounds containing a $CH_2OH$ groups instead of the COOR group, the analogs of the compounds of the formula XI and the analogs of the compounds of the formula Ib, which can be obtained as described above, likewise the double bond is part of a cycloalkene ring which is formed by the said double bond and the divalent alkanediyl substituent. At the stage of the analog of the compound of the formula X, or at the stage of an analog of a later intermediate, or at the stage of the analog of the compound of the formula Ib, a hydrogenation of the double bond can be performed which provides the saturated cycloalkane ring present in the group of the formula II.

The preparation of compounds of the formulae I and Ia in which the group A is a group of the formula II and the number r is 0, can start from suitable intermediates for the preparation of compounds of the formulae I and Ia in which the group A is a group of the formula II and the number r is 1, which intermediates allow to split off the carbon atom which provides the moiety $(CH_2)_r$ in the latter compounds. Suitable such intermediates are the compounds of the formulae XXVI and their ring homologs, i.e. the afore-discussed analogs of compounds of the formula X in which the double is part of a cycloalkene ring and in which the double bond has been converted into a single bond by hydrogenation. Taking the preparation of compounds of the formulae I and Ia in which the group A is a group of the formula II, the number q is 1 and number r is 0 as an example, i.e. compounds of the formula Ig in which the groups

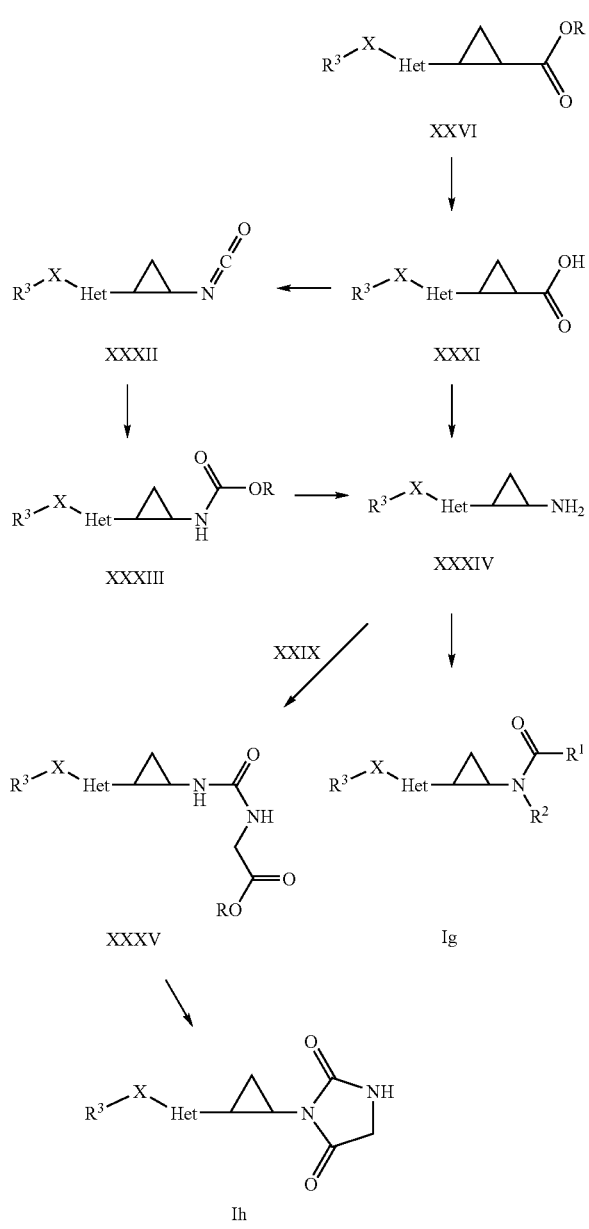

Het, X, $R^1$, $R^2$ and $R^3$ are defined as in the compounds of the formulae I and Ia, the esters of the formula XXVI can be hydrolyzed under standard conditions, for example in an acid or a solution of an alkaline metal hydroxide such as sodium hydroxide or lithium hydroxide, to give the carboxylic acids of the formula XXXI which can easily be transformed into the amines of the formula XXXIV containing one carbon atom fewer. Said transformation can be achieved under the conditions of the well known Hofmann rearrangement, or the Curtius rearrangement, or the Schmidt reaction, for example. The acid of the formula XXXI can be activated, for example by conversion into the acid chloride, reacted with ammonia to give the carboxamide, and the latter be treated with an alkali metal hypochlorite or hypobromite, for example sodium hypobromite, to give the amine of the formula XXXIV. The acid chloride can also be reacted with an azide such as sodium azide or trimethylsilyl azide to give the acid azide which upon heating, depending on the reaction conditions, provides the isocyanate of the formula XXXII or the carbamic acid ester of the formula XXXIII or the amine of the formula XXXIV. The reaction of the acid of the formula XXXI with hydrazoic acid under the conditions of the Schmidt reaction provides the amine of the formula XXXIV. A favorable method for the transformation of the acid of the formula XXXI into the amine of the formula XXXIV or the carbamic acid ester of the formula XXXIII comprises the reaction of the acid with diphenylphosphoryl azide (phenyl-O)$_2$P(O)—N$_3$, by heating the components, for example to about 80° C., in an alcohol, for example tert-butanol, in the presence of a tertiary amine such as triethylamine. Treatment of the carbamic acid ester of the formula XXXIII, which is obtained under such conditions, for example with hydrogen chloride or trifluoroacetic acid in the case of the tert-butyl carbamate, then yields the amine of the formula XXXIII. The groups Het, X and $R^3$ in the compounds of the formulae XXXI, XXXII, XXXIII and XXXIV are defined as in the compounds of the formulae I and Ia and, in addition, any functional groups can be present in protected form or in the form of precursor groups. The group R in the compounds of the formula XXXIII can be an alkyl group such as $(C_1-C_4)$-alkyl. Like the group A in the compounds of the formulae I and Ia, the cyclopropane moiety in the compounds of the formulae XXXI, XXXII, XXXIII and XXXIV, as well as in the compounds of the formula Ig, can optionally be substituted by suitable substituents, for example alkyl substituents.

The amines of the formula XXXIV can be converted into compounds of the formula Ig according to standard procedures for the preparation of amides and lactams as outlined above with respect to the conversion of the compounds of the formulae XXVII and XXVIIa into the compounds of the formulae Ie and If. Thus, for example, for the introduction of an acyl group of the formula $R^1$—CO— the amine can be reacted with a carboxylic acid chloride of the formula $R^1$—CO—Cl or an anhydride of the formula $(R^1$—CO$)_2$O, or with a carboxylic acid of the formula $R^1$—COOH in the presence of the above-mentioned activating reagents or coupling reagents, where in these compounds the group $R^1$ is defined as in the compounds of the formulae I and Ia and, in addition, any functional groups can be present in protected form or in the form of precursor groups. Just so, the NH$_2$ group in the compounds of the formula XXXIV can be incorporated into a ring, as can be formed in the compounds of the formulae I and Ia by $R^1$ and $R^2$ together with the N—CO group which carries them, for example by reaction with an ω-halogen-substituted alkanecarboxylic acid derivative such as a 4-chlorobutyric acid derivative to give a 2-oxopyrrolidin-1-yl ring system or a 5-chloropentanoic acid derivative to give a 2-oxopiperidin-1-yl ring system, or an α,ω-dicarboxylic acid derivative such as succinic anhydride or phthalic anhydride to give a 2,5-dioxopyrrolidin-1-yl ring system or a 1,3-dioxoisoindol-2-yl ring system, respectively, or by reaction with an isocyanatoalkanoic acid alkyl ester, such as an isocyanatoacetic acid $(C_1-C_4)$-alkyl ester of the formula XXVIV, and subsequent cyclization of the urea derivative of the formula XXXV, for example in the presence of hydrochloric acid in an alcohol such as ethanol, at a temperature of about 60° C. to about 100° C., for example at about 90° C., to give an imidazolidinedione derivative of the formula Ih in which Het, X and $R^3$ are defined as in the compounds of the formulae I and Ia. The groups Het, X and $R^3$ in the compounds of the formulae XXXV are defined as in the compounds of the formulae I and Ia and, in addition, any functional groups can be present in protected form or in the form of precursor groups. The group R in the compounds of the formula XXXV can be alkyl such as $(C_1-C_4)$-alkyl. Like the group A in the compounds of the formulae I and Ia, the cyclopropane moiety in the compounds of the formulae XXXV, as well as in the compounds of the formula Ih, can optionally be substituted by suitable substituents, for example alkyl substituents.

Compounds of the formulae I and Ia in which the group A is a group of the formula III, can be prepared analogously to the above-described processes for the preparation of compounds of the formula Ib, for example from compounds of the formulae VI and VII or from compounds of the formulae VI and XVIII, by employing cyclic analogs of the starting compounds of the formulae VII and XVIII. As pointed out above, the group A in the compounds of the formulae I and Ia can be substituted by alkyl groups representing the group $R^4$ and, like the group A in the compounds of the formulae I and Ia, the respective structural moieties in the starting compounds for their synthesis and in the synthetic intermediates can be substituted by alkyl substituents. If two such alkyl substituents, which are present in positions 1 and 3 with respect to each other in the allyl moiety of the starting compounds or intermediates, are formally linked together by a single bond and together thus represent a divalent alkanediyl or alkylene substituent, the resulting cyclic compounds are starting compounds or intermediates for the synthesis of the contemplated compounds of the formulae I and Ia, and provide such compounds by the processes described above, an additional hydrogenation step being needed for the conversion of the double bond to a single bond, for example a catalytic hydrogenation in the presence of palladium catalyst such as palladium on charcoal. Taking the above-described synthesis of compounds of the formula Ib from compounds of the formulae VI, XVIII and XII as an example, the synthesis of the contemplated compounds of the formulae I and Ia in which A is a group of the formulae III can start from a compound of the formula VI and an analog of a compound of the formula XVIII in which the terminal carbon atom of the double bond and the $CH_2$ group are substituted by a terminal carbon atom of a divalent alkanediyl substituent and thus the double bond is part of a cycloalkene ring. The analogs of compounds of the formula XVIII for the synthesis of the contemplated compounds thus are cycloalk-2-en-1-ols or hydroxyl-protected derivatives thereof, such as cyclohex-2-en-1-ol, for example. In the analogs of the compounds of the formulae XIX, the analogs of the compounds of the formula XI and the analogs of the compounds of the formula Ib, which can be obtained as described above, likewise the double bond is part of a cycloalkene ring which is formed by the said double bond, the $CH_2$ group and the divalent alkanediyl substituent. At the stage of the analog of the compound of the formula XIX, or at the stage of an analog of a later intermediate, or at the stage of the analog of the compound of the formula Ib, a hydrogenation of the double bond can be performed which provides the saturated cycloalkane ring present in the group of the formula III.

As explained above with respect to the synthesis of the compounds of the formulae Ib and Ic, also with respect to all other compounds of the formulae I and Ia, including the compounds of the formulae Ie, If, Ig and Ih, it is possible not to employ a starting compound which already comprises all the groups $R^3$, X and Het and thus introduces the group $R^3$—X-Het- as a whole into the target compound, but to start from a compound which only comprises the group Het or the groups Het and X, for example, and to introduce the group $R^3$ or the moiety $R^3$—X— at a later stage in the synthetic sequence. As another example of the synthetic variability in the assembly of the target compounds in the following a procedure for the preparation of compounds of the formulae Ig and Ih is outlined in which the group $R^3$ is introduced in the final step of the synthesis. According to this procedure, to which all above explanations on the respective reactions correspondingly apply, a compound of the formula XXV, in which $L^3$ is a leaving group as defined above, for example halogen or a sulfonyloxy group, can be subjected to a cyclopropanation, for example with trimethylsulfoxonium iodide and sodium hydride as a base as outlined above, to give a compound of the formula XXXVI which can be hydrolyzed to give a carboxylic acid of the formula XXXVII. The acid can be transformed into the amine of the formula XXXIX via the carbamic acid ester of the formula XXXVIII, for example by treatment with diphenylphosphoryl azide in an alcohol such as tert-butanol as outlined above. The amine can then be converted into the compounds of the formula XL in general, or can specifically be converted with a compound of the formula XXIX, via the compounds of the formula XLI, into the compounds of the formula XLII, as outlined above with respect to the conversion of the compounds of the formula XXXIV into the compounds of the formulae Ig and Ih. In the final step the group $L^3$ in the compounds of the formulae XL and XLII can then be replaced with the group $R^3$—X— to give the compounds of the formulae Ig and Ih as outlined above with respect to the introduction of the group $R^3$—X— into the compounds of the formula XXIV and into starting compounds. For example, if the group X is a direct bond, the introduction of the group $R^3$—X— into the compounds of the formulae XL and XLII can be achieved by reaction with a boronic acid of the formula $R^3$—$B(OH)_2$ under the conditions of the Suzuki coupling reaction in the presence of a palladium catalyst.

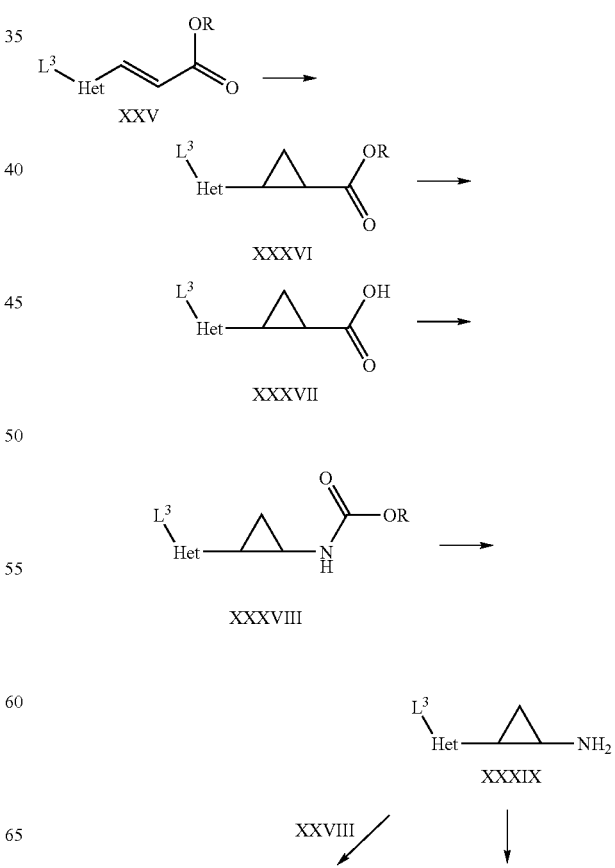

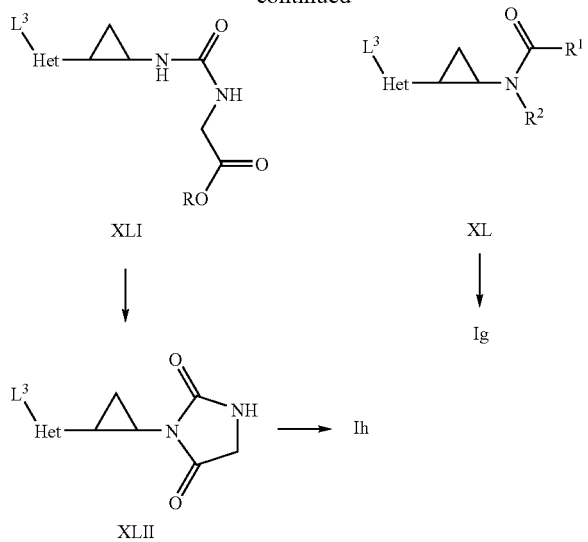

XLI

XL

↓

↓

Ig

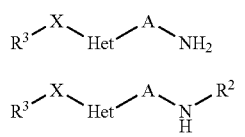

XLII

The groups Het, $R^1$ and $R^2$ in the compounds of the formulae XXXVI, XXXVII, XXXVIII, XXXIX, XL, XLI and XLII are defined as in the compounds of the formulae I and Ia and, in addition, any functional groups can be present in protected form or in the form of precursor groups. The group $L^3$ in the compounds of the formulae XXXVI, XXXVII, XXXVIII, XXXIX, XL, XLI and XLII is a leaving group which can be replaced with the group $R^3$—X—, such as halogen, for example chlorine, bromine or iodine, or a sulfonyloxy group, for example trifluoromethanesulfonyloxy. The group $L^3$ can also be a protected form of a leaving group or a precursor of a leaving group which is converted into a leaving group in a subsequent step, for example a hydroxyl group, or a protected hydroxyl group, which is later converted into a trifluoromethanesulfonyloxy leaving group. The group R in the compounds of the formula XLI can be an alkyl group such as $(C_1-C_4)$-alkyl. Like the group A in the compounds of the formulae I and Ia, the cyclopropane moiety in the compounds of the formulae XXXVI, XXXVII, XXXVIII, XXXIX, XL, XLI and XLII can optionally be substituted by suitable substituents, for example alkyl substituents.

The amide moiety —N($R^2$)—CO—$R^1$ in the compounds of the formulae I and Ia, including the compounds of the formulae Ib, Ic, Id, Ie, If, Ig and Ih, and in synthetic precursors thereof can be hydrolyzed under standard conditions to give an amino compound of the formula XLIII or, depending on the meaning of the group $R^2$, an amino compound of the formula XLIV.

$R^3$—X—Het—A—$NH_2$   XLIII $R^3$—X—Het—A—N(H)—$R^2$   XLIV

In the compounds of the formulae XLII and XLIII the groups A, Het, X, $R^2$ and $R^3$ are defined as in the compounds of the formulae I and Ia and, in addition, any functional groups can be present in protected form or in the form of precursor groups. Such hydrolysis can be carried by treating a compound of the formulae I or Ia, for example a compound of the formulae I or Ia in which the group $R^1$ is a methyl group and the group $R^2$ is hydrogen, with a dilute acid, for example hydrochloric acid, or an alkali metal hydroxide, for example a sodium hydroxide solution. In case $R^1$ and $R^2$, together with the N—CO group which carries them, in the compound of the formulae I or Ia form a 1,3-dioxoisoindol-1-yl group (=phthalimido group), the conversion into the compound of the formula XLIII can conveniently be performed by treatment with hydrazine, for example in a solvent such as ethanol under reflux, i.e. analogously to the well known Gabriel synthesis of amines. As outlined above with respect to the compounds of the formulae XXVIII and XXXIV, in general the amino compounds of the formulae XLIII and XLIV can again be converted into further compounds of the formulae I and Ia and thus are valuable intermediate compounds. The conversion can be carried out according to standard procedures for the preparation of amides and lactams mentioned above, for example by reaction with a carboxylic acid chloride of the formula $R^1$—CO—Cl or anhydride of the formula ($R^1$—CO)$_2$O, or with a carboxylic acid of the formula $R^1$—COOH by means of a activating reagent or coupling reagent as are commonly used in the preparation of amides. Likewise, the $NH_2$ group in the compounds of the formula XLIII can also be incorporated into a ring, as can be formed in the compounds of the formulae I and Ia by $R^1$ and $R^2$ together with the N—CO group which carries them, by the procedures outlined above.

Further compounds of the formulae I and Ia can be obtained from suitable compounds prepared according to the above-described processes by functionalization or modification of contained functional groups according standard procedures, for example by esterification, amidation, hydrolysis, etherification, alkylation, acylation, sulfonylation, reduction, oxidation, conversion into salts, and others.

All reactions used in the above-described syntheses of the compounds of the formulae I and Ia are per se well-known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. As far as applicable, all starting compounds and intermediates employed into the above-described syntheses can also be employed in the form of salts, and all intermediates and final target compounds can also be obtained in the form of salts. As already indicated above, depending on the circumstances of the individual case, in order to avoid an unwanted course of a reaction or side reactions during the synthesis of a compound, it can generally be necessary or advantageous to temporarily block functional groups by introducing protective groups and deprotect them at a later stage of the synthesis, or introduce functional groups in the form of precursor groups which later are converted into the desired functional groups. As examples of protecting groups amino-protecting groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protecting groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group the nitro group may be mentioned which can be converted into an amino group by reduction, for example by catalytic hydrogenation. Such synthesis strategies, and protective groups and precursor groups which are suitable in a specific case, are known to the skilled person. If desired, the obtained compounds of formulae I and Ia, as well as any intermediate compounds, can be purified by customary purification procedures, for example by recrystallization or chromatography.

The compounds of the formulae I and Ia are useful pharmacologically active, or pharmaceutically active, compounds which modulate the expression of endothelial NO synthase, and more specifically upregulate, or stimulate, the expression, or transcription, of endothelial NO synthase, and which can be employed as pharmaceuticals, or active ingredients of medicaments, for the treatment of various diseases. In the context of the present invention, treatment is understood as comprising both therapy, including alleviation and cure, of diseases and disease symptoms and prevention and prophylaxis of diseases and disease symptoms, such as, for example, the prevention of the appearance of asthmatic disease symptoms or the prevention of myocardial infarction or of myocardial reinfarction in affected patients. The diseases or disease symptoms can be acute or chronic. Diseases which can be treated with the compounds of the formulae I and Ia include, for example, cardiovascular diseases like stable and unstable angina pectoris, coronary heart disease, coronary artery disease, Prinzmetal angina (spasm), acute coronary syndrome, cardiac insufficiency, heart failure, myocardial infarction, stroke, thrombosis, peripheral artery occlusive disease (=PAOD), endothelial dysfunction, atherosclerosis, restenosis, endothel damage after PTCA (=percutaneous transluminal coronary angioplasty), hypertension including essential hypertension, pulmonary hypertension and secondary hypertension (renovascular hypertension, chronic glomerulonephritis), erectile dysfunction, and ventricular arrhythmia. Further, the compounds of the formulae I and Ia lower the cardiovascular risk of postmenopausal women or after intake of contraceptives. Compounds of the formulae I and Ia can additionally be used in the treatment, including therapy and prevention, of diabetes and diabetes complications such as nephropathy or retinopathy, angiogenesis, asthma bronchiale, chronic renal failure, cirrhosis of the liver, osteoporosis, restricted memory performance or a restricted ability to learn. Preferred indications are stable angina pectoris, coronary heart disease, hypertension, endothelial dysfunction, atherosclerosis and diabetes complications.

The compounds of the formulae I and Ia can be used in combination with other pharmacologically active compounds or pharmaceuticals, preferably with compounds which are able to enhance the effect of the compounds according to the formulae I and Ia. Examples of such other compounds include statins; ACE inhibitors; AT1 antagonists; argininase inhibitors; PDE V inhibitors; calcium antagonists; alpha blockers; beta blockers; metimazol and analogous compounds; arginine; tetrahydrobiopterin; vitamins, in particular vitamin C and vitamin B6; niacine.

The compounds of the formulae I and Ia and their physiologically acceptable salts, optionally in combination with other pharmacologically active compounds, can be administered to animals, preferably to mammals, and in particular to humans, as pharmaceuticals by themselves, in mixtures with one another, or in the form of pharmaceutical compositions. Further subjects of the present invention therefore also are the compounds of the formulae I and Ia and their physiologically acceptable salts for use as pharmaceuticals, their use as modulating agents, and more specifically as stimulating agents or upregulating agents, of the expression or transcription of endothelial NO synthase, for example in conditions in which an increased expression of said enzyme or an increased NO level or the normalization of a decreased NO level in a patient is desired, and in particular their use in the treatment, including therapy and prevention, of the above-mentioned diseases or syndromes, as well as their use for the preparation or manufacture of medicaments for these purposes. Furthermore, a subject of the present invention are pharmaceutical compositions, or pharmaceutical preparations, which comprise an effective dose of at least one compound of the formulae I or Ia and/or a physiologically acceptable salt thereof and a pharmaceutically acceptable carrier, i.e. one or more pharmaceutically acceptable carrier substances and/or additives.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously, for example in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, among others, on the disease to be treated and on its severity.

The amount of a compound of the formulae I or Ia and/or its physiologically acceptable salts present in the pharmaceutical compositions normally ranges from about 0.2 to about 800 mg, preferably from about 0.5 to about 500 mg, in particular from about 1 to about 200 mg, per dose, but depending on the type of the pharmaceutical composition it may also be higher. The pharmaceutical compositions usually comprise from about 0.5 to about 90 percent by weight of the compounds of the formulae I or Ia and/or their physiologically acceptable salts. The production of the pharmaceutical compositions can be carried out in a manner known per se. To this end, one or more compounds of the formulae I or Ia and/or their physiologically acceptable salts together with one or more solid or liquid pharmaceutical carrier substances (or vehicles) and/or additives (or auxiliary substances) and, if a combination medicament is desired, other pharmacologically active compounds having therapeutic or prophylactic action are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, starch derivatives, talc, stearic acid or its salts, etc. Soft gelatin capsules and suppositories can comprise, for example, fats, waxes, semisolid and liquid polyols, natural or hardened oils, etc. Suitable carrier substances for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formulae I and Ia and their physiologically acceptable salts and to use the resulting lyophilisates, for example, for preparing compositions for injection or infusion. Suitable carriers for microcapsules, implants or rods are, for example, copolymers of glycolic acid and lactic acid. Besides the compound or compounds according to the invention and carrier substances, the pharmaceutical compositions can also contain additives such as, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formulae I or Ia to be administered and/or of a physiologically acceptable salt thereof depends on the individual case and, as is customary, has to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the use is for the therapy of a acute or chronic disease or prophylactic, or on whether other active compounds are administered in addition to compounds of the formulae I or Ia. In general, a daily dose from about 0.01 mg/kg to about 100 mg/kg, preferably from about 0.1 mg/kg to about 10 mg/kg, in particular from about 0.3 mg/kg to about 5 mg/kg (in each case mg per kg of bodyweight) is appropriate for administration to an adult weighing about 75 kg in order to obtain the desired results. The daily dose can be administered in a single dose or, in particular when larger amounts are administered, divided into several, for example two, three or four individual doses. In some cases, depending on the individual response, it may be necessary to deviate upwards or downwards from the given daily dose.

The compounds of the formulae I and Ia can also be used for other purposes than those indicated in the foregoing. Non-limiting examples include the use as diagnostics, for example the use in methods for determining the activity of endothelial NO synthase in biological samples, the use as biochemical tools and the use as intermediates for the preparation of further compounds, for example further pharmacologically active compounds.

EXAMPLES

Compounds containing a basic group which were purified by preparative HPLC using an eluent which contained trifluoroacetic acid, were in part obtained in the form of acid addition salts with trifluoroacetic acid (TFA) which is not depicted in the formulae in the examples. The compounds were characterized by analytical high pressure liquid chromatography (HPLC) and/or mass spectrometry (MS) and/or nuclear magnetic resonance spectrometry (NMR). The MS data were obtained by electron spray ionization (ESI). The HPLC conditions were as follows.

Method HPLC A: Column material: see the specific examples. Eluent: isopropanol containing 0.1% TFA. Column dimensions and flow rate: 250×50 mm and 50 ml/min for preparative separations, 250×4.6 mm and 0.3 ml/min for analytical determinations of retention time.

Method HPLC B: Column material: see the specific examples. Eluent: heptane/methanol/ethanol 3:1:1 containing 0.1% diethylamine. Column dimensions and flow rate: 250×50 mm and 50 ml/min for preparative separations, 250× 4.6 mm and 1 ml/min for analytical determinations of retention time.

Method HPLC C: Column material: see the specific examples. Eluent: ethanol/methanol 1:1 containing 0.1% diethylamine. Column dimensions and flow rate: 250×50 mm and 50 ml/min for preparative separations, 250×4.6 mm and 1 ml/min for analytical determinations of retention time.

Method HPLC D: Column material: see the specific examples. Eluent: heptane/isopropanol 4:1 containing 0.1% diethylamine. Column dimensions and flow rate: 250×50 mm and 50 ml/min for preparative separations, 250×4.6 mm and 1 ml/min for analytical determinations of retention time.

Method HPLC E: Column material: see the specific examples. Eluent: heptane/methanol/isopropanol 5:1:1 containing 0.1% diethylamine. Column dimensions and flow rate: 250×50 mm and 50 ml/min for preparative separations, 250×4.6 mm and 1 ml/min for analytical determinations of retention time.

Example 1

1-(3-(6-(2-Fluorophenyl)pyridin-3-yl)prop-2-ynyl) piperidin-2-one trifluoroacetic acid salt

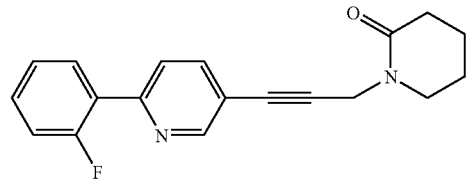

544 mg (3.96 mmol) of 1-(prop-2-ynyl)piperidin-2-one, 500 mg (1.98 mmol) of 5-bromo-2-(2-fluorophenyl)pyridine, 38 mg of copper(I)iodide and 139 mg of bis-(triphenylphosphane)palladium(II)chloride were dissolved in 20 ml of triethylamine and the mixture was stirred at 50° C. for 8 h. The solvent was removed by evaporation, and the residue was purified by preparative HPLC(RP-18, acetonitrile/water containing 0.01% TFA). Yield: 152 mg.

MS: M+H$^+$=309.

Example 2

1-(3-(6-(2-Fluorophenyl)pyridin-3-yl)prop-2-ynyl) piperidine-2,6-dione trifluoroacetic acid salt

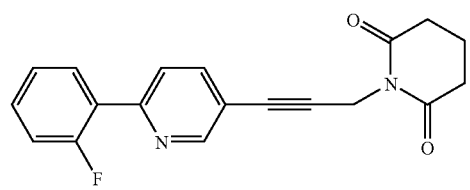 [SMILES: O=C1CCCC(=O)N1CC#Cc1ccc(-c2ccccc2F)nc1]

The compound was prepared analogously to example 1 from 599 mg (3.96 mmol) of 1-(prop-2-ynyl)piperidin-2,6-dione. Yield: 130 mg.

MS: M+H$^+$=323.

Example 3

1-(3-(4-(4-Fluorophenyl)thiazol-2-yl)allyl)-1H-pyridin-2-one

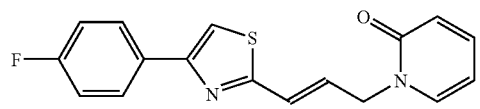 [SMILES: O=c1ccccn1C/C=C/c1nc(-c2ccc(F)cc2)cs1]

a) 4-(4-Fluorophenyl)thiazole-2-carbaldehyde 5 g (23.04 mmol) of 2-bromo-1-(4-fluorophenyl)-ethanone und 3.76 g (23.04 mmol) of 2,2-diethoxythioacetamide were stirred in 100 ml of ethanol at room temperature for 2 h. After concentrating, the residue was heated with ethyl acetate, the insolubles were filtered off, and the filtrate was evaporated. The obtained acetal (6.2 g) was stirred with 50 ml of acetone, 50 ml of water and 1 ml of 2N hydrochloric acid at room temperature for 4 h. Evaporation of the mixture yielded 4.22 g (88%) of the title compound.

MS: M+H$^+$=207.2.

b) 3-(4-(4-Fluorophenyl)thiazol-2-yl])propenal 1 g (4.82 mmol) of 4-(4-fluorophenyl)thiazole-2-carbaldehyde und 1.76 g (5.79 mmol) of 2-(triphenylphosphoranylidene)acetaldehyde were stirred in 40 ml of THF at room temperature for 5 h. The mixture was evaporated, and the residue was purified by preparative HPLC (RP18, acetonitrile/water containing 0.1% TFA). Yield: 743 mg (66%).

c) 3-(4-(4-Fluorophenyl)thiazol-2-yl)prop-2-en-1-ol 692 mg (2.97 mmol) of 3-(4-(4-fluorophenyl)thiazol-2-yl)propenal and 224.5 mg (5.93 mmol) of sodium borohydride were stirred in 50 ml of ethanol at room temperature for 3 h. Water was added, and the mixture was concentrated. The residue was taken up with water and ethyl acetate. The organic phase was separated and evaporated. The residue was purified by preparative HPLC (RP18, acetonitrile/water containing 0.1% TFA). Yield: 280 mg (40%).

d) 2-(3-Chloropropenyl)-4-(4-fluorophenyl)thiazole

258 µl (3.3 mmol) of methanesulfonyl chloride were slowly added to 265 mg (1.12 mmol) of 3-(4-(4-fluorophenyl)thiazol-2-yl)prop-2-en-1-ol and 456 mg (4.5 mmol) of triethylamine in 10 ml of dichloromethane at room temperature and the mixture was stirred for 3 h. After standing at room temperature over the weekend, the mixture was extracted with a sodium hydrogencarbonate solution. Evaporation of the organic phase yielded 280 mg of the title compound.

e) 1-(3-(4-(4-Fluorophenyl)thiazol-2-yl)allyl)-1H-pyridin-2-one 23.7 mg (0.54 mmol) of sodium hydride (55% in mineral oil) were added to 60.4 mg (0.54 mmol) of 1H-pyridin-2-one in 8 ml of DMF. The mixture was stirred at room temperature for 1 h, 92 mg (0.36 mmol) of 2-(3-chloropropenyl)-4-(4-fluorophenyl)thiazole were added, and the mixture was stirred at room temperature for another 4 h and subsequently at 50° C. for 2 h. After concentrating, water was added and the product was extracted with ethyl acetate. The organic phases were evaporated and the residue was purified by preparative HPLC (RP18, acetonitrile/water containing 0.1% TFA). Yield: 26 mg (23%).

MS: M+H$^+$=313.0. As a by-product, 8 mg of 2-(3-(4-(4-fluorophenyl)thiazol-2-yl)allyloxy)pyridine were obtained.

Example 4

3-(3-(4-(4-Fluorophenyl)thiazol-2-yl)allyl)imidazolidine-2,4-dione

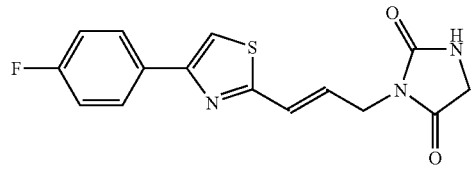 [SMILES: O=C1CNC(=O)N1C/C=C/c1nc(-c2ccc(F)cc2)cs1]

The compound was prepared analogously to example 3e) from 92 mg (0.36 mmol) of 2-(3-chloropropenyl)-4-(4-fluorophenyl)thiazole and 54.4 mg (0.54 mmol) of imidazolidine-2,4-dione. Yield: 31 mg (27%).

MS: M+H$^+$=318.2.

Example 5

1-(3-(4-(4-Fluorophenyl)thiazol-2-yl)allyl)pyrrolidine-2,5-dione

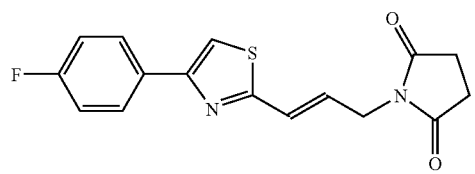 [SMILES: O=C1CCC(=O)N1C/C=C/c1nc(-c2ccc(F)cc2)cs1]

The compound was prepared analogously to example 3e) from 100 mg (0.39 mmol) of 2-(3-chloropropenyl)-4-(4-fluorophenyl)thiazole and 46.8 mg (0.47 mmol) of pyrrolidine-2,5-dione. Yield: 24 mg (17%).

MS: M+H$^+$=317.0.

Example 6

1-(3-(6-(4-Fluorophenyl)pyridin-3-yl)allyl)piperidine-2,6-dione trifluoroacetic acid salt

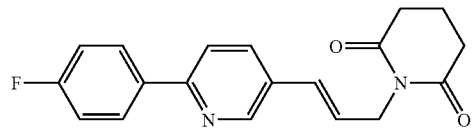

a) 3-(6-(4-Fluorophenyl)pyridin-3-yl)acrylic acid methyl ester

A mixture of 2980 mg (12.31 mmol) of 3-(6-bromopyridin-3-yl)acrylic acid methyl ester, 2067 mg (14.77 mmol) of 4-fluorophenylboronic acid, 138.2 mg (0.61 mmol) of palladium(II)acetate, 322.9 mg (1.23 mmol) of triphenylphosphane and 14.7 ml of a 1M sodium carbonate solution in 73 ml of toluene and 20 ml of ethanol was heated under reflux for 1.5 h. After cooling, the mixture was poured onto water and extracted with ethyl acetate. The organic phases were evaporated and residue purified by chromatography (silica gel, n-heptane/ethyl acetate 5:1). Yield: 2.4 g (76%).

b) 3-(6-(4-Fluorophenyl)pyridin-3-yl)prop-2-en-1-ol 520 mg (2 mmol) of 3-(6-(4-fluorophenyl)pyridin-3-yl) acrylic acid methyl ester were dissolved in 40 ml of dichloromethane and cooled to −70° C. Under argon, 4.65 ml of a 1M solution of diisobutylaluminum hydride in hexane were slowly added. The mixture was stirred at −70° C. for 3 h, quenched with a solution of sodium sulfate, and warmed to room temperature. After filtration over Celite, the organic phase was separated and evaporated. Yield: 430 mg (93%)
MS: M+H$^+$: 230.1.

c) 5-(3-Chloropropenyl)-2-(4-fluorophenyl)pyridine 436 mg (3.8 mmol) of methanesulfonyl chloride were slowly added at room temperature to 513 mg (2.24 mmol) of 3-(6-(4-fluorophenyl)pyridin-3-yl)prop-2-en-1-ol and 679 mg (6.71 mmol) of triethylamine in 20 ml of dichloromethane. The mixture was stirred at room temperature for 6 h and extracted with a sodium hydrogencarbonate solution. The organic phase was evaporated to yield 550 mg of the title compound. MS: M+H$^+$=248.1.

d) 1-(3-(6-(4-Fluorophenyl)pyridin-3-yl)allyl)piperidine-2,6-dione trifluoroacetic acid salt 20.9 mg (0.48 mmol) of sodium hydride (55% suspension in mineral oil) were added to 35 mg (0.31 mmol) of piperidine-2,6-dione in 5 ml of DMF, and the mixture was stirred at room temperature for 1 h. 64 mg (0.25 mmol) of 5-(3-chloropropenyl)-2-(4-fluorophenyl)pyridine were added, and the mixture was stirred for 1 h and allowed to stand overnight. After concentrating, water was added and the product was extracted with ethyl acetate. The organic phases were evaporated and the residue was purified by preparative HPLC (RP18, acetonitrile/water containing 0.1% TFA). Yield: 10 mg (9%).
MS: M+H$^+$=325.0.

Example 7

1-(3-(6-(4-Fluorophenyl)pyridin-3-yl)allyl)piperidin-2-one trifluoroacetic acid salt

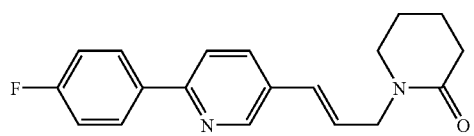

The compound was prepared analogously to example 6d) from 47.5 mg (0.48 mmol) of piperidin-2-one and 99 mg (0.4 mmol) of 5-(3-chloropropenyl)-2-(4-fluorophenyl)pyridine. Yield: 8 mg (5%).
MS: M+H$^+$=311.0.

Example 8

3-(3-(6-(4-Fluorophenyl)pyridin-3-yl)allyl)imidazolidine-2,4-dione trifluoroacetic acid salt

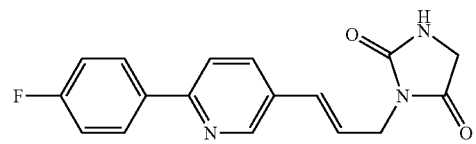 [SMILES: O=C1CNC(=O)N1C/C=C/c1ccc(-c2ccc(F)cc2)nc1]

The compound was prepared analogously to example 6d) from 48 mg (0.48 mmol) of imidazolidine-2,4-dione and 99 mg (0.4 mmol) of 5-(3-chloropropenyl)-2-(4-fluorophenyl)pyridine. Yield: 24 mg (14%).
MS: M+H$^+$=312.0.

Example 9

1-(3-(6-(4-Fluorophenyl)pyridin-3-yl)allyl)pyrrolidine-2,5-dione trifluoroacetic acid salt

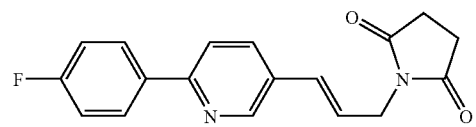 [SMILES: O=C1CCC(=O)N1C/C=C/c1ccc(-c2ccc(F)cc2)nc1]

The compound was prepared analogously to example 6d) from 47.5 mg (0.48 mmol) of pyrrolidine-2,5-dione and 99 mg (0.4 mmol) of 5-(3-chloropropenyl)-2-(4-fluorophenyl)pyridine. Yield: 51 mg (30%).
MS: M+H$^+$=311.0.

Example 10

3-(3-(5-(4-Fluorophenyl)pyridin-2-yl)allyl)imidazolidine-2,4-dione trifluoroacetic acid salt

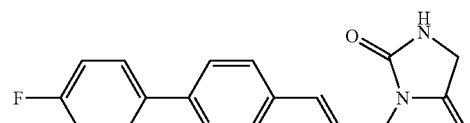

400 mg (1.59 mmol) of 2-bromo-5-(4-fluorophenyl)pyridine, 335 mg (2.39 mmol) of 3-allylimidazolidine-2,4-dione, 88 mg (0.39 mmol) of palladium(II)acetate and 119 mg (0.39 mmol) of tri(ortho-tolyl)phosphane were dissolved in a mixture of 5 ml of triethylamine, 10 ml of acetonitrile and 2 ml of DMF and heated at 90° C. for 6 h. The solvent was evaporated, the residue taken up in water and extracted with ethyl acetate. The organic phases were dried and evaporated, and the residue was purified by preparative HPLC (RP18, acetonitrile/water containing 0.01% TFA).
Yield: 23 mg.
MS: M+H$^+$=312.

Example 11

3-(3-(6-(4-Fluorophenyl)pyridin-3-yl)allyl)-5,5-dimethylimidazolidine-2,4-dione trifluoroacetic acid salt

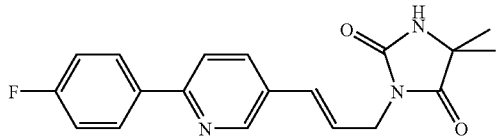

500 mg (2.0 mmol) of 5-bromo-2-(4-fluorophenyl)pyridine, 588 mg (3.5 mmol) of 3-allyl-5,5-dimethylimidazolidine-2,4-dione, 112 mg (0.5 mmol) of palladium(II)acetate and 152 mg (0.5 mmol) of tri(ortho-tolyl)phosphane were dissolved in 5 ml of triethylamine heated at 90° C. for 1 h. The solvent was evaporated, the residue taken up in water and extracted with ethyl acetate. The organic phases were dried and evaporated, and the residue was purified by preparative HPLC (RP18, acetonitrile/water containing 0.01% TFA). Yield: 750 mg.
MS: M+H$^+$=340.

Example 12

3-((E)-3-(6-(4-Fluorophenylamino)pyridin-3-yl)allyl)imidazolidine-2,4-dione trifluoroacetic acid salt

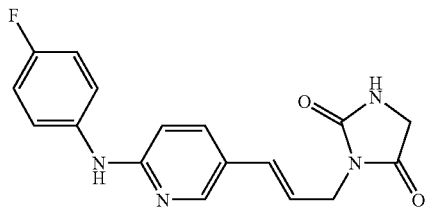 [SMILES: O=C1CNC(=O)N1C/C=C/c1ccc(Nc2ccc(F)cc2)nc1]

a) (5-Bromopyridin-2-yl)-(4-fluorophenyl)amine 5 g (21.1 mmol) of 2,5-dibromopyridine, 4.4 ml of 4-fluoroaniline, 4.10 g (42.3 mmol) of sodium-tert-butanolate, 200 mg (0.8 mmol) of palladium(II)acetate and 200 mg (0.3 mmol) of R-(+)-BINAP were dissolved in 60 ml of dioxane and stirred at reflux temperature for 1 h. The mixture was poured into ice-water and extracted with ethyl acetate. The organic phases were dried and evaporated, and the residue was purified by column chromatography (silica gel, n-heptane/ethyl acetate 5:2). Yield: 2.10 g.

b) 3-((E)-3-(6-(4-Fluorophenylamino)pyridin-3-yl)allyl)imidazolidine-2,4-dione trifluoroacetic acid salt The compound was prepared analogously to example 11 from 300 mg (1.12 mmol) of (5-bromopyridin-2-yl)-(4-fluorophenyl)amine, 276 mg (1.97 mmol) of 3-allyl-5,5-dimethylimidazolidine-2,4-dione, 63 mg (0.28 mmol) of palladium(II)acetate and 86 mg (0.28 mmol) of tri(ortho-tolyl)phosphane in 3.75 ml of triethylamine. Yield: 17 mg.
MS: M+H$^+$=327.

Example 13

1-(3-(5-(4-Fluorophenyl)pyridin-2-yl)allyl)-1H-pyridin-2-one trifluoroacetic acid salt

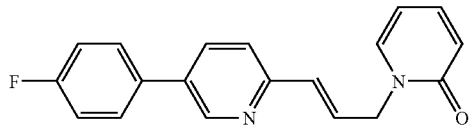 [SMILES: O=c1ccccn1C/C=C/c1ccc(-c2ccc(F)cc2)cn1]

The compound was prepared analogously to example 11 from 323 mg (2.39 mmol) of 1-allyl-1H-pyridin-2-one. Yield: 8 mg.
MS: M+H$^+$=307.

Example 14

(E)-3-(2-(6-(2,4-Difluorophenyl)pyridin-3-yl)cyclopropyl)imidazolidine-2,4-dione

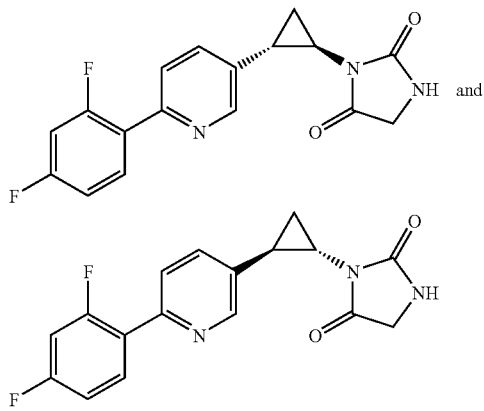

a) (E)-3-(6-Bromopyridin-3-yl)acrylic acid methyl ester 5.045 g (27.12 mmol) of 6-bromopyridine-3-carbaldehyde were dissolved in 50 ml of THF. 9.068 g (27.12 mmol) of 2-(triphenylphosphoranylidene)acetic acid methyl ester were added and the mixture was stirred at RT for 4 hours. After evaporation, the residue stirred with methanol and the solid was filtered off. The filtrate was evaporated and the residue was purified by chromatography (silica gel, ethyl acetate/n-heptane 1:4). Yield: 5.01 g (76.3%)
MS: M+H$^+$=242.02.

b) (E)-3-(6-(2,4-Difluorophenyl)pyridin-3-yl)acrylic acid methyl ester 1.0 g (4.13 mmol) of (E)-3-(6-Bromopyridin-3-yl)acrylic acid methyl ester, 782.8 mg (4.95 mmol) of 2,4-difluorophenylboronic acid, 108.4 mg (0.413 mmol) of triphenylphosphane, 46.38 mg (0.2 mmol) of palladium(II)acetate and 1.75 g (5.37 mmol) of cesium carbonate were stirred in 40 ml of dioxane and 15 ml water under argon at 100° C. for 6 h. The mixture was filtered, evaporated and the residue dissolved in methanol. By treatment with thionyl chloride the partially saponified methyl ester was re-esterified. After evaporation, the crude product was purified by chromatography (RP18, acetonitrile/water containing 0.1% TFA). Yield: 434 mg (25%).
MS: M+H$^+$=276.05.

c) (E)-2-(6-(2,4-Difluorophenyl)pyridin-3-yl)cyclopropanecarboxylic acid methyl ester 438.2 mg (1.99 mmol) of trimethylsulfoxonium iodide and 77.24 mg (1.77 mmol) of sodium hydride (55% in mineral oil) were mixed under an argon atmosphere. With stirring 4 ml of dry DMSO were slowly added, and the mixture was stirred for 30 min to give a clear solution. 406 mg (1.475 mmol) of (E)-3-(6-(2,4-difluorophenyl)pyridin-3-yl)acrylic acid methyl ester in 6 ml of dry DMSO were slowly added, and the mixture was stirred for 1.5 h. After hydrolysis with ice water the mixture was extracted with ethyl acetate. The organic layer evaporated and residue purified by chromatography (RP18, acetonitrile/water containing 0.1% TFA). Yield: 161 mg (37.7%).
MS: M+H$^+$=290.10.

d) (E)-2-(6-(2,4-Difluorophenyl)pyridin-3-yl)cyclopropanecarboxylic acid 161 mg (0.557 mmol) of (E)-2-(6-(2,4-difluorophenyl)pyridin-3-yl)cyclopropanecarboxylic acid methyl ester were stirred with 26.66 mg (1.11 mmol) of lithium hydroxide in 10 ml of THF and 2 ml of water at room temperature for 5 h. After evaporation the mixture was acidified with hydrochloric acid and extracted with ethyl acetate to yield 186 mg of the title compound (containing some salt).
MS: M+H$^+$=276.05.

e) (E)-2-(6-(2,4-Difluorophenyl)pyridin-3-yl)cyclopropylamine trifluoroacetic acid salt 273 mg (0.99 mmol) of (E)-2-(6-(2,4-difluorophenyl)pyridin-3-yl)cyclopropanecarboxylic acid, 764.6 mg (2.78 mmol) of diphenylphosphoryl azide and 393 µl (2.82 mmol) of triethylamine were heated in 20 ml of tert-butanol under reflux for 8 hours. The mixture was evaporated and the residue treated with water and extracted with ethyl acetate. The organic phases were evaporated and the obtained crude (2-(6-(2,4-difluorophenyl)pyridin-3-yl)cyclopropyl)carbamic acid tert-butyl ester was stirred with 5 ml of 90% trifluoroacetic acid at room temperature. Evaporation and purification by chromatography (RP18, acetonitrile/water containing 0.1% TFA) yielded 128 mg (35.8%) of the title compound.
MS: M+H$^+$=247.10.

f) (3-((E)-2-(6-(2,4-Difluorophenyl)pyridin-3-yl)cyclopropyl)ureido)acetic acid ethyl ester 44.08 mg (0.34 mmol) of isocyanatoacetic acid ethyl ester were slowly added to 123 mg (0.34 mmol) of (E)-2-(6-(2,4-difluorophenyl)pyridin-3-yl)cyclopropylamine trifluoroacetic acid salt and 190 µl (1.37 mmol) of triethylamine in 5 ml THF at room temperature. After 5 h the mixture was evaporated and the residue was taken up in water and ethyl acetate. The organic layer was evaporated to yield 107 mg (83.5%) of the title compound.
MS: M+H$^+$=376.15.

g) 3-((E)-2-(6-(2,4-Difluorophenyl)pyridin-3-yl)cyclopropyl)imidazolidine-2,4-dione 107 mg (0.285 mmol) of (3-((E)-2-(6-(2,4-difluorophenyl)pyridin-3-yl)cyclopropyl)-ureido)acetic acid ethyl ester were heated with 1 ml of ethanol and 5 ml of a 4N hydrochloric acid at 90° C. for 5 h. The mixture was evaporated, and the residue was purified by chromatography (RP18, acetonitrile/water containing 0.1% TFA) to yield a racemic mixture of the two enantiomers of the (E)-configured (=trans-configured) title compound.

Separation of the racemic mixture of the enantiomers by HPLC on a chiral phase (method HPLC A, column: Daicel Chiralpak AD/H) yielded 4 mg and 5 mg, respectively, of the pure enantiomers one of which is 3-((1R,2S)-2-(6-(2,4-difluorophenyl)pyridin-3-yl)cyclopropyl)imidazolidine-2,4-dione and the other of which is 3-((1S,2R)-2-(6-(2,4-difluorophenyl)pyridin-3-yl)cyclopropyl)imidazolidine-2,4-dione.

Enantiomer 1 (example 14-1): Retention time=14.27 min. MS: M+H$^+$=330.11.

Enantiomer 2 (example 14-2): Retention time=16.97 min. MS: M+H$^+$=330.11.

Example 15

3-((E)-2-(6-(3-Chloro-4-fluorophenyl)pyridin-3-yl)cyclopropyl)imidazolidine-2,4-dione

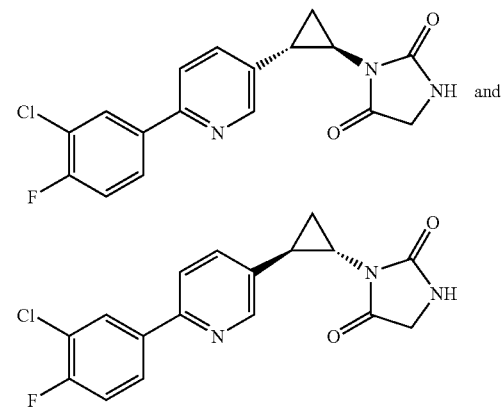

Analogously to example 14, a racemic mixture of the two enantiomers of the (E)-configured (=trans-configured) title compound was prepared.

Separation of the racemic mixture of the enantiomers by HPLC on a chiral phase (method HPLC A, column: Daicel Chiralpak AD/H) yielded 4 mg and 5 mg, respectively, of the pure enantiomers one of which is 3-((1R,2S)-2-(6-(3-chloro-4-fluorophenyl)pyridin-3-yl)cyclopropyl)imidazolidine-2,4-dione and the other of which is 3-((1S,2R)-2-(6-(3-chloro-4-fluorophenyl)pyridin-3-yl)cyclopropyl)imidazolidine-2,4-dione.

Enantiomer 1 (example 15-1): Retention time=16.49 min. MS: M+H$^+$=346.08.

Enantiomer 2 (example 15-2): Retention time=18.97 min. MS: M+H$^+$=346.10.

Example 16

3-((E)-2-(6-(2,3-Difluorophenyl)pyridin-3-yl)cyclopropyl)imidazolidine-2,4-dione

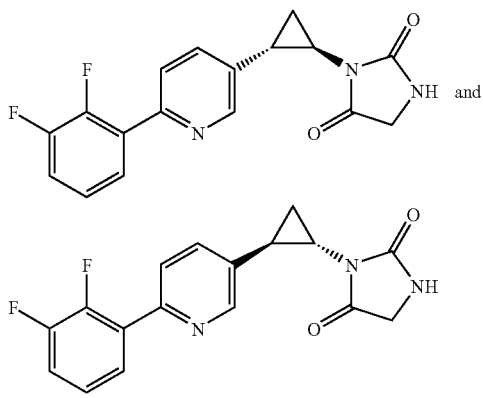

Analogously to example 14, a racemic mixture of the two enantiomers of the (E)-configured (=trans-configured) title compound was prepared.

Separation of the racemic mixture of the enantiomers by HPLC on a chiral phase (method HPLC A, column: Daicel Chiralcel OJ/H) yielded 14 mg each of the pure enantiomers one of which is 3-((1R,2S)-2-(6-(2,3-difluorophenyl)pyridin-3-yl)cyclopropyl)imidazolidine-2,4-dione and the other of which is 3-((1S,2R)-2-(6-(2,3-difluorophenyl)pyridin-3-yl)cyclopropyl)imidazolidine-2,4-dione.

Enantiomer 1 (example 16-1): Retention time=17.69 min. MS: M+H$^+$=330.14.

Enantiomer 2 (example 16-2): Retention time=21.55 min. MS: M+H$^+$=330.13.

Example 17

3-((E)-2-(6-(2,3-Dichlorophenyl)pyridin-3-yl)cyclopropyl)imidazolidine-2,4-dione

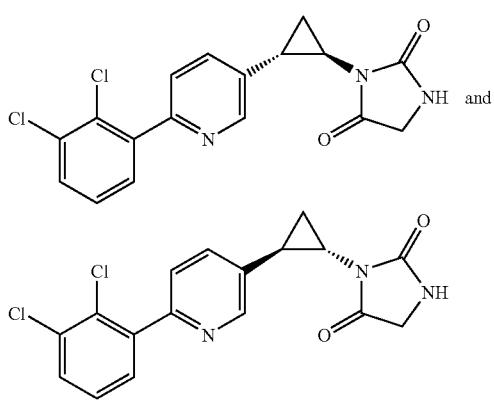

Analogously to example 14, a racemic mixture of the two enantiomers of the (E)-configured (=trans-configured) title compound was prepared.

Separation of the racemic mixture of the enantiomers by HPLC on a chiral phase (method HPLC A, column: Daicel Chiralcel OD/H) yielded 17 mg and 15 mg, respectively, of the pure enantiomers one of which is 3-((1R,2S)-2-(6-(2,3-dichlorophenyl)pyridin-3-yl)cyclopropyl)imidazolidine-2,4-dione and the other of which is 3-((1S,2R)-2-(6-(2,3-dichlorophenyl)pyridin-3-yl)cyclopropyl)imidazolidine-2,4-dione.

Enantiomer 1 (example 17-1): Retention time=16.28 min. MS: M+H$^+$=362.10.

Enantiomer 2 (example 17-2): Retention time=18.18 min. MS: M+H$^+$=362.09.

Example 18

3-((E)-2-(6-(4-Fluoro-3-methylphenyl)pyridin-3-yl)cyclopropyl)imidazolidine-2,4-dione

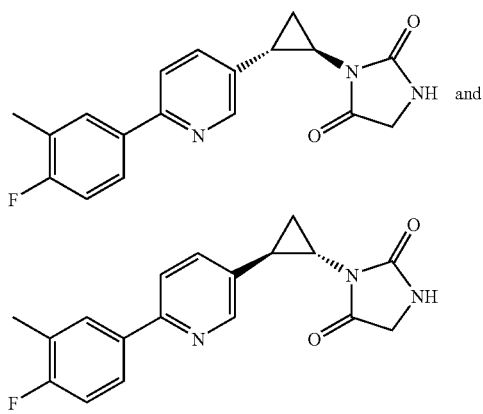

Analogously to example 14, a racemic mixture of the two enantiomers of the (E)-configured (=trans-configured) title compound was prepared.

Separation of the racemic mixture of the enantiomers by HPLC on a chiral phase (method HPLC A, column: Daicel Chiralpak AD/H) yielded 6 mg each of the pure enantiomers one of which is 3-((1R,2S)-2-(6-(4-fluoro-3-methylphenyl)pyridin-3-yl)cyclopropyl)imidazolidine-2,4-dione and the other of which is 3-((1S,2R)-2-(6-(4-fluoro-3-methylphenyl)pyridin-3-yl)cyclopropyl)imidazolidine-2,4-dione.

Enantiomer 1 (example 18-1): Retention time=5.22 min. MS: M+H$^+$=326.23.

Enantiomer 2 (example 18-2): Retention time=13.68 min. MS: M+H$^+$=326.24.

Example 19

3-((E)-2-(6-(3,4-Difluorophenyl)pyridin-3-yl)cyclopropyl)imidazolidine-2,4-dione

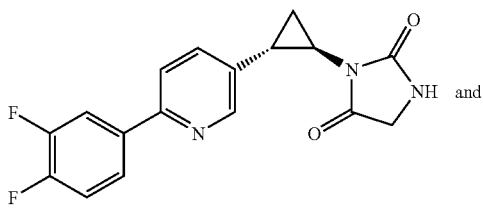

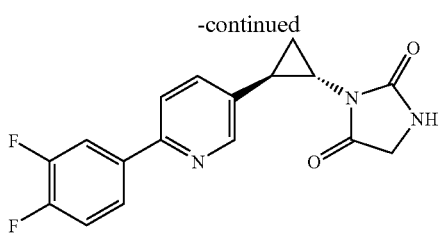

Analogously to example 14, a racemic mixture of the two enantiomers of the (E)-configured (=trans-configured) title compound was prepared.

Separation of the racemic mixture of the enantiomers by HPLC on a chiral phase (method HPLC A, column: Daicel Chiralpak AD/H) yielded 4 mg and 5 mg, respectively, of the pure enantiomers one of which is 3-((1R,2S)-2-(6-(3,4-difluorophenyl)pyridin-3-yl)cyclopropyl)imidazolidine-2,4-dione and the other of which is 3-((1S,2R)-2-(6-(3,4-difluorophenyl)pyridin-3-yl)cyclopropyl)imidazolidine-2,4-dione.

Enantiomer 1 (example 19-1): Retention time=15.54 min. MS: M+H$^+$=330.11.

Enantiomer 2 (example 19-2): Retention time=17.63 min. MS: M+H$^+$=330.12.

Example 20

3-((E)-2-(6-(4-Fluorophenyl)pyridin-3-yl)cyclopropyl)imidazolidine-2,4-dione

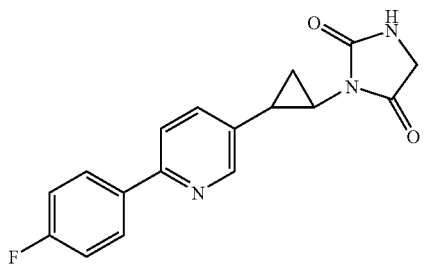 [SMILES: O=C1CNC(=O)N1C1CC1c1ccc(-c2ccc(F)cc2)nc1]

Analogously to example 14, a racemic mixture of the two enantiomers of the (E)-configured (=trans-configured) title compound was prepared, i.e. a racemic mixture of 3-((1R,2S)-2-(6-(4-fluorophenyl)pyridin-3-yl)cyclopropyl)imidazolidine-2,4-dione and 3-((1S,2R)-2-(6-(4-fluorophenyl)pyridin-3-yl)cyclopropyl)imidazolidine-2,4-dione.

Example 21

3-((E)-2-(6-(3-Chloro-4-fluorophenyl)pyridin-3-yl)cyclopropyl)imidazolidine-2,4-dione

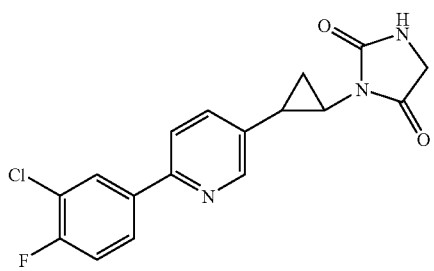 [SMILES: O=C1CNC(=O)N1C1CC1c1ccc(-c2ccc(F)c(Cl)c2)nc1]

a) 6-Bromopyridine-3-carbaldehyde 40.1 ml of a 2M solution of n-butylmagnesium chloride in THF (80.2 mmol) were added to a solution 100.2 ml of a 1.6M solution of n-butyllithium in hexane (160.41 mmol) in 50 ml of toluene and 50 ml of THF at −10° C. to 0° C. over 0.5 h, and the mixture was stirred at −10° C. for 0.5 h. A solution of 50 g (211 mmol) of 2,5-dibromopyridine in 200 ml of toluene and 200 ml of THF was added dropwise over 1 h while maintaining the temperature of the mixture below −5° C. The resulting suspension was stirred at −10° C. for 2.5 h and then transferred into a cooled (−10° C.) solution of 21.2 ml of DMF (274.3 mmol) in 100 ml of toluene and 100 ml of THF over 0.5 h. The mixture was left at −10° C. to −5° C. for 0.5 h and then quenched with 400 ml of water. After stirring the mixture below 20° C. for 10 min, the organic layer was separated and the aqueous layer was extracted three times with 400 ml each of ethyl acetate. The combined extracts were dried over sodium sulfate and concentrated in vacuo. The residue was purified by chromatography (silica gel, cyclohexane/ethyl acetate 9:1) to give 23.9 g (60.8%) of the title compound as a white solid.

Mp. (melting point): 106° C. $^1$H-NMR (400 MHz, CDCl$_3$): δ (ppm)=7.6 (d, 1H), 7.95 (d, 1H), 8.75 (s, 1H), 10 (s, 1H).

b) 3-(6-Bromopyridin-3-yl)acrylic acid methyl ester 20 g (59.8 mmol) of 2-(triphenylphosphoranylidene)acetic acid methyl ester were added, by portion, to a solution of 11.1 g (59.8 mmol) of 6-bromopyridine-3-carbaldehyde in anhydrous THF at 0° C. The mixture was stirred at 0° C. to room temperature for 4 h. The solvent was removed in vacuo and the residue was purified by chromatography (silica gel, cyclohexane/ethyl acetate 95:5) to give 13.1 g (90.4%) of the title compound (trans/cis ratio 95:5) as a white solid.

Mp.: 150° C. $^1$H-NMR (400 MHz, CDCl$_3$): δ (ppm)=3.75 (s, 3H), 6.4 (d, 1H), 7.45 (d, 1H), 7.52 (d, 1H), 7.6 (d, 1H), 8.4 (s, 1H).

c) (E)-2-(6-Bromopyridin-3-yl)cyclopropanecarboxylic acid methyl ester 80 ml of anhydrous dimethyl sulfoxide were added over 15 minutes to a mixture of 0.76 g (19 mmol) of sodium hydride (60% in mineral oil) and 4.9 g (38.34 mmol) of trimethylsulfoxonium iodide cooled in an ice bath. The cooling bath was removed, and the resulting suspension was stirred for additional 30 min. A solution of 4 g (16.5 mmol) of 3-(6-bromopyridin-3-yl)acrylic acid methyl ester in 50 ml of anhydrous dimethyl sulfoxide was added to the mixture over 10 min. The resulting homogeneous yellow solution was stirred for 2 h at room temperature and poured into 200 ml of cold water. The solution was extracted three times with 300 ml each of ethyl acetate, and the combined extracts were washed with 500 ml of brine. The organic layer was dried over sodium sulfate and concentrated in vacuo. The residue was purified by chromatography (silica gel, cyclohexane/ethyl acetate, 95:5) to give 2.9 g (68.8%) of the title compound as a beige solid.

$^1$H-NMR (400 MHz, CDCl$_3$): δ (ppm)=1.35 (m, 1H), 1.7 (m, 1H), 1.95 (m, 1H), 2.55 (m, 1H), 3.8 (s, 3H), 7.25 (d, 1H), 7.45 (d, 1H), 8.25 (s, 1H).

d) (E)-2-(6-Bromopyridin-3-yl)cyclopropanecarboxylic acid 1.04 g (24.9 mmol) of lithium hydroxide were added to a stirred solution of 2.9 g (11.3 mmol) of (E)-2-(6-Bromopyridin-3-yl)cyclopropanecarboxylic acid methyl ester in a mixture of 5 ml of THF, 5 ml of water and 2.5 ml of ethanol. The mixture was stirred at room temperature for 18 h. The solvent was removed in vacuo. The residue was dissolved in 3 ml of water and the resulting solution was neutralized by aqueous 1N hydrochloric acid at 0° C. The precipitate was collected by filtration, washed with diethyl ether and dried over phosphorus pentoxide to give 2.3 g of the title compound as a white solid.

Mp.: 166° C. $^1$H-NMR (400 MHz, CDCl$_3$): δ (ppm)=1.5 (m, 2H), 2 (m, 1H), 2.5 (m, 1H), 7.6 (dd, 2H), 8.4 (s, 1H), 12.1 (m, 1H; COOH).

e) ((E)-2-(6-Bromopyridin-3-yl)cyclopropyl)carbamic acid tert-butyl ester

A solution of 10 g (41.3 mmol) of (E)-2-(6-bromopyridin-3-yl)cyclopropanecarboxylic acid in 100 ml of tert-butanol, 10.7 ml (47.5 mmol) of diphenylphosphoryl azide and 6.6 ml (47.5 mmol) of triethylamine was heated at 80° C. for 3 h. The solvent was removed in vacuo, and the residue was dissolved in ethyl acetate. The resulting solution was washed with a saturated solution of sodium hydrogencarbonate and with brine. The organic layer was dried over sodium sulfate and concentrated in vacuo. The residue was purified by chromatography (silica gel, cyclohexane/ethyl acetate 8:2) to give 10.5 g (81%) of the title compound.

$^1$H-NMR (400 MHz, CDCl$_3$): δ (ppm)=1.25 (m, 2H), 1.5 (s, 9H), 2.1 (m, 1H), 2.75 (m, 1H), 4.9 (m, 1H—NH), 7.45 (d, 2H), 8.3 (s, 1H).

f) (E)-2-(6-Bromopyridin-3-yl)cyclopropylamine dihydrochloride 41.9 ml of a 4N solution of hydrogen chloride in dioxane (167.6 mmol) were added to a solution of 10.5 g (33.5 mmol) of ((E)-2-(6-bromopyridin-3-yl)cyclopropyl)carbamic acid tert-butyl ester in 100 ml of dichloromethane at room temperature. The mixture was stirred overnight at room temperature and the solvent was removed in vacuo. The residue was dissolved in diethyl ether. The precipitate was filtered, washed three times with diethyl ether and dried over phosphorus pentoxide to give 9.5 g (quantitative yield) of crude title compound.

Mp.: 190° C.

g) (3-((E)-2-(6-Bromopyridin-3-yl)cyclopropyl)ureido)acetic acid ethyl ester To a solution of 9.5 g (33.5 mmol) of (E)-2-(6-bromopyridin-3-yl)cyclopropylamine dihydrochloride in 100 ml of dry THF were added 15.4 ml (110.65 mmol) of triethylamine, followed by 3.83 ml (33.5 mmol) of isocyanatoacetic acid ethyl ester. The mixture was stirred at room temperature for 2 h. The solvent was removed in vacuo. The residue was dissolved in ethyl acetate and washed four times with water.

The organic layer was dried over sodium sulfate and concentrated in vacuo to give 11 g (quantitative yield) of crude title compound.

Mp.: 164° C. $^1$H-NMR (400 MHz, CDCl$_3$): δ (ppm)=1.25 (t, 3H), 1.3 (m, 2H), 2.05 (m, 1H), 2.65 (m, 1H), 3.9 (q, 2H), 4.15 (q, 2H), 5.3 (m, 2H; NH), 7.3 (d, 1H), 7.35 (d, 1H), 8.2 (s, 1H).

h) 3-((E)-2-(6-Bromopyridin-3-yl)cyclopropyl)imidazolidine-2,4-dione

A solution of 10.7 g (31.2 mmol) of (3-((E)-2-(6-bromopyridin-3-yl)cyclopropyl)ureido)-acetic acid ethyl ester in 63.6 ml of aqueous 5N hydrochloric acid and 14 ml of ethanol was heated at reflux for 3 h. The solvent was removed in vacuo. The residue was dissolved in ethanol and the solvent removed in vacuo. This operation was repeated three times. The resulting white solid was dried over phosphorus pentoxide overnight to give 10.3 g of the title compound.

Mp.: 198° C. $^1$H-NMR (400 MHz, CDCl$_3$): δ (ppm)=1.55 (m, 1H), 1.65 (m, 1H), 2.35 (m, 1H), 2.75 (m, 1H), 3.9 (s, 2H), 7.6 (s, 2H), 8.35 (s, 1H), 10.4 (m, 1H; NH)

i) 3-((E)-2-(6-(3-Chloro-4-fluorophenyl)pyridin-3-yl)cyclopropyl)imidazolidine-2,4-dione Under an argon atmosphere, a solution of 0.13 g (0.39 mmol) of 3-((E)-2-(6-bromopyridin-3-yl)cyclopropyl)imidazolidine-2,4-dione, 0.136 g (0.78 mmol) of 3-chloro-4-fluorophenylboronic acid, 0.162 g (1.17 mmol) of potassium carbonate and 9 mg (0.0078 mmol) of tetrakis(triphenylphosphane)palladium in 2 ml of DME and 1 ml of water was heated at 85° C. for 5 h. 7 ml of brine were added to the mixture. The resulting solution was loaded onto a ChemElut® column and extracted with dichloromethane. The solvent was removed in vacuo. The residue was purified by chromatography (silica gel, cyclohexane/ethyl acetate/ethanol 5:5:0.01 to 5:5:0.1) to give 0.082 g (60%) of the (E)-configured (=trans-configured) title compound, i.e. of a racemic mixture of 3-((1R,2S)-2-(6-(3-chloro-4-fluorophenyl)pyridin-3-yl)cyclopropyl)-imidazolidine-2,4-dione and 3-((1S,2R)-2-(6-(3-chloro-4-fluorophenyl)pyridin-3-yl)cyclopropyl)imidazolidine-2,4-dione, as a beige solid.

Mp.: 172° C. MS: M+H$^+$=346. $^1$H-NMR (400 MHz, CDCl$_3$): δ (ppm)=1.5 (m, 1H), 1.7 (m, 1H), 2.5 (m, 1H), 2.7 (m, 1H), 3.9 (s, 2H), 5.4 (s, 1H; NH), 7.25 (m, 1H), 7.6 (m, 2H), 7.75 (m, 1H), 7.95 (m, 1H), 8.55 (s, 1H).

According to the method described in example 21i), by replacing the 3-chloro-4-fluorophenylboronic acid employed in example 21 with the respective boronic acid of the formula R$^{50}$—B(OH)$_2$, the 3-((E)-2-(6-R$^{50}$-pyridin-3-yl)cyclopropyl)imidazolidine-2,4-diones of examples 22 to 40 were prepared, i.e. the E-configured (=trans-configured compounds of the formula Ik wherein the aromatic or heteroaromatic group R$^{50}$ is as specified in table 1, which are racemic mixtures of the 3-((1R,2S)-2-(6-R$^{50}$-pyridin-3-yl)cyclopropyl)imidazolidine-2,4-dione and the 3-((1S,2R)-2-(6-R$^{50}$-pyridin-3-yl)cyclopropyl)imidazolidine-2,4-dione of the formulae Im and In.

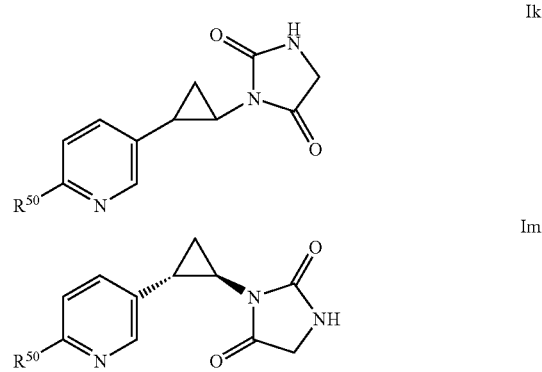

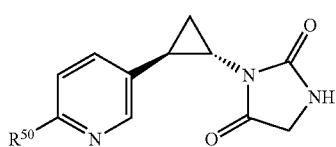

The names of the compounds of examples 22 to 40 are obtained by replacing the identifier $R^{50}$ in the general name 3-((E)-2-(6-$R^{50}$-pyridin-3-yl)cyclopropyl)-imidazolidine-2,4-dione of the compounds of formula Ik with the meaning of $R^{50}$ given in table 1, optionally allowing for a modification of the name according to the nomenclature rules. For example, in the case of example 25, in which $R^{50}$ is a quinolin-6-yl group, the prepared compound of the formula Ik thus is 3-((E)-2-(6-(quinolin-6-yl)pyridin-3-yl)cyclopropyl)imidazolidine-2,4-dione, and in the case of example 28, in which $R^{50}$ is a 3-cyano-4-fluorophenyl group, the prepared compound is 3-((E)-2-(6-(3-cyano-4-fluorophenyl)pyridin-3-yl)cyclopropyl)imidazolidine-2,4-dione which can also be named as 5-(5-((E)-2-(2,5-dioxoimidazolidin-1-yl)cyclopropyl)pyridin-2-yl)-2-fluorobenzonitrile.

TABLE 1

Example compounds of formula Ik

| Example no. | $R^{50}$ | MS M + H⁺ |
|---|---|---|
| 22 | 4-fluoro-2-methylphenyl | 326 |
| 23 | 4-fluoronaphthalen-1-yl | 362 |
| 24 | 3,5-difluorophenyl | 330 |
| 25 | quinolin-6-yl | 345 |
| 26 | 2,3,4-trifluorophenyl | 348 |
| 27 | 3,4,5-trifluorophenyl | 348 |
| 28 | 3-cyano-4-fluorophenyl | 337 |
| 29 | 3,5-dichlorophenyl | 362 |
| 30 | 3,5-dimethylphenyl | 322 |
| 31 | 2,3-dimethylphenyl | 322 |
| 32 | quinolin-5-yl | 345 |
| 33 | naphthalen-1-yl | 344 |
| 34 | naphthalen-2-yl | 344 |
| 35 | 3,4-dichlorophenyl | 362 |
| 36 | 4-chloro-3-fluorophenyl | 346 |
| 37 | 3-fluoro-4-methylphenyl | 326 |
| 38 | 4-cyano-3-fluorophenyl | 337 |
| 39 | 4-trifluoromethylphenyl | 362 |
| 40 | 5-methylthiophen-2-yl | 314 |

Example 41

3-((E)-2-(6-(4-Fluoro-2-methylphenyl)pyridin-3-yl)cyclopropyl)imidazolidine-2,4-dione

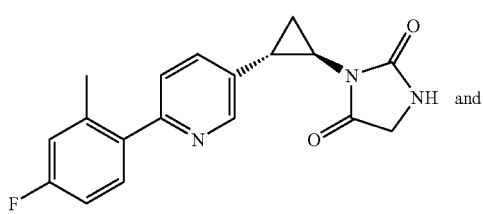 and

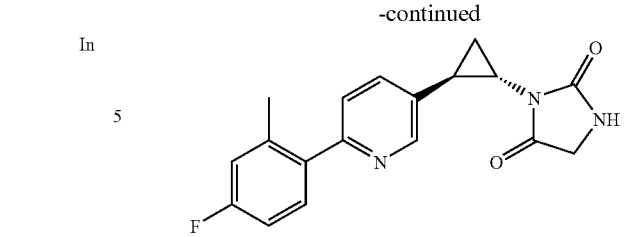

Separation of the racemic mixture of the enantiomers of the (E)-configured (=trans-configured) title compound obtained in example 22 by HPLC on a chiral phase (method HPLC D, column: Daicel Chiralcel OD/H) yielded the pure enantiomers one of which is 3-((1R,2S)-2-(6-(4-fluoro-2-methylphenyl)pyridin-3-yl)cyclopropyl)imidazolidine-2,4-dione and the other of which is 3-((1S,2R)-2-(6-(4-fluoro-2-methylphenyl)pyridin-3-yl)cyclopropyl)imidazolidine-2,4-dione.

Enantiomer 1 (example 41-1): Retention time=18.97 min. MS: M+H⁺=326.

Enantiomer 2 (example 41-2): Retention time=20.78 min. MS: M+H⁺=326.

Example 42

3-((E)-2-(6-(3,5-Difluorophenyl)pyridin-3-yl)cyclopropyl)imidazolidine-2,4-dione

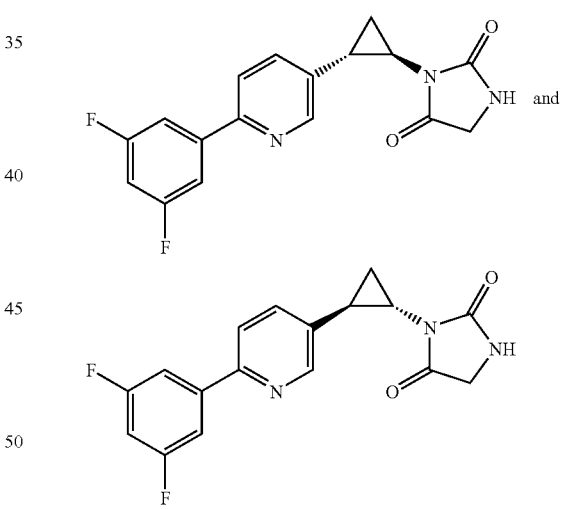

Separation of the racemic mixture of the enantiomers of the (E)-configured (=trans-configured) title compound obtained in example 24 by HPLC on a chiral phase (method HPLC B, column: Daicel Chiralcel OJ/H) yielded the pure enantiomers one of which is 3-((1R,2S)-2-(6-(3,5-difluorophenyl)pyridin-3-yl)cyclopropyl)imidazolidine-2,4-dione and the other of which is 3-((1S,2R)-2-(6-(3,5-difluorophenyl)pyridin-3-yl)cyclopropyl)imidazolidine-2,4-dione.

Enantiomer 1 (example 42-1): Retention time=8.66 min. MS: M+H⁺=330.

Enantiomer 2 (example 42-2): Retention time=10.76 min. MS: M+H⁺=330.

Example 43

3-((E)-2-(6-(Quinolin-6-yl)pyridin-3-yl)cyclopropyl)imidazolidine-2,4-dione

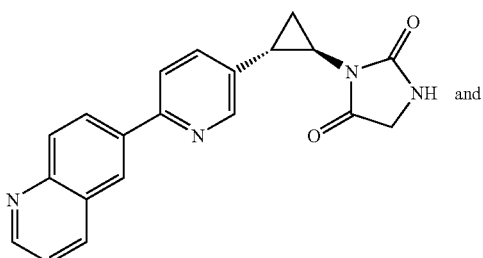

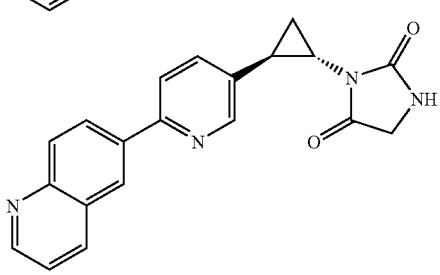

Separation of the racemic mixture of the enantiomers of the (E)-configured (=trans-configured) title compound obtained in example 25 by HPLC on a chiral phase (method HPLC C, column: Daicel Chiralcel OJ) yielded the pure enantiomers one of which is 3-((1R,2S)-2-(6-(quinolin-6-yl)pyridin-3-yl)cyclopropyl)imidazolidine-2,4-dione and the other of which is 3-((1S,2R)-2-(6-(quinolin-6-yl)pyridin-3-yl)cyclopropyl)imidazolidine-2,4-dione.

Enantiomer 1 (example 43-1): Retention time=10.48 min. MS: M+H$^+$=345.

Enantiomer 2 (example 43-2): Retention time=14.51 min. MS: M+H$^+$=345.

Example 44

3-((E)-2-(6-(2,3,4-Trifluorophenyl)pyridin-3-yl)cyclopropyl)imidazolidine-2,4-dione

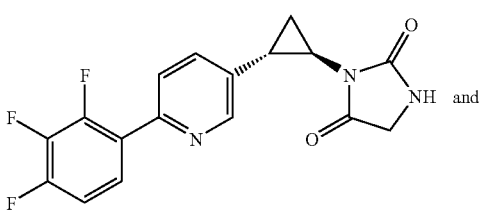

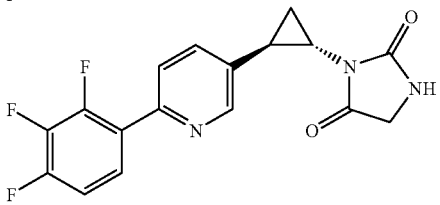

Separation of the racemic mixture of the enantiomers of the (E)-configured (=trans-configured) title compound obtained in example 26 by HPLC on a chiral phase (method HPLC B, column: Daicel Chiralcel OJ) yielded the pure enantiomers one of which is 3-((1R,2S)-2-(6-(2,3,4-trifluorophenyl)pyridin-3-yl)cyclopropyl)imidazolidine-2,4-dione and the other of which is 3-((1S,2R)-2-(6-(2,3,4-trifluorophenyl)pyridin-3-yl)cyclopropyl)imidazolidine-2,4-dione.

Enantiomer 1 (example 44-1): Retention time=9.34 min. MS: M+H$^+$=348.

Enantiomer 2 (example 44-2): Retention time=13.13 min. MS: M+H$^+$=348.

Example 45

3-((E)-2-(6-(3,4,5-Trifluorophenyl)pyridin-3-yl)cyclopropyl)imidazolidine-2,4-dione

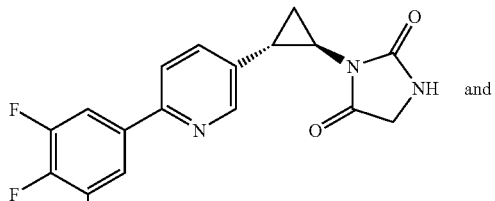

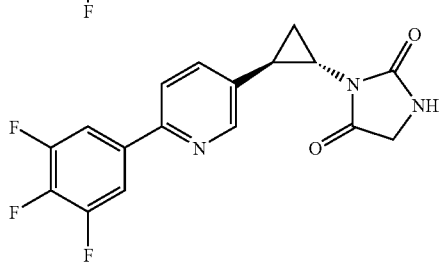

Separation of the racemic mixture of the enantiomers of the (E)-configured (=trans-configured) title compound obtained in example 27 by HPLC on a chiral phase (method HPLC B, column: Daicel Chiralcel OJ) yielded the pure enantiomers one of which is 3-((1R,2S)-2-(6-(3,4,5-trifluorophenyl)pyridin-3-yl)cyclopropyl)imidazolidine-2,4-dione and the other of which is 3-((1S,2R)-2-(6-(3,4,5-trifluorophenyl)pyridin-3-yl)cyclopropyl)imidazolidine-2,4-dione.

Enantiomer 1 (example 45-1): Retention time=11.19 min. MS: M+H$^+$=348.

Enantiomer 2 (example 45-2): Retention time=14.84 min. MS: M+H$^+$=348.

Example 46

5-(5-((E)-2-(2,5-Dioxoimidazolidin-1-yl)cyclopropyl)pyridin-2-yl)-2-fluorobenzonitrile

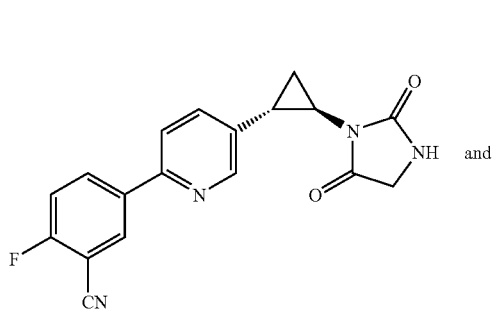

-continued

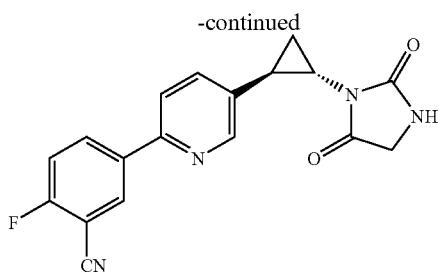

Separation of the racemic mixture of the enantiomers of the (E)-configured (=trans-configured) title compound obtained in example 28 by HPLC on a chiral phase (method HPLC C, column: Daicel Chiralcel OJ) yielded the pure enantiomers one of which is 5-(5-((1R,2S)-2-(2,5-dioxoimidazolidin-1-yl)cyclopropyl)pyridin-2-yl)-2-fluorobenzonitrile and the other of which is 5-(5-((1S,2R)-2-(2,5-dioxoimidazolidin-1-yl)cyclopropyl)pyridin-2-yl)-2-fluorobenzonitrile.

Enantiomer 1 (example 46-1): Retention time=10.08 min. MS: M+H$^+$=337.

Enantiomer 2 (example 46-2): Retention time=12.17 min. MS: M+H$^+$=337.

Example 47

3-((E)-2-(6-(3,5-Dimethylphenyl)pyridin-3-yl)cyclopropyl)imidazolidine-2,4-dione

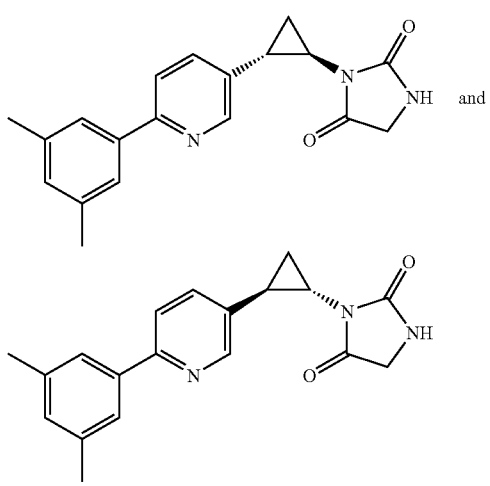

Separation of the racemic mixture of the enantiomers of the (E)-configured (=trans-configured) title compound obtained in example 30 by HPLC on a chiral phase (method HPLC C, column: Daicel Chiralcel OJ/H) yielded the pure enantiomers one of which is 3-((1R,2S)-2-(6-(3,5-dimethylphenyl)pyridin-3-yl)cyclopropyl)imidazolidine-2,4-dione and the other of which is 3-((1S,2R)-2-(6-(3,5-dimethylphenyl)pyridin-3-yl)cyclopropyl)imidazolidine-2,4-dione.

Enantiomer 1 (example 47-1): Retention time=9.89 min. MS: M+H$^+$=322.

Enantiomer 2 (example 47-2): Retention time=14.77 min. MS: M+H$^+$=322.

Example 48

3-((E)-2-(6-(2,3-Dimethylphenyl)pyridin-3-yl)cyclopropyl)imidazolidine-2,4-dione

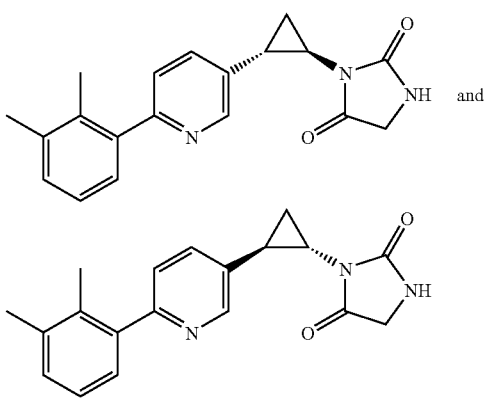

Separation of the racemic mixture of the enantiomers of the (E)-configured (=trans-configured) title compound obtained in example 31 by HPLC on a chiral phase (method HPLC E, column: Daicel Chiralcel OD/H) yielded the pure enantiomers one of which is 3-((1R,2S)-2-(6-(2,3-dimethylphenyl)pyridin-3-yl)cyclopropyl)imidazolidine-2,4-dione and the other of which is 3-((1S,2R)-2-(6-(2,3-dimethylphenyl)pyridin-3-yl)cyclopropyl)imidazolidine-2,4-dione.

Enantiomer 1 (example 48-1): Retention time=9.55 min. MS: M+H$^+$=322.

Enantiomer 2 (example 48-2): Retention time=11.08 min. MS: M+H$^+$=322.

Example 49

3-((E)-2-(6-(3,4-Dichlorophenyl)pyridin-3-yl)cyclopropyl)imidazolidine-2,4-dione

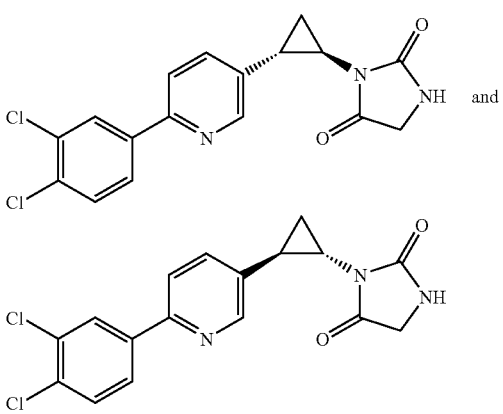

Separation of the racemic mixture of the enantiomers of the (E)-configured (=trans-configured) title compound obtained in example 35 by HPLC on a chiral phase (method HPLC B, column: Daicel Chiralcel OJ) yielded the pure enantiomers one of which is 3-((1R,2S)-2-(6-(3,4-dichlorophenyl)pyridin-3-yl)cyclopropyl)imidazolidine-2,4-dione and the other of which is 3-((1S,2R)-2-(6-(3,4-dichlorophenyl)pyridin-3-yl)cyclopropyl)imidazolidine-2,4-dione.

Enantiomer 1 (example 49-1): Retention time=16.06 min. MS: M+H⁺=362.

Enantiomer 2 (example 49-2): Retention time=21.22 min. MS: M+H⁺=362.

Example 50

3-((E)-2-(6-(4-Chloro-3-fluorophenyl)pyridin-3-yl)cyclopropyl)imidazolidine-2,4-dione

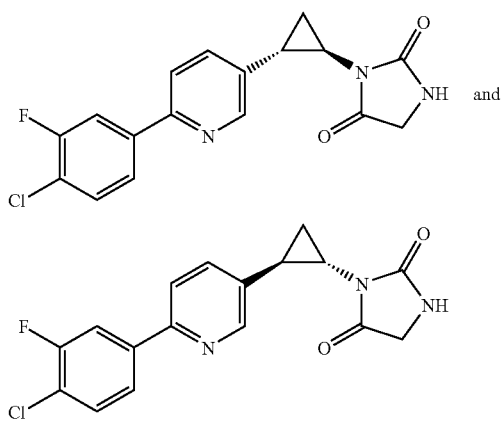

Separation of the racemic mixture of the enantiomers of the (E)-configured (=trans-configured) title compound obtained in example 36 by HPLC on a chiral phase (method HPLC C, column: Daicel Chiralcel OJ) yielded the pure enantiomers one of which is 3-((1R,2S)-2-(6-(4-chloro-3-fluorophenyl)pyridin-3-yl)cyclopropyl)imidazolidine-2,4-dione and the other of which is 3-((1S,2R)-2-(6-(4-chloro-3-fluorophenyl)pyridin-3-yl)cyclopropyl)imidazolidine-2,4-dione.

Enantiomer 1 (example 50-1): Retention time=7.82 min. MS: M+H⁺=346.

Enantiomer 2 (example 50-2): Retention time=10.42 min. MS: M+H⁺=346.

Example 51

3-((E)-2-(6-(3-Fluoro-4-methylphenyl)pyridin-3-yl)cyclopropyl)imidazolidine-2,4-dione

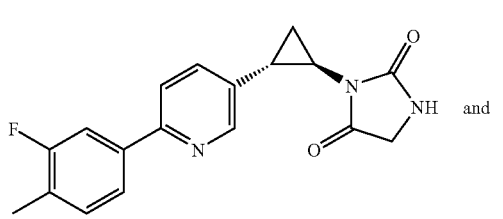

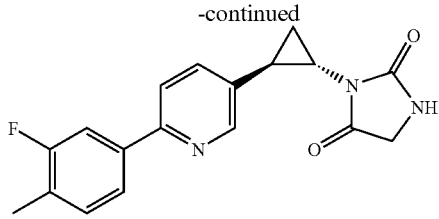

Separation of the racemic mixture of the enantiomers of the (E)-configured (=trans-configured) title compound obtained in example 37 by HPLC on a chiral phase (method HPLC C, column: Daicel Chiraicel OJ/H) yielded the pure enantiomers one of which is 3-((1R,2S)-2-(6-(3-fluoro-4-methylphenyl)pyridin-3-yl)cyclopropyl)imidazolidine-2,4-dione and the other of which is 3-((1S,2R)-2-(6-(3-fluoro-4-methylphenyl)pyridin-3-yl)cyclopropyl)imidazolidine-2,4-dione.

Enantiomer 1 (example 51-1): Retention time=9.89 min. MS: M+H⁺=326.

Enantiomer 2 (example 51-2): Retention time=14.77 min. MS: M+H⁺=326.

Example 52

3-((E)-2-(6-(5-Methylthiophen-2-yl)pyridin-3-yl)cyclopropyl)imidazolidine-2,4-dione

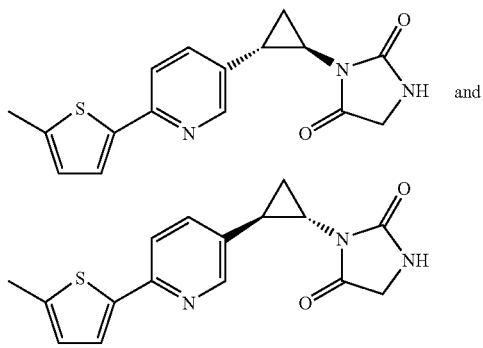

Separation of the racemic mixture of the enantiomers of the (E)-configured (=trans-configured) title compound obtained in example 37 by HPLC on a chiral phase (method HPLC C, column: Daicel Chiralcel OJ) yielded the pure enantiomers one of which is 3-((1R,2S)-2-(6-(5-methylthiophen-2-yl)pyridin-3-yl)cyclopropyl)imidazolidine-2,4-dione and the other of which is 3-((1S,2R)-2-(6-(5-methylthiophen-2-yl)pyridin-3-yl)cyclopropyl)imidazolidine-2,4-dione.

Enantiomer 1 (example 52-1): Retention time=12.82 min. MS: M+H⁺=314.

Enantiomer 2 (example 52-2): Retention time=18.72 min. MS: M+H⁺=314.

Determination of the Biological Activity

A) Activation of eNOS Transcription

Activation of eNOS transcription was measured as described in detail by Li et al., "Activation of protein kinase C alpha and/or epsilon enhances transcription of the human endothelial nitric oxide synthase gene", Mol. Pharmacol. 53 (1998) 630. Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with the compounds.

All compounds were dissolved in sterile dimethyl sulfoxide (DMSO). A final concentration of 0.5% DMSO in complete medium was allowed. Induction of reporter gene expression in these cells was measured using a standard luciferase assay system (Promega, Cat. No. E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. $EC_{50}$ values of transcription induction ratios as a function of compound concentration were determined graphically.

Numerous compounds of the instant invention were tested by the above-described assay and found to increase protein transcription. Generally, the tested compounds exhibited $EC_{50}$ values of less than about 50 µM. Preferred compounds, including the compounds of examples 2, 3, 11, 32, 38, for example, exhibited $EC_{50}$ values of from about 5 µM to about 0.5 µM. More preferred compounds, including the compounds of examples 14-2, 15-1, 16-1, 17-2, 18-1, 19-1, 21, 25, 28, 34, 40, for example, exhibited $EC_{50}$ values of less than about 0.5 µM.

The effect of compounds on eNOS-transcription was confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Western blotting procedure. After compound incubation, HUVEC were lysed in ice-cold lysis buffer containing 10 mM Tris-HCl, pH 8.0, 1% SDS and protease inhibitors. The lysate was subjected to a standard denaturating polyacrylamide gel electrophoresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemofluorescence detection method.

The effect of the compounds of the formulae I and Ia can also be investigated in the following animal models (animal experiments are performed in accordance with the German animal protection law and the guidelines for the use of experimental animals as given by the Guide for the Care and Use of Laboratory Animals of the US National Institutes of Health). Animals and Treatment (Experiments B-D)

ApoE and eNOS deficient mice (C57BL/6J background, Jackson Laboratory, Bar Harbor, Me.) are used. All animals are 10 to 12 weeks of age and weigh 22 to 28 g. Three days before surgery mice are divided into 4 groups (apoE control, n=10 to 12; apoE with test compounds, n=10 to 12; eNOS control, n=10 to 12; eNOS with test compounds, n=10 to 12) and receive either a standard rodent chow (containing 4% of fat and 0.001% of cholesterol; in the following designated as placebo group) or a standard rodent chow+test compound (10 or 30 mg/kg/day p.o.).
B) Anti-Hypertensive Effect in ApoE Knockout Mice Blood-pressure is determined in conscious mice using a computerized tail-cuff system (Visitech Systems, Apex, Nc). After treatment of ApoE deficient mice and eNOS deficient mice with the test compounds the blood pressure is compared to the results obtained with a placebo treatment.

C) Inhibition of Neointima Formation and Atherogenesis (Femoral Artery Cuff)

After 3 day treatment of ApoE deficient mice with the respective compound (10 mg/kg/day pressed in chow), animals are anesthetized with an intraperitoneal injection of pentobarbital (60 mg/kg) followed by an intramuscular injection of xylazin (2 mg/kg) and a cuff is placed around the femoral artery as described in Moroi et al. (J. Clin. Invest. 101 (1998) 1225). Briefly, the left femoral artery is dissected. A non-occlusive 2.0 mm polyethylene cuff made of PE 50 tubing (inner diameter 0.56 mm, outer diameter 0.965 mm, Becton Dickinson, Mountain View, Calif.) is placed around the artery and tied in place with two 7-0 sutures. The right femoral artery is isolated from the surrounding tissues but a cuff is not placed. Treatment with the respective compound is continued for 14 days after surgery. Then the animals are sacrificed. The aorta are taken for determination of vascular eNOS expressions by quantitative western blotting. Both femoral arteries are harvested, fixed in formalin and embedded in paraffin. 20 cross sections (10 µm) are cut from the cuffed portion of the left femoral artery and from the corresponding segment of the right artery. Sections are subjected to standard hematoxylin and eosin staining. Morphometric analyses are performed using an image analysis computer program (LeicaQWin, Leica Imaging Systems, Cambridge, GB). For each cross section the area of the lumen, the neointima and the media are determined. To this end, the neointima is defined as the area between the lumen and the internal elastic lamina and the media is defined as the area between the internal and the external elastic lamina. The ratio between the area of the neointima and the area of the media is expressed as the neointima/media ratio. The results obtained in the compound group are compared to those obtained in the placebo group.
D) Prevention of Atherosclerotic Plaque Formation in Chronic Treatment ApoE deficient mice are treated for 16 weeks with the respective compound pressed in chow and finally sacrificed. Aortas are removed from each mouse, fixed in formalin and embedded in paraffin. Plaque formation is measured via lipid lesions formation in the aortas (from aortic arch to diaphragm) and is analyzed by oil red O staining. For quantifying the effect of the respective compound on vascular eNOS expression the femoral arteries are used in this experiment. The results obtained in the compound group are compared to those obtained in the placebo group.
D) Improvement of Coronary Function in Diseased ApoE Deficient Mice Old Male wild-type C57BL/6J mice (Charles River Wiga GmbH, Sulzfeld), and apoE deficient mice (C57BL/6J background, Jackson Laboratory, Bar Harbor, Me.) of 6 month of age and weighing 28 to 36 g are used in the experiments. Mice are divided into 3 groups (C57BL/6J, n=8; apoE control, n=8; apoE with respective compound, n=8) and receive for 8 weeks either a standard rodent chow (containing 4% of fat and 0.001% of cholesterol) or a standard rodent chow+respective compound (30 mg/kg/day p.o.). Mice are anesthetized with sodium pentobarbitone (100 mg/kg i.p.), and the hearts are rapidly excised and placed into ice-cold perfusion buffer. The aorta is cannulated and connected to a perfusion apparatus (Hugo Sachs Electronics, Freiburg, Germany) which is started immediately at a constant perfusion pressure of 60 mm Hg. Hearts are perfused in a retrograde fashion with modified Krebs bicarbonate buffer, equilibrated with 95% $O_2$ and 5% $CO_2$ and maintained at 37.5° C. A beveled small tube (PE 50) is passed through a pulmonary vein into the left ventricle and pulled through the ventricular wall, anchored in the apex by a fluted end, and connected to a tip-micromanometer (Millar 1.4 French). The left atrium is cannulated through the same pulmonary vein and the heart switched to the working mode with a constant preload pressure of 10 mm Hg and an afterload pressure of 60 mm Hg. Aortic outflow and atrial inflow are continuously measured using ultrasonic flow probes (HSE/Transonic Systems Inc.). Coronary flow is calculated as the difference between atrial flow and aortic flow. All hemodynamic data are digitized at a sampling rate of 1000 Hz and recorded with a PC using specialized software (HEM, Notocord).

Hearts are allowed to stabilize for 30 min. All functional hemodynamic data are measured during steady state, and during volume and pressure loading. Left ventricular function curves are constructed by varying pre-load pressure. For acquisition of preload curves, afterload is set at 60 mm Hg and preload is adjusted in 5 mm Hg steps over a range of 5 to 25 mm Hg. Hearts are allowed to stabilize at baseline conditions between pressure and volume loading.

We claim:
1. A compound of formula I,

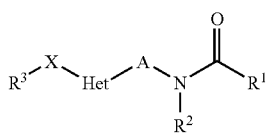

I wherein:
A is:

IIc which is optionally substituted by one or more identical or different substituents $R^4$;

Het is pyridinediyl, optionally substituted by one or more identical or different substituents $R^5$;

X is a direct bond;

$R^1$ and $R^2$, together with the N—CO group to which they are attached, form a 5-membered or 6-membered monocyclic saturated ring, which, in addition to the ring nitrogen atom being part of the N—CO group, optionally contains one additional hetero ring member $NR^{12}$, wherein the 5-membered or 6-membered ring is optionally substituted by one or more identical or different substituents $R^8$;

$R^3$ is selected from phenyl, naphthalenyl, and thienyl, each of which is optionally substituted by one or more identical or different substituents selected from the group consisting of halogen, $(C_1-C_4)$-alkyl, $(C_1-C_4)$-alkyloxy-$(C_1-C_2)$-alkyl-, OH, $(C_1-C_4)$-alkyloxy, $(C_1-C_2)$-alkylenedioxy, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, di($(C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—, wherein the substituents $(C_1-C_4)$-alkyloxy and $(C_1-C_2)$-alkylenedioxy are each independently optionally substituted by one or more fluorine atoms;

$R^4$ is $(C_1-C_4)$-alkyl or fluorine;

$R^5$ is halogen, $(C_1-C_4)$-alkyl, $(C_1-C_4)$-alkyloxy-$(C_1-C_2)$-alkyl-, OH, $(C_1-C_4)$-alkyloxy, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, di($(C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$ or $(C_1-C_4)$-alkyl-$SO_2$—, wherein the substituent $(C_1-C_4)$-alkyloxy is optionally substituted by one or more fluorine atoms;

$R^8$ is selected from halogen, $(C_1-C_4)$-alkyl, $(C_3-C_7)$-cycloalkyl-$C_nH_{2n}$—, phenyl-$C_nH_{2n}$— and oxo, wherein said phenyl is optionally substituted by one or more identical or different substituents selected from the group consisting of halogen, $(C_1-C_4)$-alkyl, $CF_3$ and $(C_1-C_4)$-alkyloxy;

$R^{12}$ is selected from hydrogen, $(C_1-C_4)$-alkyl, $(C_3-C_7)$-cycloalkyl-$C_nH_{2n}$—, and phenyl-$C_nH_{2n}$—, wherein phenyl is optionally substituted by one or more identical or different substituents selected from the group consisting of halogen, $(C_1-C_4)$-alkyl, $CF_3$ and $(C_1-C_4)$-alkyloxy;

n is 0, 1 or 2;

or its stereoisomeric form or a mixture of stereoisomeric forms in any ratio, or a physiologically acceptable salt thereof.

2. The compound according to claim 1, wherein $R^3$ is phenyl, optionally substituted by one or more identical or different substituents selected from the group consisting of halogen, $(C_1-C_4)$-alkyl, $(C_1-C_4)$-alkyloxy-$(C_1-C_2)$-alkyl-, $(C_1-C_4)$-alkyloxy, $(C_1-C_4)$-alkylmercapto, $(C_1-C_4)$-alkylamino, di($(C_1-C_4)$-alkyl)amino, $CONH_2$, CN, $CF_3$ and $(C_1-C_4)$-alkyl-$SO_2$—, wherein $(C_1-C_4)$-alkyloxy is optionally substituted by one or more fluorine atoms.

3. The compound according to claim 1, wherein $R^3$ is phenyl, optionally substituted by one or more identical or different substituents selected from the group consisting of halogen, $(C_1-C_4)$-alkyl, $(C_1-C_4)$-alkyloxy-$(C_1-C_2)$-alkyl-, $(C_1-C_4)$-alkyloxy, $(C_1-C_4)$-alkylmercapto, $(C_1-C_4)$-alkylamino, di($(C_1-C_4)$-alkyl)amino, $CONH_2$, CN, $CF_3$ and $(C_1-C_4)$-alkyl-$SO_2$—, wherein $(C_1-C_4)$-alkyloxy is optionally substituted by one or more fluorine atoms;

$R^5$ is halogen, $(C_1-C_4)$-alkyl, $(C_1-C_4)$-alkyloxy-$(C_1-C_2)$-alkyl-, OH, $(C_1-C_4)$-alkyloxy, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, $CONH_2$, CN, $CF_3$ or $(C_1-C_4)$-alkyl-$SO_2$—, wherein the substituent $(C_1-C_4)$-alkyloxy is optionally substituted by one or more fluorine atoms;

$R^8$ is $(C_1-C_4)$-alkyl or oxo; and $R^{12}$ is selected from H and $(C_1-C_4)$-alkyl-.

4. The compound according to claim 1, wherein $R^1$ and $R^2$, together with the N—CO group to which they are attached, form a 5-membered or 6-membered monocyclic saturated ring, which, in addition to the ring nitrogen atom of the N—CO group, contains one additional hetero ring member $NR^{12}$, as well as an additional oxo substituent.

5. The compound according to claim 1, wherein $R^1$ and $R^2$, together with the N—CO group to which they are attached, form a 5-membered or 6-membered monocyclic saturated ring selected from:

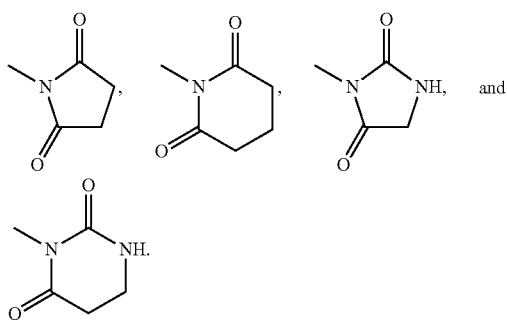

6. The compound according to claim 1, wherein A is not substituted by $R^4$.

7. A compound of the formula

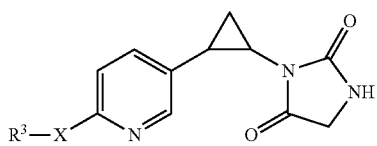

wherein:
X is a direct bond;
the pyridine ring is optionally substituted by one or more identical or different substituents $R^5$, wherein $R^5$ is selected from halogen, $(C_1-C_4)$-alkyl, $(C_1-C_4)$-alkyloxy-$(C_1-C_2)$-alkyl-, OH, $(C_1-C_4)$-alkyloxy, $(C_1-C_4)$-alkylmercapto, $NH_2$, $(C_1-C_4)$-alkylamino, $di((C_1-C_4)$-alkyl)amino, $((C_1-C_4)$-alkyl)-CONH—, $di((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$ and $(C_1-C_4)$-alkyl-$SO_2$—, wherein the substituent $(C_1-C_4)$-alkyloxy is optionally substituted by one or more fluorine atoms; and
$R^3$ is selected from phenyl, naphthalenyl, and thienyl, each of which is optionally substituted by one or more identical or different substituents selected from the group consisting of halogen, $(C_1-C_4)$-alkyl, $(C_1-C_4)$-alkyloxy-$(C_1-C_2)$-alkyl-, OH, $(C_1-C_4)$-alkyloxy, $(C_1-C_2)$-alkylenedioxy, $(C_1-C_4)$-alkylmercapto, $NH_2$, $(C_1-C_4)$-alkylamino, $di((C_1-C_4)$-alkyl)amino, $((C_1-C_4)$-alkyl)-CONH—, $di((C_1-C_4)$-alkyl)aminocarbonyl-, $((C_1-C_4)$-alkyl)aminocarbonyl-, $((C_1-C_4)$-alkyloxy)carbonyl-, COOH, $CONH_2$, CN, $CF_3$, $H_2NSO_2$— and $(C_1-C_4)$-alkyl-$SO_2$—, wherein the substituents $(C_1-C_4)$-alkyloxy and $(C_1-C_2)$-alkylenedioxy are each independently optionally substituted by one or more fluorine atoms;
or its stereoisomeric form or a mixture of stereoisomeric forms in any ratio, or a physiologically acceptable salt thereof.

8. The compound according to claim 7, wherein $R^3$ is optionally substituted phenyl or naphthalenyl.

9. The compound according to claim 7, wherein $R^3$ is optionally substituted phenyl.

10. The compound according to claim 7, wherein $R^5$ is selected from halogen and $(C_1-C_4)$-alkyl.

11. The compound according to claim 1, which is
(E)-3-(2-(6-(2,4-Difluorophenyl)pyridin-3-yl)cyclopropyl)imidazolidine-2,4-dione,
3-((E)-2-(6-(3-Chloro-4-fluorophenyl)pyridin-3-yl)cyclopropyl)imidazolidine-2,4-dione,
3-((E)-2-(6-(2,3-Difluorophenyl)pyridin-3-yl)cyclopropyl)imidazolidine-2,4-dione,
3-((E)-2-(6-(2,3-Dichlorophenyl)pyridin-3-yl)cyclopropyl)imidazolidine-2,4-dione,
3-((E)-2-(6-(4-Fluoro-3-methylphenyl)pyridin-3-yl)cyclopropyl)imidazolidine-2,4-dione,
3-((E)-2-(6-(3,4-Difluorophenyl)pyridin-3-yl)cyclopropyl)imidazolidine-2,4-dione,
3-((E)-2-(6-(4-Fluorophenyl)pyridin-3-yl)cyclopropyl)imidazolidine-2,4-dione,
3-((E)-2-(6-(3-Chloro-4-fluorophenyl)pyridin-3-yl)cyclopropyl)imidazolidine-2,4-dione,
3-((E)-2-(6-(4-fluoro-2-methylphenyl)pyridin-3-yl)cyclopropyl)imidazolidine-2,4-dione,
3-((E)-2-(6-(4-fluoronaphthalen-1-yl)pyridin-3-yl)cyclopropyl)imidazolidine-2,4-dione,
3-((E)-2-(6-(3,5-difluorophenyl)pyridin-3-yl)cyclopropyl)imidazolidine-2,4-dione,
3-((E)-2-(6-(2,3,4-trifluorophenyl)pyridin-3-yl)cyclopropyl)imidazolidine-2,4-dione,
3-((E)-2-(6-(3,4,5-trifluorophenyl)pyridin-3-yl)cyclopropyl)imidazolidine-2,4-dione,
3-((E)-2-(6-(3-cyano-4-fluorophenyl)pyridin-3-yl)cyclopropyl)imidazolidine-2,4-dione,
3-((E)-2-(6-(3,5-dichlorophenyl)pyridin-3-yl)cyclopropyl)imidazolidine-2,4-dione,
3-((E)-2-(6-(3,5-dimethylphenyl)pyridin-3-yl)cyclopropyl)imidazolidine-2,4-dione,
3-((E)-2-(6-(2,3-dimethylphenyl)pyridin-3-yl)cyclopropyl)imidazolidine-2,4-dione,
3-((E)-2-(6-(naphthalen-1-yl)pyridin-3-yl)cyclopropyl)imidazolidine-2,4-dione,
3-((E)-2-(6-(naphthalen-2-yl)pyridin-3-yl)cyclopropyl)imidazolidine-2,4-dione,
3-((E)-2-(6-(3,4-dichlorophenyl)pyridin-3-yl)cyclopropyl)imidazolidine-2,4-dione,
3-((E)-2-(6-(4-chloro-3-fluorophenyl)pyridin-3-yl)cyclopropyl)imidazolidine-2,4-dione,
3-((E)-2-(6-(3-fluoro-4-methylphenyl)pyridin-3-yl)cyclopropyl)imidazolidine-2,4-dione,
3-((E)-2-(6-(4-cyano-3-fluorophenyl)pyridin-3-yl)cyclopropyl)imidazolidine-2,4-dione,
3-((E)-2-(6-(4-trifluoromethylphenyl)pyridin-3-yl)cyclopropyl)imidazolidine-2,4-dione, or
3-((E)-2-(6-(5-methylthiophen-2-yl)pyridin-3-yl)cyclopropyl)imidazolidine-2,4-dione,
or its stereoisomeric form or a mixture of stereoisomeric forms in any ratio, or a physiologically acceptable salt thereof.

12. A pharmaceutical composition, comprising an effective amount of the compound according to claim 1, or its stereoisomeric form or a mixture of stereoisomeric forms in any ratio, or a physiologically acceptable salt thereof, and a pharmaceutically acceptable carrier.

* * * * *